US008916681B2

(12) United States Patent
Millar et al.

(10) Patent No.: US 8,916,681 B2
(45) Date of Patent: Dec. 23, 2014

(54) COMPOUND, USE AND METHOD

(75) Inventors: Robert Peter Millar, North Berwick (GB); Antonia Kathryn Roseweir, Inverkeithing (GB)

(73) Assignee: Medical Research Council, Swindon, Wiltshire (GB)

( * ) Notice: Subject to any disclaimer, the term of this patent is extended or adjusted under 35 U.S.C. 154(b) by 896 days.

(21) Appl. No.: 12/681,857

(22) PCT Filed: Oct. 8, 2008

(86) PCT No.: PCT/GB2008/003426
§ 371 (c)(1),
(2), (4) Date: Sep. 30, 2010

(87) PCT Pub. No.: WO2009/047513
PCT Pub. Date: Apr. 16, 2009

(65) Prior Publication Data
US 2011/0046068 A1    Feb. 24, 2011

Related U.S. Application Data

(60) Provisional application No. 60/978,179, filed on Oct. 8, 2007.

(30) Foreign Application Priority Data

Oct. 8, 2007  (GB) .................................. 0719592.8

(51) Int. Cl.
| | | |
|---|---|---|
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *A61K 38/22* | (2006.01) | |
| *C07K 14/575* | (2006.01) | |
| *A61K 38/09* | (2006.01) | |
| *A61P 5/02* | (2006.01) | |
| *A61K 38/10* | (2006.01) | |
| *A61K 38/17* | (2006.01) | |
| *A61K 38/00* | (2006.01) | |
| *A61P 35/00* | (2006.01) | |

(52) U.S. Cl.
CPC ........ *A61K 38/1709* (2013.01); *G01N 2500/04* (2013.01)
USPC ........... 530/328; 530/327; 514/9.7; 514/10.3; 514/21.5; 514/19.3

(58) Field of Classification Search
None
See application file for complete search history.

(56) References Cited

U.S. PATENT DOCUMENTS

| | | | |
|---|---|---|---|
| 6,420,123 B1 * | 7/2002 | Furka .............................. | 506/30 |
| 2004/0229933 A1 | 11/2004 | Katugampola | |
| 2006/0241051 A1 | 10/2006 | Kitada et al. | |
| 2007/0270339 A1 * | 11/2007 | Campbell et al. ............... | 514/12 |

FOREIGN PATENT DOCUMENTS

| | | |
|---|---|---|
| EP | 1 273 658 A1 | 1/2003 |
| EP | 1 921 066 | 5/2008 |
| JP | 2002-536989 | 11/2002 |
| JP | 2004-217651 | 8/2004 |
| WO | WO00/50563 | 8/2000 |
| WO | WO 2004/058716 A1 | 7/2004 |
| WO | WO 2004/060264 A2 | 7/2004 |
| WO | WO 2004/074831 | 9/2004 |
| WO | WO 2004/087125 | 10/2004 |
| WO | WO 2004/101747 A2 | 11/2004 |
| WO | WO 2005/117939 A2 | 12/2005 |
| WO | WO 2007/018319 | 2/2007 |
| WO | WO 2007/084211 A2 | 7/2007 |

OTHER PUBLICATIONS

Lehninger, Principles of Biochemistry, 4th Ed., pp. 661-663 (2004).*
Niida et al., "Design and synthesis of downsized metastin (45-54) analogs with maintenance of high GPR54 agonistic activity," Bioorgan. & Med. Chem. Letters 16:134-137 (first available online Oct. 2005).*
Ratcliffe et al., "Bifunctional Gonadotropin-Releasing Hormone Antagonist-Progesterone Analogs with Increased Efficacy and Duration of Action," Endocrinology 147:571-579 (first available Oct. 2005).*
Sun, et al., "The Reproductive Endocrine gm54/kisspepth Research Progress," *China Academic Journal Electronic Publishing House*, 25(5):438-440 (2005); provided with English-language machine translation.
Adachi, S., et al., "Involvement of Anteroventral Periventricular Metastin/Kisspeptin Neurons in Estrogen Positive Feedback Action on Luteinizing Hormone Release in Female Rats", *J Reprod Dev* 53(2):367-378 (2007).

(Continued)

*Primary Examiner* — James H Alstrum Acevedo
*Assistant Examiner* — Thea D'Ambrosio
(74) *Attorney, Agent, or Firm* — Hamilton, Brook, Smith & Reynolds, P.C.

(57) ABSTRACT

The present invention relates to the use of an antagonist of kisspeptin in the manufacture of a medicament for the treatment of a condition induced and/or worsened by kisspeptin activity in an individual. The invention also provides certain defined peptide molecules, which may act as an antagonist of kisspeptin, which are of use in treating a condition induced and/or worsened by kisspeptin activity in an individual. In addition, the invention provides methods of identifying and/or using antagonists of kisspeptin and/or the defined peptides, and pharmaceutical compositions thereof.

25 Claims, 38 Drawing Sheets

(56) References Cited

OTHER PUBLICATIONS

Figure 1:
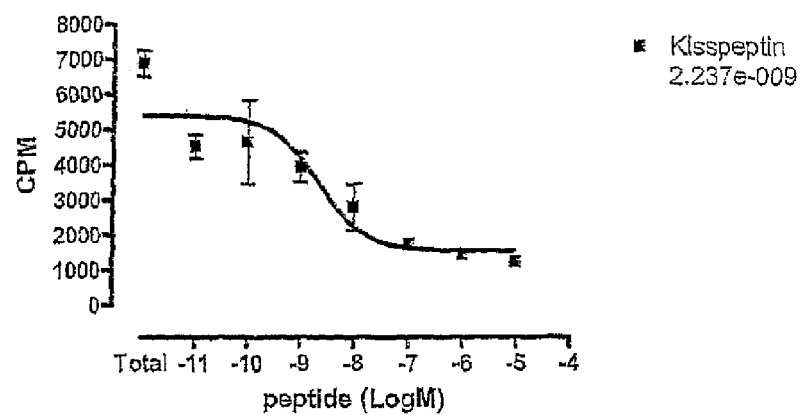
Figure 1:
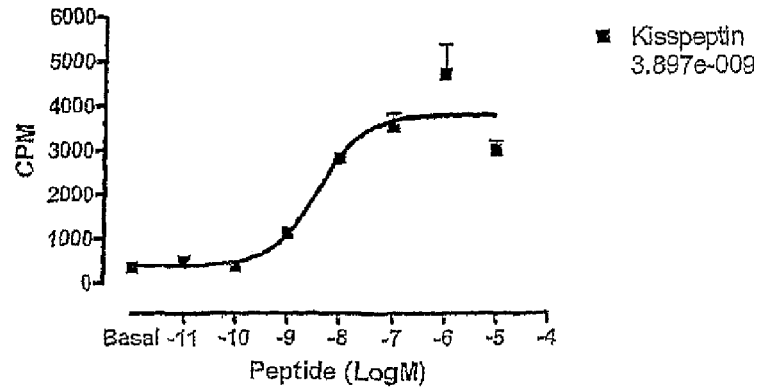

Arai, A.C., et al., "Cancer Metastasis-Suppressing Peptide Metastin Upregulates Excitatory Synaptic Transmission in Hippocampal Dentate Granule Cells", *J Neurophysiol* 94(5):3648-52 (2005).

Barker-Gibb, M.L., et al., "The Role of Neuropeptide Y (NPY) in the Control of LH Secretion in the Ewe With Respect to Season, NPY Receptor Subtype and the Site of Action in the Hypothalamus", *J Endocrinol* 147:565-579 (1995).

Bilban, M., et al., "Kisspeptin-10, a KiSS-1/Metastin-Derived Decapeptide, is a Physiological Invasion Inhibitor of Primary Human Trophoblasts", *J Cell Sci* 117(pt 8):1319-28 (2004).

Blank, S.K., et al., "The Origins and Sequelae of Abnormal Neuroendocrine Function in Polycystic Ovary Syndome", *Hum Reprod Update* 12(4):351-361 (2006).

Brailoiu, G.C., et al., "KiSS-1 Expression and Metastin-Like Immunoreactivity in the Rat Brain," *J. Comp. Neurol.* 481:314-329 (2005).

Burger, H.G., et al., "A Generalized Computer Program for the Treatment of Data From Competitive Protein-Binding Assays Including Radioimmunoassays," *J. Lab. Clin. Med* 80(2):302-312 (1972).

Castellano, J.M., et al., "Changes in Hypothalamic KiSS-1 System and Restoration of Pubertal Activation of the Reproductive Axis by Kisspeptin in Undernutrition", *Endocrinology* 146:3917-25 (2005).

Castellano, J.M., et al., "Expression of KiSS-1 in Rat Ovary: Putative Local Regulator of Ovulation?", *Endocrinology* 147:4852-62 (2006).

Centeno, M.L., et al., "Hypothalamic Gonadotrophin-Releasing Hormone Expression in Female Monkeys With Different Sensitivity to Stress", *J Neuroendocrinol* 19:594-604 (2007).

Cerrato, F., et al., "Coding Sequence Analysis of *GNRHR* and *GPR54* in Pateints With Congenital and Adult-Onset Forms of Hypogonadotropic Hypogonadism", *Eur I Endocrinol* 155:S3-S10 (2006).

Christian, C.A., et al., "Diurnal and Estradiol-Dependent Changes in Gonadotropin-Releasing Hormone Neurone Firing Activity", *Proc Natl Acad Sci USA* 102(43):15682-15687 (2005).

Clarke, I.J., "Variable Patterns of Gonadotropin-Releasing Hormone Secretion During the Estrogen-Induced Luteinizing Hormone Surge in Ovariectomized Ewes", *Endocrinology* 133:1624-1632 (1993).

Clarkson J. and Herbison, A.E., "Postnatal Development of Kisspeptin Neurons in Mouse Hypothalamus; Sexual Dimorphism and Projections to Gonadotropin-Releasing Hormone Neurons", *Endocrinology* 147:5817-25 (2006).

Clements, M.K., et al., "FMRFamide-Related Neuropeptides are Agonists of the Orphan G-Protein-Coupled Receptor GPR54", *Biochem Biophys Res Commun* 284:1189-1193 (2001).

Conn, P.M. and Crowley, W.F., Jr., "Gonadotropin-Releasing Hormone and its Analogs", *Annu Rev Med* 45:391-405 (1994).

Derossi, et al., "Trojan Peptides: The Penetratin System for Intracellular Delivery," *Trends Cell Biol* 8:84-87 (1998).

deRoux, N., et al., "Hypogonadotropic Hypogonadism Due to Loss of Function of the KiSS1—Derived Peptide Receptor GPR54", *Proc Natl Acad Sci USA* 100(19):10972-6 (2003).

Dhillo, W.S., et al., "Kisspeptin-54 Stimulates the Hypothalamic-Pituitary Gonadal Axis in Human Males", *J Clin Endocrinol Metab* 90(12):6609-15 (2005).

Dhillo, W.S., et al., "Kisspeptin-54 Stimulates Gonadotropin Release Most Potently During the Preovulatory Phase of the Menstrual Cycle in Women", *J Clin Endocrinol Metab* 92:3958-3966 (2007).

Dong, Q., et al., "LH Pulsatility, Biopotency, and Clearance During Undernutrition in Orchidectomized Mature Rats", *Am J Physiol* 265 (*Endocrinol. Metab.* 28):E304-313 (1993).

Estrada, K.M., et al., "Elevated KiSS-1 Expression in the Arcuate Nucleus Prior to the Cyclic Preovulatory Gonadotrophin-Releasing Hormone/Lutenising Hormone Surge in the Ewe Suggests a Stimulatory Role for Kisspeptin in Oestrogen-Positive Feedback", *J Neuroendocrinol* 18:806-9 (2006).

Fischer, P.M., et al., Structure-Activity Relationship of Truncated and Substituted Analogues of the Intracellular Delivery Vector Penetratin, *J. Peptide Res.*, 55:163-172 (2000).

Franceschini, I., et al., "Kisspeptin Immunoreactive Cells of the Ovine Preoptic Area and Arcuate Nucleus Co-express Estrogen Receptor Alpha", *Neurosci Lett* 401:225-30 (2006).

Fromme, B., et al., "A Novel Retro-Inverso Gonadotropin-Releasing Hormone (GnRH) Immunogen Elicits Antibodies That Neutralize the Activity of Native GnRH," *Endocrinology* 144:3262-3269 (2003).

Frost, S.I., et al., "Microdialysis Methods for in vivo Neuropeptide Measurement in the Stalk-Median Eminence in the Rhesus Monkey", *J. Neurosci Methods* 168(1):26-34 (2008).

Funes, S., et al., "The KiSS-1 Receptor GPR54 is Essential for the Development of the Muring Reproductive System", Biochem Biophys Res Commun 312:1357-63 (2003).

Gaytán, M., et al., "Expression of KiSS-1 in Rat Oviduct: Possible Involvement in Prevention of Ectopic Implantation?", Cell Tissue Res 329:571-579 (2007).

Gearing, M. and Terasawa E., "Luteinizing Hormone Releasing Hormone (LHRH) Neuroterminals Mapped Using the Push-Pull Perfusion Method in the Rhesus Monkey", *Brain Res Bull* 21:117-121 (1988).

Gottsch, M.L., et al., "A Role for Kisspeptins in the Regulation of Gonadotropin Secretion in the Mouse", *Endocrinology* 145:4073-4077 (2004).

Gottsch, M.L., et al., "Kisspepeptin-GPR54 Signaling in the Neuroendocrine Reproductive Axis", *Mol Cell Endocrinol* 254-255:91-96 (2006).

Greives, T.J., et al., "Environmental Control of Kisspeptin: Implications for Seasonal Reproduction", Endocrinology 148:1158-1166 (2007).

Gutiérrez-Pascual, E., et al., "Direct Pituitary Effects of Kisspeptin: Activation of Gonadotrophs and Somatotrophs and Stimulation of Luteinising Hormone and Growth Hormone Secretion", *J Neuroendocrinol* 19:521-30 (2007).

Han, S.K., et al., "Activation of Gonadotropin-Releasing Hormone Neurons by Kisspeptin as a Neuroendocrine Switch for the Onset of Puberty", *J. Neurosci* 25(49):11349-56 (2005).

Hiden, U., et al., "Kisspeptins and the Placenta: Regulation of Trophoblast Invasion", *Rev Endocr Metab Disord* 8:31-39 (2007).

Hori, A., et al., "Metastin Supresses the Motility and Growth of CHO Cells Transfected With its Receptor", Biochem Biophys Res Commun 286:958-63 (2001).

Horikoshi, Y., et al., "Dramatic Elevation of Plasma Metastin Concentrations in Human Pregnancy: Metastin as a Novel Placenta-Derived Hormone in Humans", *J Clin Endocrinol Metab* 88(2):914-9 (2003).

Irwig, M.S., et al., "Kisspeptin Activation of Gonadotropin Releasing Hormone Neurons and Regulation of KiSS-1 mRNA in the Male Rat", *Neuroendocrinology* 80:264-272 (2004).

Jacobi, J.S., et al., "17-Beta-Estradiol Directly Regulates the Expression of Adrenergic Receptors and Kisspeptin/GPR54 System in GT1-7 GnRH Neurons", *Neuroendocrinology* 86:260-269 (2007).

Janneau, J., et al., "Transcriptional Expression of Genes Involved in Cell Invasion and Migration by Normal and Tumoral Trophoblast Cells", *J Clin Endocrinol* 87:5336-9 (2002).

Keen, K.L., et al., "An Increase in Kisspeptin-54 Release Occurs With the Pubertal Increase in Luteinizing Hormone-Releasing Hormone-1 Release in the Stalk-Median Eminence of Female Rhesus Monkeys in Vivo", *Endocrinology* 149:4151-4157 (2008).

Kinoshita, M., et al., "Involvement of Central Metastin in the Regulation of Preovulatory Luteinizing Hormone Surge and Estrous Cyclicity in Female Rats", *Endocrinology* 146:4431-4436 (2005).

Kotani, M., et al., "The Metastasis Suppressor Gene KiSS-1 Encodes Kisspeptins, the Natural Ligands of the Orphan G Protein-Coupled Receptor GPR54", *J Biol Chem* 276(37):34631-6 (2001).

Kuohung, W. and Kaiser,U.B., "GPR54 and KiSS-1: Role in the Regulation of Puberty and Reproduction," *Rev Endocr Metab Disord* 7:257-263 (2006).

(56) References Cited

OTHER PUBLICATIONS

Lanfranco, F., et al., "Role of Sequence Variations of the GnRH Receptor and G Protein-Coupled Receptor 54 Gene in Male Idiopathic Hypogonadotropic Hypogonadism", *Eur J Endocrinol* 153:845-52 (2005).
Lee, D.K., et al., "Discovery of a Receptor Related to the Galanin Receptors", *FEBS* Lett 446:103-017 (1999).
Lee, V.W.K., et al., "Regulation of Gonadotrophin Secretion in Rams From Birth to Sexual Maturity," *J. Reprod. Fert.* 46:1-6 (1976).
Li, X.F., et al., "Neonatal Lipopolysaccharide Exposure Exacerbates Stress-Induced Suppression of Luteinizing Hormone Pulse Frequency in Adulthood", *Endocrinology* 148:5984.5990 (2007).
Lu, G., et al., "Improved Synthesis of 4-Alkoxybenzyl Alcohol Resin," *J. Org. Chem.* 46:3433-3436 (1981).
Luque, R.M., et al., "Regulation of Hypothalamic Expression of KiSS-1 and GPR54 Genes by Metabolic Factors: Analyses Using Mouse Models and a Cell Line", *Endocrinology* 148:46001-4611 (2007).
Mason, A.O., et al.,"Supression of Kisspeptin Expression and Gonadotropic Axis Sensitivity Following Exposure to Inhibitory Day Lengths in Female Siberian Hamsters", *Horm Behav* 52(4):492-498 (2007).
Masui, T., et al., "Metastin and its Variant Forms Suppress Migration of Pancreatic Cancer Cells", *Biochem Biophys Res Commun* 315:85-92 (2004).
Mead, E.J., et al., "Kisspeptins are Novel Potent Vasoconstrictors in Humans, With a Discrete Localization of Their Receptor, G Protein-Coupled Receptor 54, to Atherosclerosis Prone Vessels", *Endocrinology* 148(1):140-147 (2007).
Merriam, G.R. and Wachter, K.W., "Algorithms for the Study of Episodic Hormone Secretion", *Am J Physiol* 243 (Endocrinol. Metab. 6):E310-E318 (1982).
Messager, S., et al., "Kisspeptin Directly Stimulates Gonadotropin-Releasing Hormone Release Via G Protein-Coupled Receptor 54", *Proc Natl Acad Sci USA* 102(5):1761-6 (2005).
Mézière, C., et al., "In Vivo T Helper Cell Response to Retro-Inverso Peptidomimetics," *J. Immunol.* 159:3230-3237 (1997).
Millar, R.P., et al., "Gonadotropin-Releasing Hormone Receptors," *Endocr Rev* 25:235-275 (2004).
Mitchell, D.C., et al., "Transcriptional Regulation of KiSS-1 Gene Expression in Metastatic Melanoma by Specificity Protein-1 and its Coactivator DRIP-130," *Oncogene* 26:1739-47 (2007).
Muir, A.I., et al., "AXOR12, a Novel Human G Protein-Coupled Receptor, Activated by the Peptide KiSS-1", *J Biol Chem* 276(31):28969-75 (2001).
Navarro, V.M., et al., "Effects of KiSS-1 Peptide, the Natural Ligand of GPR54, on Follicle-Stimulating Hormone Secretion in the Rat", *Endocrinology* 146:1689-97 (2005).
Navarro, V.M., et al., "Characterization of the Potent Luteinizing Hormone-Releasing Activity of KiSS-1 Peptide, the Natural Ligand of GPR54", *Endocrinology* 146:156-163 (2005).
Navenot, J., et al., "Kisspeptin-10-Induced Signaling of GPR54 Negatively Regulates Chemotactic Responses Mediated by CXCR4: a Potential Mechanism for the Metastasis Supressor Activity of Kisspeptins", *Cancer Res* 65:10450-6 (2005).
Niida, A., et al., "Design and Synthesis of Downsized Metastin (45-54) Analogs With Maintenance of High GPR54 Agonistic Activity", *Bioorg Med Chem Lett* 16(1):134-7 (2006).
Nunemaker, C.S., et al., "Estradiol-Sensitive Afferents Modulate Long-Term Episodic Firing Patterns of GnRH Neurons", *Endocrinology* 143:2284-2292 (2002).
Ohtaki, T., et al., "Metastasis Supressor Gene KiSS-1 Encodes Peptide Ligand of a G-Protein-Coupled Receptor", *Nature* 411(6837):613-7 (2001).
Orsini, M.J., et al., "Metastin (KiSS-1) Mimetics Identified From Peptide Structure-Activity Relationship-Derived Pharmacophores and Directed Small Molecule Database Screening", *J Med Chem* 50:462-71 (2007).
Pallais, J.C., et al., "Neuroendocrine, Gonadal, Placental, and Obstetric Phenotypes in Patients With IHH and Mutations in the G-Protein Coupled Receptor, GPR54", *Mol Cell Endocrinol* 254-255:70-77 (2006).
Pielecka, J., et al., Direct and Indirect Actions of Kisspeptin on GnRH Neurons, Endocrine Society Meeting Abstract P1-8 (2006).
Pielecka, J. and Moenter, S.M., "Effect of Steroid Milieu on Gonadotropin-Releasing Hormone-1 Neuron Firing Pattern and Luteinizing Hormone Levels in Male Mice", *Biol Reprod* 74:931-937 (2006).
Pompolo, S., et al., "Colocalization of Kisspeptin and Gonadotropin-Releasing Hormone in the Ovine Brain", *Endocrinology* 147:804-10 (2006).
Porkka-Heiskanen, T., et al., "Rapid Photoperiod-Induced Increase in Detectable GnRH mRNA-Containing Cells in Siberian Hamster", *Am J Physiol Regul Integr Comp Physiol* 273:R2032-2039 (1997).
Qiao, C., et al., "Clinical Significance of KiSS-1 and Matrix Metalloproteinase-9 Expression in Trophoblasts of Women With Preeclampsia and Their Relation to Perinatal Outcome of Neonates", *Clin J. Obstet Gynecol.* 40(9):585-90 (2005).
Ratcliffe, K.E., et al., "Bifunctional Gonadotropin-Releasing Hormone Antagonist-Progesterone Analogs With Increased Efficacy and Duration of Action", *Endocrinology* 147:571-579 (2006).
Revel, F.G., et al., "KiSS-1: a Likely Candidate for the Photoperiodic Control of Reproduction in Seasonal Breeders", *Chronobiol Int* 23(1-2):277-87 (2006).
Revel, F.G., et al., "Kisspeptin Mediates the Photoperiodic Control of Reproduction in Hamsters", *Curr Biol* 16:1730-5 (2006).
Rich, D.H., Proteinase Inhibitors, Chapters 4 and 5, Barrett, A.J. and Salvesen, G., eds, Elsevier Science Publishers B.V. 1986.
Richardson, H.N., et al., "Female Pheromones Stimulate Release of Luteinizing Hormone and Testosterone Without Altering GnRH mRNA in Adult Male Syrian Hamster (*Mesocricetus auratus*)", *Gen Comp Endocrinol* 138:211-217 (2004).
Ringel, M.D., et al., "Metastin Receptor is Overexpressed in Papillary Thyroid Cancer and Activates MAP Kinase in Thyroid Cancer Cells", *J Clin Endocrinol Metab* 87:2399 2402 (2002).
Roa, J., et al., "Hypothalamic Expression of KiSS-1 System and Gonadotropin-Releasing Effects of Kisspeptin in Different Reproductive States of the Female Rat", Endocrinology 147:2864-2878 (2006).
Russell-Jones, G.J., et al., "Synthesis of LHRH Antagonists Suitable for Oral Administration via the Vitamin $B_{12}$ Uptake System", Bioconjugate Chem. 6:34-42 (1995).
Russell-Jones, G.J., et al., "Vitamin $B_{12}$ Mediated Oral Delivery Systems for Granulocyte-Colony Stimulating Factor and Erythropoietin", *Bioconjugate Chem.* 6:459-465 (1995).
Schmid, K., et al., "KiSS-1 Overexpression as an Independent Prognostic Marker in Hepatocellular Carcinoma: an Immunohistochemical Study", *Virchows Arch* 450:143-149 (2007).
Seminara, S.B., et al., "The *GPR54* Gene as a Regulator of Puberty", *N Engl J Med* 349:1614-27 (2003).
Seminara, S.B., and Kaiser, U.B., "New Gatekeepers of Reproduction: GPR54 and its Cognate Ligand, KiSS-1", *Endocrinology* 146:1686-1688 (2005).
Seminara, S.B., "Metastin and its G protein-Coupled Receptor, GPR54: Critical Pathway Modulating GnRH Secretion", *Frontiers in Neuroendocrinology* 26:131-138 (2005).
Semple, R.K., et al., "Two Novel Missense Mutations in G Protein-Coupled Receptor 54 in a Patient with Hypogonadotropic Hypogonadism", *J Clin Endocrinol Metab* 90:1849-55 (2005).
Shahab, M., et al., "Increased Hypothalamic GPR54 Signaling: A Potential Mechanism for Initiation of Puberty in Primates", *Proc Natl Acad Sci USA* 102(6):2129-34 (2005).
Sherman, D.B. and Spatola, A.F., "Compatibility of Thioamides With Reverse Turn Features: Synthesis and Conformational Analysis of Two Model Cyclic Pseudopeptides Containing Thioamides as Backbone Modifications", *J. Am. Chem. Soc.* 112:433-441 (1990).
Shirasaki, F., et al., "Loss of Expression of the Metastasis Supressor Gene KiSS1 During Melanoma Progression and its Association with LOH of Chromosome 6q16.3-q23", *Cancer Res* 61:7422-5 (2001).

(56) References Cited

OTHER PUBLICATIONS

Smith, J.T., et al., "Differential Regulation of KiSS-1 mRNA Expression by Sex Steroids in the Brain of the Male Mouse", *Endocrinology* 146:2976-84 (2005).
Stafford, L.J., et al., "Identification and Characterization of Mouse Metastasis-Supressor *KiSS1* and its G-Protein-Coupled Receptor", *Cancer Res* 62:5399-5404 (2002).
Stathatos, N., et al., "KiSS-1/G Protein-Coupled Receptor 54 Metastasis Supressor Pathway Increases Myocyte-Enriched Calcineurin Interacting Protein 1 Expression and Chronically Inhibits Calcineurin Activity", *J Clin Endocrinol Metab* 90:5432-40 (2005).
Suter, K.J., et al., "Genetic Targeting of Green Fluorescent Protein to Gonadotropin-Releasing Hormone Neurons: Characterization of Whole-Cell Electrophysiological Properties and Morphology", Endocrinology 141:412-419 (2000).
Suzuki, S., et al., "Direct Kisspeptin-10 Stimulation on Luteinizing Hormone Secretion From Bovine and Porcine Anterior Pituitary Cells", *Anim Reprod Sci* 103:360-365 (2008).
Tena-Sempere, M., "GPR54 and Kisspeptiin in Reproducion", *Human Reproduction Update* 12(5):631-639 (2006).
Tenenbaum-Rakover, Y., et al., "Neuroendocrine Phenotype Analysis in Five Patients With Isolated Hypogonadotropic Hypogonadism Due to a L102P Inactivating Mutation of GPR54", *J Clin Endocrinol Metab* 92:1137-1144 (2007).
Terao, Y., et al., "Expression of *KiSS-1*, a Metastasis Supressor Gene, in Trophoblast Giant Cells of the Rat Placenta", *Biochim Biophys Acta* 1678:102-10 (2004).
Thomas, G.B., et al., "Effect of Restricted Feeding on the Concentrations of Growth Hormone (GH), Gonadotropins, and Prolactin (PRL) in Plasma, and on the Amounts of Messenger Ribonucleic Acid for GH, Gonadotropin Subunits, and PRL in the Pituitary Glands of Adult Ovariectomized Ewes", *Endocrinology* 126:1361-1367 (1990).
Thompson, E.L., et al., "Central and Peripheral Administration of Kisspeptin-10 Stimulates the Hypothalamic-Pituitary-Gonadal Axis", *J. Neuroendocrinol* 16:850-858 (2004).
Thorsett, E.D., et al., "Dipeptide Mimics, Conformationally Restricted Inhibitors of Angiotensin-Converting Enzyme," *Biochemical and Biophysical Research Communications* 111(1):166-171 (1983).
Tomita, K., et al., "Structure-Activity Relationship Study on Small Peptidic GPR54 Agonists", *Bioorg Med Chem* 14:7595-7603 (2006).
Tsutsui, K., et al., "A Novel Avian Hypothalamic Peptide Inhibiting Gonadotropin Release", *Biochem Biophys Res Commun* 275(2):661-667 (2000).
Veber, D.F., et al., "Conformationally Restricted Bicyclic Analogs of Somatostatin", *Proc. Natl. Acad. Sci. USA* 75(6):2636-2640 (1978).
Wang, S., et al., "Synthesis and Biological Activity of Conjugates Between Paclitaxel and the Cell Delivery Vector Penetratin", *Bioorganic & Medicinal Chemistry Letters* 16:2628-2631 (2006).
West, A., et al., "Chromosome Localization and Genomic Structure of the KiSS-1 Metastasis Supressor Gene (KISS1)", *Genomics* 54:145-148 (1998).
Yamada, S., et al., "Inhibition of Metastin (Kisspeptin-54)-GPR 54 Signaling in the Arcuate Nucleus-Median Eminence Region During Lactation in Rats", *Endocrinology* 148:2226-2232 (2007).
Notification Concerning Transmittal of International Preliminary Report on Patentability (IPRP) with IPRP and Written Opinion, PCT/GB2008/003426, mailed Apr. 22, 2010.

\* cited by examiner

Kisspeptin - YNWNSFGLRF (SEQ ID NO:1)

A

B

The ability of repeated injections of the compounds (3 injections i.c.v. of 1nmol every 60-min) to interfere with the potent LH-releasing effect of kisspeptin-10 (100 pmol) in intact male The ability of repeated injections of 234 (3 injections
i.c.v. of 1nmol every 60-min) to interfere with the potent
LH-releasing effect of kisspeptin-10 (100 pmol) in intact
male rats. Inserts show AUC for LH and testerone.

The ability of repeated injections of the compounds (3 injections i.c.v. of 1nmol every 60-min) to attenuate the elevated LH levels in orchidectomized (ORX) male rats. Insert shows AUC for LH

186

187

188

189

215

228

229

230

231

232

233

234

239

240

241

242

243

244

245

246

247

248

A

B

A

B

SEQUENCE LISTING

```
<160> NUMBER OF SEQ ID NOS: 93

<210> SEQ ID NO 1
<211> LENGTH: 10
<212> TYPE: PRT
<213> ORGANISM: Homo sapiens
<220> FEATURE:
<221> NAME/KEY: SITE
<222> LOCATION: (1)...(10)
<223> OTHER INFORMATION: Kisspeptin 1-10 sequence
<220> FEATURE:
<221> NAME/KEY: SITE
<222> LOCATION: 10
<223> OTHER INFORMATION: NH2 group

<400> SEQUENCE: 1

Tyr Asn Trp Asn Ser Phe Gly Leu Arg Phe
1               5                   10

<210> SEQ ID NO 2
<211> LENGTH: 54
<212> TYPE: PRT
<213> ORGANISM: Homo sapiens
<220> FEATURE:
<221> NAME/KEY: SITE
<222> LOCATION: (1)...(54)
<223> OTHER INFORMATION: Kisspeptin 1-54 sequence
<220> FEATURE:
<221> NAME/KEY: SITE
<222> LOCATION: 54
<223> OTHER INFORMATION: NH2 group

<400> SEQUENCE: 2

Gly Thr Ser Leu Ser Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 3
<211> LENGTH: 5
<212> TYPE: PRT
<213> ORGANISM: Artificial Sequence
<220> FEATURE:
<223> OTHER INFORMATION: Kisspeptin variant sequence
<220> FEATURE:
```

-continued

```
<221> NAME/KEY: VARIANT
<222> LOCATION: 1
<223> OTHER INFORMATION: Xaa = F or A or any D-amino acid
<220> FEATURE:
<221> NAME/KEY: VARIANT
<222> LOCATION: 2
<223> OTHER INFORMATION: G or W
<220> FEATURE:
<221> NAME/KEY: VARIANT
<222> LOCATION: 3
<223> OTHER INFORMATION: Xaa = L or A or any D-amino acid
<220> FEATURE:
<221> NAME/KEY: VARIANT
<222> LOCATION: 4
<223> OTHER INFORMATION: R or (D)R
<220> FEATURE:
<221> NAME/KEY: VARIANT
<222> LOCATION: 5
<223> OTHER INFORMATION: Xaa = F or A or any D-amino acid

<400> SEQUENCE: 3

Xaa Gly Xaa Arg Xaa
 1               5

<210> SEQ ID NO 4
<211> LENGTH: 5
<212> TYPE: PRT
<213> ORGANISM: Artificial Sequence
<220> FEATURE:
<223> OTHER INFORMATION: Kisspeptin variant sequence

<400> SEQUENCE: 4

Phe Gly Leu Arg Phe
 1               5

<210> SEQ ID NO 5
<211> LENGTH: 5
<212> TYPE: PRT
<213> ORGANISM: Artificial Sequence
<220> FEATURE:
<223> OTHER INFORMATION: Kisspeptin variant sequence

<400> SEQUENCE: 5

Phe Gly Leu Arg Trp
 1               5

<210> SEQ ID NO 6
<211> LENGTH: 5
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 3
<223> OTHER INFORMATION: (D)F

<400> SEQUENCE: 6

Phe Gly Phe Arg Phe
 1               5

<210> SEQ ID NO 7
<211> LENGTH: 5
<212> TYPE: PRT
<213> ORGANISM: Artificial Sequence
<220> FEATURE:
<223> OTHER INFORMATION: Kisspeptin variant sequence

<400> SEQUENCE: 7

Phe Gly Ala Arg Trp
```

```
<210> SEQ ID NO 8
<211> LENGTH: 5
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 4
<223> OTHER INFORMATION: (D)R

<400> SEQUENCE: 8

Phe Gly Leu Arg Trp
1               5

<210> SEQ ID NO 9
<211> LENGTH: 5
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 3
<223> OTHER INFORMATION: (D)L

<400> SEQUENCE: 9

Phe Gly Leu Arg Trp
1               5

<210> SEQ ID NO 10
<211> LENGTH: 5
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)F

<400> SEQUENCE: 10

Phe Gly Leu Arg Trp
1               5

<210> SEQ ID NO 11
<211> LENGTH: 5
<212> TYPE: PRT
<213> ORGANISM: Artificial Sequence
<220> FEATURE:
<223> OTHER INFORMATION: Kisspeptiin Variant Sequence
<220> FEATURE:
<221> NAME/KEY: SITE
<222> LOCATION: 1
<223> OTHER INFORMATION: (D)F

<400> SEQUENCE: 11

Phe Trp Leu Arg Trp
1               5

<210> SEQ ID NO 12
<211> LENGTH: 5
<212> TYPE: PRT
<213> ORGANISM: Artificial Sequence
<220> FEATURE:
<223> OTHER INFORMATION: Kisspeptiin Variant Sequence
<220> FEATURE:
<221> NAME/KEY: SITE
```

```
<222> LOCATION: 3
<223> OTHER INFORMATION: (D)W

<400> SEQUENCE: 12

Phe Gly Trp Arg Phe
 1               5

<210> SEQ ID NO 13
<211> LENGTH: 5
<212> TYPE: PRT
<213> ORGANISM: Artificial Sequence
<220> FEATURE:
<223> OTHER INFORMATION: Kisspeptiin Variant Sequence
<220> FEATURE:
<221> NAME/KEY: SITE
<222> LOCATION: 6
<223> OTHER INFORMATION: (D)F

<400> SEQUENCE: 13

Phe Gly Phe Arg Trp
 1               5

<210> SEQ ID NO 14
<211> LENGTH: 5
<212> TYPE: PRT
<213> ORGANISM: Artificial Sequence
<220> FEATURE:
<223> OTHER INFORMATION: Kisspeptiin Variant Sequence
<220> FEATURE:
<221> NAME/KEY: SITE
<222> LOCATION: 3
<223> OTHER INFORMATION: (D)L

<400> SEQUENCE: 14

Phe Gly Leu Arg Trp
 1               5

<210> SEQ ID NO 15
<211> LENGTH: 5
<212> TYPE: PRT
<213> ORGANISM: Artificial Sequence
<220> FEATURE:
<223> OTHER INFORMATION: Kisspeptiin Variant Sequence
<220> FEATURE:
<221> NAME/KEY: SITE
<222> LOCATION: 4
<223> OTHER INFORMATION: (D)R

<400> SEQUENCE: 15

Phe Gly Leu Arg Trp
 1               5

<210> SEQ ID NO 16
<211> LENGTH: 5
<212> TYPE: PRT
<213> ORGANISM: Artificial Sequence
<220> FEATURE:
<223> OTHER INFORMATION: Kisspeptiin Variant Sequence

<400> SEQUENCE: 16

Phe Gly Ala Arg Trp
 1               5

<210> SEQ ID NO 17
<211> LENGTH: 5
<212> TYPE: PRT
<213> ORGANISM: Artificial Sequence
<220> FEATURE:
<223> OTHER INFORMATION: Kisspeptiin Variant Sequence
```

```
<400> SEQUENCE: 17

Ala Gly Leu Arg Trp
 1               5

<210> SEQ ID NO 18
<211> LENGTH: 5
<212> TYPE: PRT
<213> ORGANISM: Artificial Sequence
<220> FEATURE:
<223> OTHER INFORMATION: Kisspeptiin Variant Sequence
<220> FEATURE:
<221> NAME/KEY: SITE
<222> LOCATION: 1
<223> OTHER INFORMATION: (D)F

<400> SEQUENCE: 18

Phe Trp Leu Arg Trp
 1               5

<210> SEQ ID NO 19
<211> LENGTH: 5
<212> TYPE: PRT
<213> ORGANISM: Artificial Sequence
<220> FEATURE:
<223> OTHER INFORMATION: Kisspeptiin Variant Sequence
<220> FEATURE:
<221> NAME/KEY: SITE
<222> LOCATION: 3
<223> OTHER INFORMATION: (D)W

<400> SEQUENCE: 19

Phe Gly Trp Arg Phe
 1               5

<210> SEQ ID NO 20
<211> LENGTH: 8
<212> TYPE: PRT
<213> ORGANISM: Artificial Sequence
<220> FEATURE:
<223> OTHER INFORMATION: Drosophila melanogaster
<220> FEATURE:
<221> NAME/KEY: SITE
<222> LOCATION: (1)...(8)
<223> OTHER INFORMATION: Antennapedia N terminal sequence

<400> SEQUENCE: 20

Arg Arg Met Lys Trp Lys Lys Tyr
 1               5

<210> SEQ ID NO 21
<211> LENGTH: 13
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 11
<223> OTHER INFORMATION: (D)F

<400> SEQUENCE: 21

Arg Arg Met Lys Trp Lys Lys Tyr Phe Gly Phe Arg Trp
 1               5                  10

<210> SEQ ID NO 22
<211> LENGTH: 13
<212> TYPE: PRT
```

-continued

```
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 11
<223> OTHER INFORMATION: (D)L

<400> SEQUENCE: 22

Arg Arg Met Lys Trp Lys Lys Tyr Phe Gly Leu Arg Trp
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 12
<223> OTHER INFORMATION: (D)R

<400> SEQUENCE: 23

Arg Arg Met Lys Trp Lys Lys Tyr Phe Gly Leu Arg Trp
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Kisspeptin variant sequence with N terminal
      antennapedia sequence

<400> SEQUENCE: 24

Arg Arg Met Lys Trp Lys Lys Tyr Phe Gly Ala Arg Trp
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Kisspeptin variant sequence with N terminal
      antennapedia sequence

<400> SEQUENCE: 25

Arg Arg Met Lys Trp Lys Lys Tyr Ala Gly Leu Arg Trp
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)F

<400> SEQUENCE: 26

Arg Arg Met Lys Trp Lys Lys Tyr Phe Trp Leu Arg Trp
1               5                   10
```

```
<210> SEQ ID NO 27
<211> LENGTH: 13
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 11
<223> OTHER INFORMATION: (D)W

<400> SEQUENCE: 27

Arg Arg Met Lys Trp Lys Lys Tyr Phe Gly Trp Arg Phe
1               5                   10

<210> SEQ ID NO 28
<211> LENGTH: 49
<212> TYPE: PRT
<213> ORGANISM: Homo sapiens
<220> FEATURE:
<221> NAME/KEY: SITE
<222> LOCATION: (1)...(49)
<223> OTHER INFORMATION: Kisspeptin 1-45 sequence

<400> SEQUENCE: 28

Gly Thr Ser Leu Ser Pro Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser

<210> SEQ ID NO 29
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: VARIANT
<222> LOCATION: 1
<223> OTHER INFORMATION: Xaa = Y or any D-amino acid
<220> FEATURE:
<221> NAME/KEY: VARIANT
<222> LOCATION: 2
<223> OTHER INFORMATION: Xaa = N or any D-amino acid
<220> FEATURE:
<221> NAME/KEY: VARSPLIC
<222> LOCATION: 3
<223> OTHER INFORMATION: Xaa = W or any D-amino acid
<220> FEATURE:
<221> NAME/KEY: VARIANT
<222> LOCATION: 5
<223> OTHER INFORMATION: Xaa = G or S or any D-amino acid
<220> FEATURE:
<221> NAME/KEY: VARIANT
<222> LOCATION: 6
<223> OTHER INFORMATION: Xaa = F or (D)W or (D)L
<220> FEATURE:
<221> NAME/KEY: VARIANT
<222> LOCATION: (8)...(8)
<223> OTHER INFORMATION: W or L or any D-amino acid

<400> SEQUENCE: 29

Xaa Xaa Xaa Asn Xaa Xaa Gly Xaa Arg Phe
1               5                   10

<210> SEQ ID NO 30
```

```
<211> LENGTH: 10
<212> TYPE: PRT
<213> ORGANISM: Artificial Sequence
<220> FEATURE:
<223> OTHER INFORMATION: Kisspeptin variant sequence

<400> SEQUENCE: 30

Tyr Asn Trp Asn Ser Phe Gly Leu Arg Phe
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)Y
<220> FEATURE:
<221> NAME/KEY: SITE
<222> LOCATION: 2
<223> OTHER INFORMATION: (D)N

<400> SEQUENCE: 31

Tyr Asn Trp Asn Ser Phe Gly Trp Arg Phe
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)Y
<220> FEATURE:
<221> NAME/KEY: SITE
<222> LOCATION: 2
<223> OTHER INFORMATION: (D)N

<400> SEQUENCE: 32

Tyr Asn Trp Asn Gly Phe Gly Trp Arg Phe
 1               5                  10

<210> SEQ ID NO 33
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)Y
<220> FEATURE:
<221> NAME/KEY: SITE
<222> LOCATION: 2
<223> OTHER INFORMATION: (D)N
<220> FEATURE:
<221> NAME/KEY: SITE
<222> LOCATION: 1
<223> OTHER INFORMATION: (D)W

<400> SEQUENCE: 33

Tyr Asn Trp Asn Ser Phe Gly Trp Arg Phe
 1               5                  10
```

```
<210> SEQ ID NO 34
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)Y
<220> FEATURE:
<221> NAME/KEY: SITE
<222> LOCATION: 2
<223> OTHER INFORMATION: (D)N

<400> SEQUENCE: 34

Tyr Asn Trp Asn Gly Phe Gly Trp Arg Phe
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Kisspeptin variant sequence

<400> SEQUENCE: 35

Tyr Asn Trp Asn Gly Phe Gly Leu Arg Phe
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 8
<223> OTHER INFORMATION: (D)L

<400> SEQUENCE: 36

Tyr Asn Trp Asn Gly Phe Gly Leu Arg Phe
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 8
<223> OTHER INFORMATION: (D)W

<400> SEQUENCE: 37

Tyr Asn Trp Asn Gly Phe Gly Trp Arg Phe
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 6
<223> OTHER INFORMATION: (D)W
```

```
<400> SEQUENCE: 38

Tyr Asn Trp Asn Gly Trp Gly Leu Arg Phe
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 8
<223> OTHER INFORMATION: (D)W

<400> SEQUENCE: 39

Tyr Asn Trp Asn Gly Phe Gly Trp Arg Phe
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 5
<223> OTHER INFORMATION: (D)W
<220> FEATURE:
<221> NAME/KEY: SITE
<222> LOCATION: 8
<223> OTHER INFORMATION: (D)W

<400> SEQUENCE: 40

Tyr Asn Trp Asn Trp Phe Gly Trp Arg Phe
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 8
<223> OTHER INFORMATION: (D)W

<400> SEQUENCE: 41

Tyr Asn Trp Asn Gly Phe Gly Trp Arg Phe
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 3
<223> OTHER INFORMATION: (D)W
<220> FEATURE:
<221> NAME/KEY: SITE
<222> LOCATION: 8
<223> OTHER INFORMATION: (D)W

<400> SEQUENCE: 42

Tyr Asn Trp Asn Gly Phe Gly Trp Arg Phe
```

1               5                   10

<210> SEQ ID NO 43
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 2
<223> OTHER INFORMATION: (D)N
<220> FEATURE:
<221> NAME/KEY: SITE
<222> LOCATION: 8
<223> OTHER INFORMATION: (D)W

<400> SEQUENCE: 43

Tyr Asn Trp Asn Gly Phe Gly Trp Arg Phe
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 5
<223> OTHER INFORMATION: (D)A
<220> FEATURE:
<221> NAME/KEY: SITE
<222> LOCATION: 8
<223> OTHER INFORMATION: (D)W

<400> SEQUENCE: 44

Tyr Asn Trp Asn Ala Phe Gly Trp Arg Phe
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)A
<220> FEATURE:
<221> NAME/KEY: SITE
<222> LOCATION: 8
<223> OTHER INFORMATION: (D)W

<400> SEQUENCE: 45

Ala Asn Trp Asn Gly Phe Gly Trp Arg Phe
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 3
<223> OTHER INFORMATION: (D)A
<220> FEATURE:
<221> NAME/KEY: SITE
<222> LOCATION: 8

<223> OTHER INFORMATION: (D)W

<400> SEQUENCE: 46

Tyr Asn Ala Asn Gly Phe Gly Trp Arg Phe
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 2
<223> OTHER INFORMATION: (D)A
<220> FEATURE:
<221> NAME/KEY: SITE
<222> LOCATION: 8
<223> OTHER INFORMATION: (D)W

<400> SEQUENCE: 47

Tyr Ala Trp Asn Gly Phe Gly Trp Arg Phe
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)W
<220> FEATURE:
<221> NAME/KEY: SITE
<222> LOCATION: 8
<223> OTHER INFORMATION: (D)W

<400> SEQUENCE: 48

Trp Asn Trp Asn Gly Phe Gly Trp Arg Phe
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)F
<220> FEATURE:
<221> NAME/KEY: SITE
<222> LOCATION: 8
<223> OTHER INFORMATION: (D)W

<400> SEQUENCE: 49

Phe Asn Trp Asn Gly Phe Gly Trp Arg Phe
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE

```
<222> LOCATION: 1
<223> OTHER INFORMATION: (D)Y
<220> FEATURE:
<221> NAME/KEY: SITE
<222> LOCATION: 6
<223> OTHER INFORMATION: (D)W
<220> FEATURE:
<221> NAME/KEY: SITE
<222> LOCATION: 8
<223> OTHER INFORMATION: (D)W

<400> SEQUENCE: 50

Tyr Asn Trp Asn Gly Trp Gly Trp Arg Phe
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)A
<220> FEATURE:
<221> NAME/KEY: SITE
<222> LOCATION: 6
<223> OTHER INFORMATION: (D)W
<220> FEATURE:
<221> NAME/KEY: SITE
<222> LOCATION: 8
<223> OTHER INFORMATION: (D)W

<400> SEQUENCE: 51

Ala Asn Trp Asn Gly Trp Gly Trp Arg Phe
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)A
<220> FEATURE:
<221> NAME/KEY: SITE
<222> LOCATION: 8
<223> OTHER INFORMATION: (D)W

<400> SEQUENCE: 52

Ala Asn Trp Asn Ser Phe Gly Trp Arg Phe
 1               5                  10

<210> SEQ ID NO 53
<211> LENGTH: 11
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)A

<400> SEQUENCE: 53

Asp Ala Asn Trp Asn Gly Phe Gly Trp Arg Phe
 1               5                  10
```

```
<210> SEQ ID NO 54
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)A
<220> FEATURE:
<221> NAME/KEY: SITE
<222> LOCATION: 5
<223> OTHER INFORMATION: (D)S
<220> FEATURE:
<221> NAME/KEY: SITE
<222> LOCATION: 8
<223> OTHER INFORMATION: (D)W

<400> SEQUENCE: 54

Ala Asn Trp Asn Ser Phe Gly Trp Arg Phe
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: Kisspeptin variant sequence
<220> FEATURE:
<221> NAME/KEY: SITE
<222> LOCATION: 1
<223> OTHER INFORMATION: (D)A
<220> FEATURE:
<221> NAME/KEY: SITE
<222> LOCATION: 8
<223> OTHER INFORMATION: (D)L

<400> SEQUENCE: 55

Ala Asn Trp Asn Gly Phe Gly Leu Arg Phe
 1               5                  10

<210> SEQ ID NO 56
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence

<400> SEQUENCE: 56

Arg Arg Met Lys Trp Lys Lys Tyr Tyr Asn Trp Asn Gly Phe Gly Leu
 1               5                  10                  15

Arg Phe

<210> SEQ ID NO 57
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 16
<223> OTHER INFORMATION: (D)L

<400> SEQUENCE: 57

Arg Arg Met Lys Trp Lys Lys Tyr Tyr Asn Trp Asn Gly Phe Gly Leu
 1               5                  10                  15
```

Arg Phe

```
<210> SEQ ID NO 58
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 16
<223> OTHER INFORMATION: (D)W
```

<400> SEQUENCE: 58

Arg Arg Met Lys Trp Lys Lys Tyr Tyr Asn Trp Asn Gly Phe Gly Trp
1               5                   10                  15

Arg Phe

```
<210> SEQ ID NO 59
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 14
<223> OTHER INFORMATION: (D)W
```

<400> SEQUENCE: 59

Arg Arg Met Lys Trp Lys Lys Tyr Tyr Asn Trp Asn Gly Trp Gly Leu
1               5                   10                  15

Arg Phe

```
<210> SEQ ID NO 60
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 16
<223> OTHER INFORMATION: (D)W
```

<400> SEQUENCE: 60

Arg Arg Met Lys Trp Lys Lys Tyr Tyr Asn Trp Asn Gly Phe Gly Trp
1               5                   10                  15

Arg Phe

```
<210> SEQ ID NO 61
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 13
<223> OTHER INFORMATION: (D)W
<220> FEATURE:
<221> NAME/KEY: SITE
<222> LOCATION: 16
<223> OTHER INFORMATION: (D)W
```

```
<400> SEQUENCE: 61

Arg Arg Met Lys Trp Lys Lys Tyr Tyr Asn Trp Asn Trp Phe Gly Trp
 1               5                   10                  15

Arg Phe

<210> SEQ ID NO 62
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 16
<223> OTHER INFORMATION: (D)W

<400> SEQUENCE: 62

Arg Arg Met Lys Trp Lys Lys Tyr Tyr Asn Trp Asn Gly Phe Gly Trp
 1               5                   10                  15

Arg Phe

<210> SEQ ID NO 63
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 11
<223> OTHER INFORMATION: (D)W
<220> FEATURE:
<221> NAME/KEY: SITE
<222> LOCATION: 16
<223> OTHER INFORMATION: (D)W

<400> SEQUENCE: 63

Arg Arg Met Lys Trp Lys Lys Tyr Tyr Asn Trp Asn Gly Phe Gly Trp
 1               5                   10                  15

Arg Phe

<210> SEQ ID NO 64
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 10
<223> OTHER INFORMATION: (D)N
<220> FEATURE:
<221> NAME/KEY: SITE
<222> LOCATION: 16
<223> OTHER INFORMATION: (D)W

<400> SEQUENCE: 64

Arg Arg Met Lys Trp Lys Lys Tyr Tyr Asn Trp Asn Gly Phe Gly Trp
 1               5                   10                  15

Arg Phe

<210> SEQ ID NO 65
<211> LENGTH: 18
```

```
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 10
<223> OTHER INFORMATION: (D)A
<220> FEATURE:
<221> NAME/KEY: SITE
<222> LOCATION: 16
<223> OTHER INFORMATION: (D)W

<400> SEQUENCE: 65

Arg Arg Met Lys Trp Lys Lys Tyr Tyr Asn Trp Asn Ala Phe Gly Trp
1               5                   10                  15

Arg Phe

<210> SEQ ID NO 66
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 10
<223> OTHER INFORMATION: (D)A
<220> FEATURE:
<221> NAME/KEY: SITE
<222> LOCATION: 16
<223> OTHER INFORMATION: (D)W

<400> SEQUENCE: 66

Arg Arg Met Lys Trp Lys Lys Tyr Ala Asn Trp Asn Gly Phe Gly Trp
1               5                   10                  15

Arg Phe

<210> SEQ ID NO 67
<211> LENGTH: 18
<212> TYPE: PRT
<213> ORGANISM: Artificial Sequence
<220> FEATURE:
<223> OTHER INFORMATION: Antennapedia N terminal sequence
<220> FEATURE:
<221> NAME/KEY: SITE
<222> LOCATION: 11
<223> OTHER INFORMATION: (D)A
<220> FEATURE:
<221> NAME/KEY: SITE
<222> LOCATION: 16
<223> OTHER INFORMATION: (D)W

<400> SEQUENCE: 67

Arg Arg Met Lys Trp Lys Lys Tyr Tyr Asn Ala Asn Gly Phe Gly Trp
1               5                   10                  15

Arg Phe

<210> SEQ ID NO 68
<211> LENGTH: 18
<212> TYPE: PRT
<213> ORGANISM: Artificial Sequence
<220> FEATURE:
<223> OTHER INFORMATION: Antennapedia N terminal sequence
<220> FEATURE:
<221> NAME/KEY: SITE
<222> LOCATION: 10
<223> OTHER INFORMATION: (D)A
```

```
<220> FEATURE:
<221> NAME/KEY: SITE
<222> LOCATION: 16
<223> OTHER INFORMATION: (D)W

<400> SEQUENCE: 68

Arg Arg Met Lys Trp Lys Lys Tyr Tyr Ala Trp Asn Gly Phe Gly Trp
1               5                   10                  15

Arg Phe

<210> SEQ ID NO 69
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)W
<220> FEATURE:
<221> NAME/KEY: SITE
<222> LOCATION: 16
<223> OTHER INFORMATION: (D)W

<400> SEQUENCE: 69

Arg Arg Met Lys Trp Lys Lys Tyr Trp Asn Trp Asn Gly Phe Gly Trp
1               5                   10                  15

Arg Phe

<210> SEQ ID NO 70
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)F
<220> FEATURE:
<221> NAME/KEY: SITE
<222> LOCATION: 16
<223> OTHER INFORMATION: (D)W

<400> SEQUENCE: 70

Arg Arg Met Lys Trp Lys Lys Tyr Phe Asn Trp Asn Gly Phe Gly Trp
1               5                   10                  15

Arg Phe

<210> SEQ ID NO 71
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)Y
<220> FEATURE:
<221> NAME/KEY: SITE
<222> LOCATION: 14
<223> OTHER INFORMATION: (D)W
<220> FEATURE:
<221> NAME/KEY: SITE
<222> LOCATION: 16
```

<223> OTHER INFORMATION: (D)W

<400> SEQUENCE: 71

Arg Arg Met Lys Trp Lys Lys Tyr Tyr Asn Trp Asn Gly Trp Gly Trp
1               5                   10                  15

Arg Phe

<210> SEQ ID NO 72
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)A
<220> FEATURE:
<221> NAME/KEY: SITE
<222> LOCATION: 14
<223> OTHER INFORMATION: (D)W
<220> FEATURE:
<221> NAME/KEY: SITE
<222> LOCATION: 16
<223> OTHER INFORMATION: (D)W

<400> SEQUENCE: 72

Arg Arg Met Lys Trp Lys Lys Tyr Ala Asn Trp Asn Gly Trp Gly Trp
1               5                   10                  15

Arg Phe

<210> SEQ ID NO 73
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)A
<220> FEATURE:
<221> NAME/KEY: SITE
<222> LOCATION: 16
<223> OTHER INFORMATION: (D)W

<400> SEQUENCE: 73

Arg Arg Met Lys Trp Lys Lys Tyr Ala Asn Trp Asn Ser Phe Gly Trp
1               5                   10                  15

Arg Phe

<210> SEQ ID NO 74
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)A

<400> SEQUENCE: 74

Arg Arg Met Lys Trp Lys Lys Tyr Ala Asn Trp Asn Gly Phe Gly Trp
1               5                   10                  15

Arg Phe

<210> SEQ ID NO 75
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)A
<220> FEATURE:
<221> NAME/KEY: SITE
<222> LOCATION: 13
<223> OTHER INFORMATION: (D)S
<220> FEATURE:
<221> NAME/KEY: SITE
<222> LOCATION: 16
<223> OTHER INFORMATION: (D)W

<400> SEQUENCE: 75

Arg Arg Met Lys Trp Lys Lys Tyr Ala Asn Trp Asn Ser Phe Gly Trp
1               5                   10                  15

Arg Phe

<210> SEQ ID NO 76
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)A
<220> FEATURE:
<221> NAME/KEY: SITE
<222> LOCATION: 16
<223> OTHER INFORMATION: (D)L

<400> SEQUENCE: 76

Arg Arg Met Lys Trp Lys Lys Tyr Ala Asn Trp Asn Gly Phe Gly Leu
1               5                   10                  15

Arg Phe

<210> SEQ ID NO 77
<211> LENGTH: 18
<212> TYPE: PRT
<213> ORGANISM: Artificial Sequence
<220> FEATURE:
<223> OTHER INFORMATION: Kisspeptin variant sequence with N terminal
      antennapedia sequence
<220> FEATURE:
<221> NAME/KEY: SITE
<222> LOCATION: 9
<223> OTHER INFORMATION: (D)A
<220> FEATURE:
<221> NAME/KEY: SITE
<222> LOCATION: 16
<223> OTHER INFORMATION: (D)W

<400> SEQUENCE: 77

Arg Arg Met Lys Trp Lys Lys Tyr Ala Asn Trp Asn Gly Phe Gly Trp
1               5                   10                  15

Arg Phe

```
<210> SEQ ID NO 78
<211> LENGTH: 43
<212> TYPE: PRT
<213> ORGANISM: Artificial Sequence
<220> FEATURE:
<223> OTHER INFORMATION: Kisspeptin sequence

<400> SEQUENCE: 78

Gly Thr Ser Leu Ser Pro Pro Glu Ser Ser Gly Ser Arg Gln Gln
 1               5                  10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro
        35                  40

<210> SEQ ID NO 79
<211> LENGTH: 10
<212> TYPE: PRT
<213> ORGANISM: Artificial Sequence
<220> FEATURE:
<223> OTHER INFORMATION: Consensus peptide sequence
<220> FEATURE:
<221> NAME/KEY: SITE
<222> LOCATION: 1
<223> OTHER INFORMATION: Xaa = (D)Y or (D)A
<220> FEATURE:
<221> NAME/KEY: SITE
<222> LOCATION: 2
<223> OTHER INFORMATION: Xaa = N or (D)A or (D)W
<220> FEATURE:
<221> NAME/KEY: SITE
<222> LOCATION: 3
<223> OTHER INFORMATION: Xaa = W or (D)W or (D)A
<220> FEATURE:
<221> NAME/KEY: SITE
<222> LOCATION: 8
<223> OTHER INFORMATION: Xaa = (D)L or (D)F or (D)W

<400> SEQUENCE: 79

Xaa Xaa Xaa Asn Gly Phe Gly Xaa Arg Phe
 1               5                  10

<210> SEQ ID NO 80
<211> LENGTH: 6
<212> TYPE: PRT
<213> ORGANISM: Artificial Sequence
<220> FEATURE:
<223> OTHER INFORMATION: Artificially synthesized
      Kisspeptin analog

<400> SEQUENCE: 80

Ser Phe Gly Leu Arg Phe
 1               5

<210> SEQ ID NO 81
<211> LENGTH: 6
<212> TYPE: PRT
<213> ORGANISM: Artificial Sequence
<220> FEATURE:
<223> OTHER INFORMATION: Artificially synthesized
      Kisspeptin analog

<400> SEQUENCE: 81

Ser Phe Gly Leu Arg Trp
 1               5

<210> SEQ ID NO 82
<211> LENGTH: 10
<212> TYPE: PRT
```

```
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 6
<223> OTHER INFORMATION: (D)F

<400> SEQUENCE: 82

Tyr Asn Trp Asn Gly Phe Gly Leu Arg Phe
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 6
<223> OTHER INFORMATION: (D)L
<220> FEATURE:
<221> NAME/KEY: SITE
<222> LOCATION: 8
<223> OTHER INFORMATION: (D)L

<400> SEQUENCE: 83

Tyr Asn Trp Asn Gly Leu Gly Leu Arg Phe
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)Y

<400> SEQUENCE: 84

Tyr Asn Trp Asn Gly Phe Gly Trp Arg Phe
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)Y
<220> FEATURE:
<221> NAME/KEY: SITE
<222> LOCATION: 8
<223> OTHER INFORMATION: (D)W

<400> SEQUENCE: 85

Tyr Asn Trp Asn Ser Phe Gly Trp Arg Phe
1               5                   10

<210> SEQ ID NO 86
<211> LENGTH: 10
```

```
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)Y

<400> SEQUENCE: 86

Tyr Asn Trp Asn Ser Phe Gly Trp Arg Phe
 1               5                  10

<210> SEQ ID NO 87
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)Y
<220> FEATURE:
<221> NAME/KEY: SITE
<222> LOCATION: 2
<223> OTHER INFORMATION: (D)N

<400> SEQUENCE: 87

Tyr Asn Trp Asn Gly Phe Gly Trp Arg Phe
 1               5                  10

<210> SEQ ID NO 88
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)Y
<220> FEATURE:
<221> NAME/KEY: SITE
<222> LOCATION: 2
<223> OTHER INFORMATION: (D)N
<220> FEATURE:
<221> NAME/KEY: SITE
<222> LOCATION: 8
<223> OTHER INFORMATION: (D)W

<400> SEQUENCE: 88

Tyr Asn Trp Asn Ser Phe Gly Trp Arg Phe
 1               5                  10

<210> SEQ ID NO 89
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)Y
<220> FEATURE:
<221> NAME/KEY: SITE
<222> LOCATION: 2
<223> OTHER INFORMATION: (D)N
```

```
<220> FEATURE:
<221> NAME/KEY: SITE
<222> LOCATION: 8
<223> OTHER INFORMATION: (D)W

<400> SEQUENCE: 89

Tyr Asn Trp Asn Gly Phe Gly Trp Arg Phe
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)A
<220> FEATURE:
<221> NAME/KEY: SITE
<222> LOCATION: 8
<223> OTHER INFORMATION: (D)W

<400> SEQUENCE: 90

Ala Asn Trp Asn Pro Phe Gly Trp Arg Phe
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)A
<220> FEATURE:
<221> NAME/KEY: SITE
<222> LOCATION: 5
<223> OTHER INFORMATION: (D)P
<220> FEATURE:
<221> NAME/KEY: SITE
<222> LOCATION: 8
<223> OTHER INFORMATION: (D)W

<400> SEQUENCE: 91

Ala Asn Trp Asn Pro Phe Gly Trp Arg Phe
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)A
<220> FEATURE:
<221> NAME/KEY: SITE
<222> LOCATION: 5
<223> OTHER INFORMATION: (D)A

<400> SEQUENCE: 92

Ala Asn Trp Asn Ala Phe Gly Leu Arg Phe
1               5                   10
```

```
<210> SEQ ID NO 93
<211> LENGTH: 10
<212> TYPE: PRT
<213> ORGANISM: Artificial Sequence
<220> FEATURE:
<223> OTHER INFORMATION: Artificially synthesized
      Kisspeptin analog
<220> FEATURE:
<221> NAME/KEY: SITE
<222> LOCATION: 1
<223> OTHER INFORMATION: (D)A
<220> FEATURE:
<221> NAME/KEY: SITE
<222> LOCATION: 9
<223> OTHER INFORMATION: (D)R

<400> SEQUENCE: 93

Ala Asn Trp Asn Gly Phe Gly Leu Arg Phe
1               5                   10
```

COMPOUND, USE AND METHOD

RELATED APPLICATIONS

This application is the U.S. National Stage of International Application No. PCT/GB2008/003426, filed Oct. 8, 2008, published in English, and claims priority under 35 U.S.C. §119 or 365 to Great Britain Application No. 0719592.8, filed Oct. 8, 2008, and claims the benefit of U.S. Application No. 60/978,179, filed Oct. 8, 2007. The entire teachings of the above applications are incorporated herein by reference.

The invention relates to kisspeptin antagonists and their use for treating a condition induced and/or worsened by kisspeptin activity in an individual. In addition, the invention relates to a method for identifying kisspeptin antagonists.

RFamides are a group of peptide hormones that have a common Arg-Phe-NH$_2$ motif at their C-terminus and all bind to G protein-coupled receptors. RFamides have been shown to be involved in many processes throughout the body including inflammatory responses, control of food intake and development. One major area where RFamides play a role is reproduction, involving two RFamides: Gonadotrophin inhibitory Hormone (GnIH) and Kisspeptin.

The KiSS-1 gene is located on human Chromosome 1q32 and consists of four exons, two non-translated and two partially translated to give rise to a 145 amino acid (aa) peptide [1]. The precursor peptide is cleaved to 54 amino acids in length, which can be further truncated to 14, 13 or 10 amino acids; these collective truncations are known as the Kisspeptins, and are highly conserved within mammals. These peptides are now known to be the ligands for the orphan G protein-coupled receptor (GPCRs) known as GPR54 in rat and AXOR12 in humans [2-4]. The 10aa peptide, YNWNS-FGLRF-NH$_2$ (SEQ ID NO:1) is sufficient to activate the receptor.

The GPR54 receptor has a 396aa open reading frame and is related to the galanin receptor family, though it does not bind galanin. Rat GPR54 is highly conserved among mammals with an 81% homology to the human receptor and an 85% homology to the mouse [2, 4, 5]. Both the receptor and ligand have been highly characterised within the brain and peripheral tissues, where GPR54 and KiSS-1 have been located in the hypothalamus, aorta, ovary, prostate and placenta with GPR54 also being expressed in the pituitary [2, 4, 6, 7].

Considering the locations of receptor and ligand expression, a role for them in reproduction was hypothesised, and confirmed when it was shown that loss of function heterozygous and homozygous mutations within GPR54 cause idiopathic Hypogonoadotropic Hypogonadism (iHH), where patients exhibit delayed or failed puberty, characterised by low or absent plasma luteinising hormone (LH) pulsatility [8-13]. This was also observed in GPR54−/− mice, which had small testis/ovaries, small external genitalia and seminiferous tubules, Leydig cells and uterine horns that were hypoplastic, very similar to that seen in iHH humans [14]. This then eluded to the hypothesis that KiSS-1 and GPR54 played a role in the control of puberty and in particular, its timing. Since then, KiSS-1 mRNA level has been found to be higher in pubertal compared to juvenile monkeys [15]. In mice, there are no KiSS-1 neurons at day 10 (d10), they begin to appear at day 25 and increase to adult levels around day 45 in males and day 61 in females in the Anterioventral Paraventricular nucleus (AVPV). This coincides with the timing of puberty in these animals [16]. However, GPR54 mRNA levels remain constant throughout postnatal development and therefore kisspeptin infusion can stimulate LH release at all stages. Kisspeptin is therefore seen as the main regulator of GnRH secretion in the initiation of puberty [17].

The expression of Kisspeptin and GPR54 in the hypothalamus gave rise to the hypothesis that Kisspeptins may be involved in the regulation of the Hypothalmic-Pituitary-Gonadal (HPG) axis. This hypothesis was confirmed when Kisspeptin was shown to rapidly increase plasma Luteinising Hormone (LH), Follicle Stimulating Hormone (FSH) and Testosterone in the male rat and humans in a dose-dependant manner, with a 10-fold more potent effect on LH over FSH [18-20]. It has been further shown that this increase in gonadotrophins can be abolished by administering a Gonadotrophin Releasing Hormone Receptor (GnRHR) antagonist. This suggests that Kisspeptin works at the level of the hypothalamus to stimulate GnRH release [15]. This was further established when it was found that GnRH neurons in the Median Eminence of the hypothalamus possess the GPR54 receptor and that 90% of KiSS-1 neuron fibres are co-localised with GnRH-immunoreactive neurons [21, 22]. Also GT1-7 hypothalamic cells express KiSS-1 and GPR54 mRNA which is increased in response to estradiol and Kisspeptin stimulates GnRH release from these cells after 24 hrs [23]. The above data also suggests that Kisspeptin does not work at the level of the pituitary, though actions directly at the pituitary level have not been ruled out. Other groups have also shown that Kisspeptin is expressed in the pituitary in gonadotropes and somatotropes and that Kisspeptin can directly stimulate release of LH and growth hormone [24, 25]

KiSS-1 neurons have been localised to the Arcuate nucleus (ARC) and AVPV of the hypothalamus in rodents and primates. However in sheep and rats, they are only found in the ARC [16, 26, 27]. It has now been established that the ARC is involved in negative steroid regulation and AVPV in the positive feedback control of gonadotrophin release. This was first noted following the castration of male mice, when it was seen that in the ARC, KiSS-1 cell numbers and mRNA expression levels increased and that estrogen replacement lowered this to normal levels, whereas in the AVPV, KiSS-1 cell numbers decreased and estrogen administration increased this to back to natural levels [26]. KiSS-1 cell bodies are now proven to express estrogen receptor α (ERα) and the progesterone receptor, signifying a role for KiSS-1 in steroid feedback loops [27, 28]. This suggests that the ARC is under negative control to regulate the LH pulses and that AVPV is under positive control possibly to stimulate the LH surge and induction of ovulation. This has been demonstrated by Kisspeptin antiserum inhibition of LH surge in rats even in the presence of high estrogen and as there are 10× more KiSS-1 neurons in the AVPV of female compared to male mice. This steroid control is operative over the estrus cycle as KiSS-1-positive cell numbers in AVPV are highest at proestrus and lowest at diestrus with the opposite situation in the ARC [16, 29]. In sheep, both positive and negative feedback act at the ARC to give the same response as in other mammals with the caudal region facilitating the LH surge. As well as being under steroid control, KiSS-1 is also regulated by photoperiod via melatonin, and KiSS-1 neurons possess the Mel1c receptor on their cell bodies. Also female Siberian hamsters, held in short day lengths had a reduced response to exogenous Kisspeptin compared to those held in long day conditions [30-33]. Leptin also seems to play an influential role, as severely fasted rodents have decrease KiSS-1 mRNA, GnRH, LH and FSH as well as delayed puberty [34, 35].

Kisspeptin is also found outside the HPG axis in peripheral tissues such as the cardiovascular system, were Kisspeptin-10/13 have been shown to act as vasoconstrictors of aortic smooth muscle [7, 36]. GPR54 is also highly expressed in the Central Nervous System (CNS), in the hippocampus region of the brain, were it has been shown to reversibly enhance the synaptic transmission in the hippocampul dentate granule cells through mechanisms involving MAP kinases, which appear to be regulated via calcium-activated kinases and tyrosine kinases [37]. KiSS-1 and GPR54 mRNA have also been located within the rat ovary where expression is again correlated to the estrus cycle. In the ovary, KiSS-1 is located within the ovarian surface epithelium, interstitial glands, corpus luteum and in follicles, being present within the theca cells until proestrus when expression shifts to the granulosa layers [6]. Recently, KiSS mRNA was detected in the oviduct of the uterus and has been hypothesised to be involved in the prevention of ectopic pregnancy [38]. However, the highest levels of KiSS-1 & GPR54 are in the placenta.

In the placenta, KiSS-1 and GPR54 are located within the syncytiotrophoblast cells in mice [39] and humans [40]; and within giant cells in rats [41]. GPR54 is also located in the extravillious trophoblast cells, suggesting possible paracrine actions [42]. Both ligand and receptor are present at high levels in the first trimester but only KiSS-1 is present at term in humans and both are absent by E18.5 in rats. This corresponds with trophoblast invasion and KiSS-1 has been hypothesized as an inhibitor of this due to its anti-metastatic properties [39, 41].

Kisspeptin is also known to be an anti-metastatic factor in many cancer tissues, such as pancreatic, thyroid and heptocellular carcinomas [43-45]. Different mechanisms for this function have been hypothesised including antagonism of stromal cell-derived factor-1 (SDF-1) to inhibit the metastatic properties of its chemokine receptor CXCR4 and the up regulation of modulatory calcineurin-interactin protein-1 (MCIP-1), a chemokine capable of inhibiting the calcinuerin signalling pathway [46, 47]. Another hypothesis is that Kisspeptin is regulated by Specificity Protein 1 (SP1) and its co-activator DRIP130 which is located on chromosome region 6q16.3q23. When Loss of hetrozygosity (LOH) occurs at this region KiSS-1 is frequently lost from tumours and this allows metastasis to occur. This can be rescued by SP1 and DRIP130 which inhibit invasion and migration [48, 49].

This inhibition has also been shown in cultured cells and was used as an output to investigate signalling pathways used by Kisspeptin. In chinese hamster ovary (CHO) cells, Kisspeptin-10 (Kp10) can inhibit chemotaxis, migration, colony formation and growth and can cause cell rounding. Kp-10 can also cause focal adhesion and stress fibre formation via the phosphorylation of focal adhesion kinase (FAK) and paxillin [3, 50, 51]. Kisspeptin and GPR54 have been shown to increase Inositol-3-phosphate, intracellular calcium and pERK, showing GPR54 activates the $G_{q/11}$ signalling pathway [4]. This does not entirely concur with the anti-metastatic properties as this pathway usually stimulates growth and migration. It has therefore been suggested that Kisspeptin may activate other pathways such as the Rho and Rac/Cdc42 pathways [5, 51].

Against this background, the inventors have surprisingly found that kisspeptin antagonists may be useful in treating a condition induced and/or worsened by kisspeptin activity in an individual.

Accordingly, in a first aspect the invention provides the use of an antagonist of kisspeptin in the manufacture of a medicament for the treatment of a condition induced and/or worsened by kisspeptin activity in an individual. In second aspect, the invention provides an antagonist of kisspeptin for use in the treatment of a condition induced and/or worsened by kisspeptin activity in an individual.

In particular, antagonists of the GPR54 receptor have been found to be useful to manipulate gonadotropin and sex steroid-related disorders via inhibiting GnRH release at the hypothalamus. Kisspeptin antagonists are therefore an important discovery as they could potentially replace GnRH agonists and antagonists for gonadotropin inhibition and may be more rapid and complete in their actions.

GnRH analogues are used in an inhibitory modality to inhibit gonadotropin and sex hormones, and they have since acquired extensive therapeutic application in treating hormone-dependent diseases (such as prostate, breast and ovarian cancers), in in vitro fertilisation for inducing ovulation and as new-generation contraceptives.

Accordingly, as kisspeptin is the primary stimulator of GnRH (for example, it is known that mutations in the kisspeptin receptor, GPR54, cause infertility) the present inventors have discovered that kisspeptin antagonists would have a similar range of applications as GnRH antagonists; furthermore, because kisspeptin operates upstream of the GnRH neurone, kisspeptin antagonists would be expected to be more rapid and effective in its action than GnRH-based therapies.

By "kisspeptin activity in an individual" we include any in vitro and/or in vivo property, activity or characteristic of kisspeptin. Thus, by "an antagonist of kisspeptin" we include the meaning of a molecule that is capable of preventing and/or reducing any in vitro and/or in vivo property, activity or characteristic of kisspeptin. For example, a kisspeptin antagonist may prevent and/or reduce the ability of kisspeptin to physically associate with, or bind to, the kisspeptin receptor or other cell components.

Thus, the molecules and antagonists of the invention may be capable of reversibly or irreversibly binding to the kisspeptin receptor and/or selectively binding to the kisspeptin receptor. By "selectively binding" we include the ability of the molecules and antagonists of the invention to bind at least 10-fold more strongly to the kisspeptin receptor than to another polypeptide; preferably at least 50-fold more strongly and more preferably at least 100-fold more strongly. Preferably, the molecules and antagonists of the invention bind to the kisspeptin receptor under physiological conditions, for example, in vivo. Methods for measuring the binding or association of a peptide with its ligand or receptor (either in vivo or in vitro) are well-known to those skilled in the arts of biochemistry and cell biology.

For example, as shown in the accompanying Examples, the antagonists of the invention may be competitive antagonists of kisspeptin which bind to, but do not activate, the kisspeptin cognate receptor (such as GPR54).

A kisspeptin antagonist may also prevent and/or reduce the ability of kisspeptin to stimulate particular cellular behaviour, such as the kisspeptin-mediated stimulation of inositol phosphate production in a cell (such as in transformed or primary cell lines, like CHO, HEK, COS, the GnRH GTI neuronal cell-line, and normal trophoblasts and cell lines such as JEG). Biochemical assays for the cellular measurement of inositol phosphate production are well known in the art.

In a particularly preferred aspect, the antagonist is a peptide analogue of the kisspeptin peptide. The structure/activity relationship (SAR) for peptide analogues of the kisspeptin peptides has received relatively sparse attention and, until now, focused entirely on agonism [52, 53]. The amino acid sequence of kisspeptin (also known as kisspeptin 1-54) is:

(SEQ ID NO: 2)
GTSLSPPPESSGSRQQPGLSAPHSRQIPAPQGAVLVQREKDLPNYNWNSF

GLRF.NH$_2$

Thus, in a third aspect, the invention provides the use of a peptide molecule comprising or consisting of the sequence:

wherein:
$X^1$ is F or A or any D-amino-acid residue;
$X^2$ is L or A or any D-amino-acid residue;
$X^3$ is F or W; and
wherein the C-terminal amino acid residue of the peptide molecule contains group z which removes the charge on that residue;
or a fragment or variant thereof;
and wherein the peptide sequence is not:

for the treatment of a condition induced and/or worsened by kisspeptin activity in a patient or in the manufacture of a medicament for the treatment of a condition induced and/or worsened by kisspeptin activity in a patient.

Preferably, where the C-terminal amino acid residue of the peptide molecules of the invention contains group z, the negative charge on that C-terminal residue is removed.

It will be appreciated that the peptide molecules of the invention described herein are defined using the conventional one-letter code used to denote amino acids. The term "amino acid" includes any of a group of water-soluble organic compounds that possess both a carboxyl (—COOH) and an amino (—NH$_2$) group attached to the α-carbon atom. Amino acids can be represented by the general formula R—CH(NH$_2$)COOH; the R group is hydrogen or an organic group and determines the properties of any particular amino acid. The tetrahedral array of four different groups about the α-carbon atom confers optical activity on amino acids. The two-mirror image forms are called an L-isomer and a D-isomer. Typically, only L-amino acids are constituents of proteins (such as eukaryotic proteins).

Unless otherwise stated, the peptide molecules of the invention contain L-amino acids. When present in the peptide molecules of the invention, D-amino acids are referred to with the prefix "(D)" prior to the usual one-letter amino acid code.

Where stated, the molecules of the invention can comprise or consist of peptide sequences having "any D-amino acid" at a given position. By "any D-amino acid" we include any natural or unnatural (for example, chemically-modified) D-amino acid in that position in the sequence. Examples of natural D-amino acids are: D-alanine; D-aspartic acid; D-cysteine; D-glutamic acid; D-phenylalanine; D-glycine; D-histidine; D-isoleucine; D-lysine; D-leucine; D-methionine; D-asparagine; D-proline; D-glutamine; D-arginine; D-serine; D-threonine; D-valine; D-tryptophan; D-tyrosine.

Examples of unnatural D-amino acids are: napthylalanine; D-pyridyl alanine; D-tertiarybutyl serine; D-ornithine; D-epsilon amino lysine; D-homoarginine; D-α methyl leucine along with halide substitutions (e.g. F) of protons in these and other unnatural amino acids.

Through the formation of peptide bonds, amino acids join together to form short chains (peptides) or longer chains (polypeptides). It is well known that proteins and/or peptides are composed of varying proportions of approximately 20 commonly-occurring amino acids, the sequence of which determines the shape, properties and biological role of the protein and/or peptide. Amino acid residues within such peptide or polypeptide chains are conventionally referred to by their numbered position in the chain, with the first position (i.e. position 1) assigned to the amino acid at the N-terminal end of the chain.

Peptide sequences of the molecules of the invention may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

The peptide sequence of the molecules of the invention may also be synthesised using liquid phase methodology, which is well known those skilled in the art of chemistry and biochemistry.

The peptide sequence of the molecules of the invention may comprise or consist of peptidomimetic compounds. The term "peptidomimetic" refers to a compound that mimics the conformation and desirable features of a particular peptide as a therapeutic agent, but that avoids the undesirable features.

For example, morphine is a compound which can be orally administered, and which is a peptidomimetic of the peptides enkephalin and/or endorphin.

In general, therapeutic applications involving peptides are limited due to lack of oral bioavailability and to proteolytic degradation, and are typically administered by injection. Typically, for example, peptides are rapidly degraded in vivo by exo- and endopeptidases, resulting in generally very short biological half-lives. Another deficiency of peptides as potential therapeutic agents is their lack of bioavailability via oral administration. Degradation of the peptides by proteolytic enzymes in the gastrointestinal tract is likely to be an important contributing factor. The problem is, however, more complicated because it has been recognised that even small, cyclic peptides or peptides comprising D-amino acids which are not subject to rapid metabolite inactivation nevertheless exhibit poor oral bioavailability. This is likely to be due to poor transport across the intestinal membrane and rapid clearance from the blood by hepatic extraction and subsequent excretion into the intestine. These observations suggest that multiple amide bonds may interfere with oral bioavailability. It is thought that the peptide bonds linking the amino acid residues in the peptide chain may break apart or be cleaved when the peptide drug is orally administered.

There are a number of different approaches to the design and synthesis of peptidomimetics. In one approach, such as disclosed by Sherman and Spatola, *J. Am. Chem. Soc.*, 112: 433 (1990), one or more amide bonds have been replaced in an essentially isoteric manner by a variety of chemical functional groups. This stepwise approach has met with some success in that active analogues have been obtained. In some instances, these analogues have been shown to possess longer biological half-lives than their naturally-occurring counterparts. Nevertheless, this approach has limitations. Successful replacement of more than one amide bond has been rare. Consequently, the resulting analogues have remained susceptible to enzymatic inactivation elsewhere in the molecule. When replacing the peptide bond it is preferred that the new linker moiety has substantially the same charge distribution and substantially the same planarity as a peptide bond.

Retro-inverso peptidomimetics, in which the peptide bonds are reversed, can be synthesised by methods known in the art, for example such as those described in Mézière et al (1997) *J. Immunol.* 159 3230-3237. This approach involves making pseudopeptides containing changes involving the backbone, and not the orientation of side chains. Retro-inverse peptides, which contain NH—CO bonds instead of CO—NH peptide bonds, are much more resistant to proteolysis. Retro-inverso peptidomimetics of certain GnRH peptides have been synthesised previously (Fromme, 2003, *Endocrinology*, 144:3262-9).

In another approach, a variety of un-coded or modified amino acids such as D-amino acids and N-methyl amino acids have been used to modify mammalian peptides. Alternatively, a presumed bioactive conformation has been stabilised by a covalent modification, such as cyclisation or by incorporation of γ-lactam or other types of bridges. See, for example, Veber et al, *Proc. Natl. Acad. Sci. USA*, 75:2636 (1978) and Thursell et al, *Biochem. Biophys. Res. Comm.*, 111:166 (1983).

A common theme among many of the synthetic strategies has been the introduction of some cyclic moiety into a peptide-based framework. The cyclic moiety restricts the conformational space of the peptide structure and this frequently results in an increased affinity of the peptide for a particular biological receptor. An added advantage of this strategy is that the introduction of a cyclic moiety into a peptide may also result in the peptide having a diminished sensitivity to cellular peptidases.

One approach to the synthesis of cyclic stabilised peptidomimetics is ring closing metathesis (RCM). This method involves steps of synthesising a peptide precursor and contacting it with a RCM catalyst to yield a conformationally-restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986), has been to design peptide mimics through the application of the transition state analogue concept in enzyme inhibitor design. For example, it is known that the secondary alcohol of staline mimics the tetrahedral transition state of the scissile amide bond of the pepsin substrate. However, the transition state analogue concept has no apparent relevance to hormone agonist/antagonist design.

For the avoidance of doubt, it is not necessary that the amino acid residues in the peptide sequence are joined by standard peptide bonds. For example, as discussed above, the amino acid residues may be linked by reverse peptide bonds, or they may be joined together by other bonds which mimic the bond distance and spatial orientation of a standard peptide bond.

Peptide sequences of the agents of the invention may be purified following synthesis using methods known in the art, such as HPLC and chromatography By "a molecule" we include salts (e.g. organic or inorganic acid addition salts), esters and solvates of the molecules comprising or consisting of the peptide sequences of the invention. It will be appreciated that the term further includes derivatives that have the same biological function and/or activity as the relevant molecule. Moreover, for the purposes of this invention, the term also includes prodrugs of the relevant molecule (for example, esters). The term "prodrug" includes any composition of matter that, following oral or parenteral administration, is metabolised in vivo to form the relevant agent in an experimentally-detectable amount, and within a predetermined time of dosing.

The molecules of the invention may further consist of or comprise one or more moiety which is capable of targeting and/or localising the molecule of the invention to a target cell (such as a cancer cell) and/or to increase the half-life (t½) of the molecule of the invention. Such moieties can therefore increase efficacy of the molecule of the invention. Preferably, one or more moiety may be included in a molecule of the invention when the molecule comprises or consists of a peptide sequence comprising or consisting of a D-amino acid as those amino acid residues are particularly amenable to modification.

The molecules of the invention may further consist of or comprise one or more moiety which is capable of targeting and/or localising the molecule of the invention to a target cell (such as a cancer cell) and/or to increase the half-life (t½) of the molecule of the invention. Such moieties can therefore increase efficacy of the molecules of the invention. Preferably, one or more moiety may be included in a molecule of the invention when the agent comprises or consists of a peptide sequence comprising a D-amino acid, as those amino acid residues are particularly amenable to modification.

Preferably, the one or more moiety is a steroid hormone molecule (including, for example, progesterone, testosterone, estradiol or cortisol) and is conjugated to the side chain of a D-amino acid. Steroid hormone molecules are capable of binding to plasma proteins and have been shown to reduce the metabolic clearance of peptides (Ratcliffe et al., 2006, *Endocrinology*, 147:571-9). For example, GnRH peptides conjugated to steroid hormones are described in WO2004/08725, incorporated herein by reference. Alternatively, the one or more moiety is a vitamin, such as vitamin $B_{12}$ or vitamin D, and is conjugated to the $NH_2$ terminus of the kisspeptin analogues or a suitable side chain of a natural or D-amino acid. Vitamins have been shown to improve the oral bioavailability of peptides (Russell-Jones et al., 1995, Bioconjug. Chem., 6:34-42; Russell-Jones et al., 1995, Bioconjug. Chem., 6:459-465).

Preferably, the ability of the molecule of the invention to act as an antagonist of kisspeptin is not affected and/or significantly affected by the one or more moiety.

Preferably, the invention provides a use wherein the peptide sequence is not:

```
F-G-A-R-W;          (SEQ ID NO: 7)

F-G-L-(D)R-W;       (SEQ ID NO: 8)

F-G-(D)L-R-W;       (SEQ ID NO 9)
or (D)F-G-L-R-W.       (SEQ ID NO: 10)
```

Conveniently, the invention provides a use wherein $X^1$ is (D)F. Preferably, $X^2$ is a D-amino-acid residue selected from the group consisting of: (D)F, (D)L and (D)W.

More preferably, the peptide sequence is selected from the group consisting of:

```
(D)F-W-L-R-W;       (SEQ ID NO: 11)
or

F-G-(D)W-R-F.       (SEQ ID NO: 12)
```

In one embodiment, the invention provides a use wherein the N-terminal residue contains group y which removes the charge on that residue. Typically, $X^1$ contains group y which removes the charge on that residue.

The group y may be selected from the group consisting of: an acetyl group (represented throughout this application as "ac"); a trifluoroacetyl group; a cyclised amino acid; or a synthetic amino acid lacking a charge at the N-terminus (such as an amino acid with an amino group that has been modified by the addition of a further compound (such as pyroglutamic acid) or chemical group, for example an alkyl group (e.g. formyl, acetyl, propyl, butyl and longer alkyl groups).

Preferably, the invention provides a use wherein $X^3$ contains group z which removes the charge on that residue.

In one embodiment, the invention provides a use wherein the sequence is selected from the group consisting of:

```
I)   ac.F-G-(D)F-R-W.z;    (SEQ ID NO: 13)

II)  ac.F-G-(D)L-R-W.z;    (SEQ ID NO: 14)

III) ac.F-G-L-(D)R-W.z;    (SEQ ID NO: 15)

IV)  ac.F-G-A-R-W.z;       (SEQ ID NO: 16)

V)   ac.A-G-L-R-W.z;       (SEQ ID NO: 17)

VI)  ac.(D)F-W-L-R-W.z;    (SEQ ID NO: 18)
or

VII) ac.F-G-(D)W-R-F.z.    (SEQ ID NO: 19)
```

In one embodiment, the acetyl group on the N-terminal residue of any of peptides (I) to (VI), above, (which is represented above and throughout this application as "ac") is replaced with a group y which removes the charge on that residue, and is preferably selected from the group consisting of: an acetyl group; a trifluoroacetyl group; a cyclised amino acid; or a synthetic amino acid lacking a charge at the N-terminus.

In one embodiment, the use according to the third aspect of the invention involves a molecule in which the peptide sequence comprises additional amino acid residues, or peptides, at the N- and/or C-terminus of the peptide sequence of the third aspect of the invention, thereby incorporating the peptide sequence into a larger polypeptide or protein molecule. Thus, the peptide sequence of the third aspect of the invention may comprise at the N- and/or C-terminus between 0 and 10 amino acids; or between 10 and 20 amino acids; or between 20 and 30 amino acids; or between 30 and 40 amino acids; or between 40 and 50 amino acids; or between 50 and 60 amino acids; or between 60 and 70 amino acids; or between 70 and 80 amino acids; or between 80 and 90 amino acids; or between 90 and 100 amino acids; or more than 100 amino acids.

In a preferred embodiment, the use according to the third aspect of the invention involves a molecule comprising or consisting of the additional peptide sequence R-R-M-K-W-K-K-Y (SEQ ID NO:20) or ac.R-R-M-K-W-K-K-Y (SEQ ID NO:20) at the N-terminus of the peptide sequence.

The R-R-M-K-W-K-K-Y (SEQ ID NO:20) sequence is a heptapeptide sequence from Antennapedia, which facilitates and/or improves intracellular delivery of peptide sequences, thereby improving the therapeutic use of the peptides of the invention. The Antennapedia heptapeptide is described in Fisher et al., 2003, *J. Peptide Res.*, 55:163-72; and Wang et al., 2006, *Bioorganic and Medicinal Chemistry Letters*, 16:2628-2631.

Accordingly, the peptide of the invention may comprise or consist of the sequence:

```
R-R-M-K-W-K-K-Y-F-G-(D)F-R-W.z;    (SEQ ID NO: 21)

R-R-M-K-W-K-K-Y-F-G-(D)L-R-W.z;    (SEQ ID NO: 22)

R-R-M-K-W-K-K-Y-F-G-L-(D)R-W.z;    (SEQ ID NO: 23)

R-R-M-K-W-K-K-Y-F-G-A-R-W.z;       (SEQ ID NO: 24)

R-R-M-K-W-K-K-Y-A-G-L-R-W.z;       (SEQ ID NO: 25)

R-R-M-K-W-K-K-Y-(D)F-W-L-R-W.z;    (SEQ ID NO: 26)
or

R-R-M-K-W-K-K-Y-F-G-(D)W-R-F.z.    (SEQ ID NO: 27)
```

Optionally, the N-terminal residue may comprise group y at the N-terminus, as defined above, and is preferably acetyl (ac).

Preferably, the peptide sequence of the third aspect of the invention is incorporated within some or all of the sequence of the full-length kisspeptin peptide. More preferably, the N-terminus of the peptide sequence of the third aspect of the invention can be extended to any length incorporating the peptide sequence of kisspeptin 1-54 (i.e. amino acid residues 1 to 54 of the kisspeptin sequence) and/or the peptide sequence of kisspeptin 1-45 (i.e. amino acid residues 1 to 45 of the kisspeptin sequence). For example, the peptide sequence of the third aspect of the invention may have the following sequence at its N-terminus:

```
                                              (SEQ ID NO: 28)
GTSLSPPPESSGSRQQPGLSAPHSRQIPAPQGAVLVQREKDLPNYNWNS
```

Alternatively, the peptide sequence of the third aspect of the invention can be incorporated within a protein, such as an albumin and/or immunoglobulin protein. Incorporation into such molecules is thought to increase half-life and decrease the metabolic clearance within an individual of the peptide molecules of the invention.

In a fourth aspect, the invention provides the use of a peptide molecule comprising or consisting of the sequence:

```
X^A-X^B-X^C-N-X^D-X^E-G-X^F-R-F     (SEQ ID NO: 29)
``` wherein:
X$^A$ is Y or any D-amino-acid residue;
X$^B$ is N or any D-amino acid residue;
X$^C$ is W or any D-amino acid residue;
X$^D$ is G or S or any D-amino acid residue;
X$^E$ is F or (D)W or (D)L;
X$^F$ is W or L or any D-amino acid residue; and
wherein the C-terminal amino acid residue of the peptide molecule contains group z which removes the charge on that residue;
or a fragment or variant thereof;
and wherein the peptide sequence is not:

```
Y-N-W-N-S-F-G-L-R-F;               (SEQ ID NO: 30)

(D)Y-(D)N-W-N-S-F-G-W-R-F;         (SEQ ID NO: 31)

(D)Y-(D)N-W-N-G-F-G-W-R-F;         (SEQ ID NO: 32)

(D)Y-(D)N-W-N-S-F-G-(D)W-R-F;      (SEQ ID NO: 33)
or (D)Y-(D)N-W-N-G-F-G-(D)W-R-F.      (SEQ ID NO: 34)
``` for the treatment of a condition induced and/or worsened by kisspeptin activity in a patient or in the manufacture of a medicament for the treatment of a condition induced and/or worsened by kisspeptin activity in a patient.

Preferably, X$^A$ is a D-amino-acid residue selected from the group consisting of: (D)F and (D)Y and (D)A. Typically, X$^B$ is a D-amino-acid residue selected from the group consisting of: (D)A and (D)N. In one aspect, when one of X$^A$ or X$^B$ is (D)Y, the other is not (D)N. In another aspect, X$^A$ and X$^B$ are not both a D-amino acid residue. Preferably, when X$^F$ is (D)W, X$^A$ is (D)F.

Preferably, the invention provides a use wherein X$^C$ is a D-amino-acid residue selected from the group consisting of: (D)A and (D)W.

In one embodiment, X$^D$ is a D-amino-acid residue selected from the group consisting of: (D)A and (D)W. Preferably, when X$^D$ is S, X$^F$ is (D)W and/or X$^A$ is not (D)Y and more preferably, when X$^D$ is S, X$^F$ is (D)W and/or X$^A$ is (D)A.

Preferably, X$^F$ is a D-amino-acid residue selected from the group consisting of: (D)L and (D)W.

In one embodiment, when X$^E$ and X$^F$ are both (D)W, X$^A$ is not (D)Y. Preferably, when X$^E$ and X$^F$ are both (D)W, X$^A$ is (D)A.

Typically, the invention provides a use wherein the N-terminal residue contains group y which removes the charge on that residue. Preferably, X$^1$ contains group y which removes the charge on that residue. The group y is selected from the group consisting of: an acetyl group; a trifluoroacetyl group; a cyclised amino acid; or a synthetic amino acid lacking a charge at the N-terminus.

In one preferred embodiment, the invention provides a use wherein the C-terminal F residue of the peptide molecule contains group z which removes the charge on that residue.

In one embodiment, the peptide sequence is selected from the group consisting of:

```
                                              (SEQ ID NO: 35)
a) Y-N-W-N-G-F-G-L-R-F.z;

(SEQ ID NO: 36)
b) Y-N-W-N-G-F-G-(D)L-R-F.z;

(SEQ ID NO: 37)
c) Y-N-W-N-G-F-G-(D)W-R-F.z;

(SEQ ID NO: 38)
d) Y-N-W-N-G-(D)W-G-L-R-F.z;

(SEQ ID NO: 39)
e) ac.Y-N-W-N-G-F-G-(D)W-R-F.z;

(SEQ ID NO: 40)
f) ac.Y-N-W-N-(D)W-F-G-(D)W-R-F.z;

(SEQ ID NO: 41)
g) ac.(D)Y-N-W-N-G-F-G-(D)W-R-F.z;

(SEQ ID NO: 42)
h) ac.Y-N-(D)W-N-G-F-G-(D)W-R-F.z;

(SEQ ID NO: 43)
i) ac.Y-(D)N-W-N-G-F-G-(D)W-R-F.z;

(SEQ ID NO: 44)
j) ac.Y-N-W-N-(D)A-F-G-(D)W-R-F.z;

(SEQ ID NO: 45)
k) ac.(D)A-N-W-N-G-F-G-(D)W-R-F.z;

(SEQ ID NO: 46)
l) ac.Y-N-(D)A-N-G-F-G-(D)W-R-F.z;

(SEQ ID NO: 47)
m) ac.Y-(D)A-W-N-G-F-G-(D)W-R-F.z;

(SEQ ID NO: 48)
n) ac.(D)W-N-W-N-G-F-G-(D)W-R-F.z;

(SEQ ID NO: 49)
o) ac.(D)F-N-W-N-G-F-G-(D)W-R-F.z;

(SEQ ID NO: 50)
p) ac.(D)Y-N-W-N-G-(D)W-G-(D)W-R-F.z;

(SEQ ID NO: 51)
q) ac.(D)A-N-W-N-G-(D)W-G-(D)W-R-F.z;

(SEQ ID NO: 52)
r) ac.(D)A-N-W-N-S-F-G-(D)W-R-F.z;

(SEQ ID NO: 53)
s) ac.D-A-N-W-N-G-F-G-W-R-F.z;

(SEQ ID NO: 54)
t) ac.(D)A-N-W-N-(D)S-F-G-(D)W-R-F.z;
or (SEQ ID NO: 55)
u) ac.(D)A-N-W-N-G-F-G-(D)L-R-F.z.
```

In one embodiment, the use according to the fourth aspect of the invention involves a molecule in which the peptide sequence comprises additional amino acid residues, or peptides, at the N- and/or C-terminus of the peptide sequence of the fourth aspect of the invention, thereby incorporating the peptide sequence into a larger polypeptide or protein molecule. Thus, the peptide sequence of the fourth aspect of the invention may comprise at the N- and/or C-terminus between 0 and 10 amino acids; or between 10 and 20 amino acids; or between 20 and 30 amino acids; or between 30 and 40 amino acids; or between 40 and 50 amino acids; or between 50 and 60 amino acids; or between 60 and 70 amino acids; or between 70 and 80 amino acids; or between 80 and 90 amino acids; or between 90 and 100 amino acids; or more than 100 amino acids.

In a preferred embodiment, the use according to the fourth aspect of the invention involves a molecule comprising or consisting of the additional peptide sequence R-R-M-K-W-K-K-Y (SEQ ID NO:20) or ac.R-R-M-K-W-K-K-Y (SEQ ID NO:20) at the N-terminus of the peptide sequence.

The R-R-M-K-W-K-K-Y (SEQ ID NO:20) sequence is a heptapeptide sequence from Antennapedia, as discussed above. Accordingly, the peptide of the fourth aspect of the invention may comprise or consist of the sequence:

(SEQ ID NO: 56)
R-R-M-K-W-K-K-Y-Y-N-W-N-G-F-G-L-R-F.z;

(SEQ ID NO: 57)
R-R-M-K-W-K-K-Y-Y-N-W-N-G-F-G-(D)L-R-F.z;

(SEQ ID NO: 58)
R-R-M-K-W-K-K-Y-Y-N-W-N-G-F-G-(D)W-R-F.z;

(SEQ ID NO: 59)
R-R-M-K-W-K-K-Y-Y-N-W-N-G-(D)W-G-L-R-F.z;

(SEQ ID NO: 60)
R-R-M-K-W-K-K-Y-Y-N-W-N-G-F-G-(D)W-R-F.z;

(SEQ ID NO: 61)
R-R-M-K-W-K-K-Y-Y-N-W-N-(D)W-F-G-(D)W-R-F.z;

(SEQ ID NO: 62)
R-R-M-K-W-K-K-Y-(D)Y-N-W-N-G-F-G-(D)W-R-F.z;

(SEQ ID NO: 63)
R-R-M-K-W-K-K-Y-Y-N-(D)W-N-G-F-G-(D)W-R-F.z;

(SEQ ID NO: 64)
R-R-M-K-W-K-K-Y-Y-(D)N-W-N-G-F-G-(D)W-R-F.z;

(SEQ ID NO: 65)
R-R-M-K-W-K-K-Y-Y-N-W-N-(D)A-F-G-(D)W-R-F.z;

(SEQ ID NO: 66)
R-R-M-K-W-K-K-Y-(D)A-N-W-N-G-F-G-(D)W-R-F.z;

(SEQ ID NO: 67)
R-R-M-K-W-K-K-Y-Y-N-(D)A-N-G-F-G-(D)W-R-F.z;

(SEQ ID NO: 68)
R-R-M-K-W-K-K-Y-Y-(D)A-W-N-G-F-G-(D)W-R-F.z;

(SEQ ID NO: 69)
R-R-M-K-W-K-K-Y-(D)W-N-W-N-G-F-G-(D)W-R-F.z;

(SEQ ID NO: 70)
R-R-M-K-W-K-K-Y-(D)F-N-W-N-G-F-G-(D)W-R-F.z;

(SEQ ID NO: 71)
R-R-M-K-W-K-K-Y-(D)Y-N-W-N-G-(D)W-G-(D)W-R-F.z;

(SEQ ID NO: 72)
R-R-M-K-W-K-K-Y-(D)A-N-W-N-G-(D)W-G-(D)W-R-F.z;

(SEQ ID NO: 73)
R-R-M-K-W-K-K-Y-(D)A-N-W-N-S-F-G-(D)W-R-F.z;

(SEQ ID NO: 74)
R-R-M-K-W-K-K-Y-(D)A-N-W-N-G-F-G-W-R-F.z;

(SEQ ID NO: 75)
R-R-M-K-W-K-K-Y-(D)A-N-W-N-(D)S-F-G-(D)W-R-F.z;
or (SEQ ID NO: 76)
R-R-M-K-W-K-K-Y-(D)A-N-W-N-G-F-G-(D)L-R-F.z.

Optionally, the N-terminal residue may comprise group y at the N-terminus, as defined above, and is preferably acetyl (ac).

In a particularly preferred embodiment, the peptide sequence of the fourth aspect of the invention is selected from the group consisting of:

(SEQ ID NO: 77)
R-R-M-K-W-K-K-Y-(D)A-N-W-N-G-F-G-(D)W-R-F.z;
or (SEQ ID NO: 77)
ac.R-R-M-K-W-K-K-Y-(D)A-N-W-N-G-F-G-(D)W-R-F.z.

As demonstrated in the accompanying examples, peptides of the invention comprising the N-terminal Antennapedia heptapeptide retain kisspeptin antagonist function.

Preferably, the peptide sequence of the fourth aspect of the invention is incorporated within some or all of the sequence of the full-length kisspeptin peptide. More preferably, the N-terminus of the peptide sequence of the fourth aspect of the invention can be extended to any length incorporating the peptide sequence of kisspeptin 1-54 (i.e. amino acid residues 1 to 54 of the kisspeptin sequence) and/or the peptide sequence of kisspeptin 1-45 (i.e. amino acid residues 1 to 45 of the kisspeptin sequence). For example, the peptide sequence of the fourth aspect of the invention may have the following sequence at its N-terminus:

(SEQ ID NO: 78)
GTSLSPPPESSGSRQQPGLSAPHSRQIPAPQGAVLVQREKDLP

Alternatively, the peptide sequence of the fourth aspect of the invention can be incorporated within a protein, such as an albumin and/or immunoglobulin protein. Incorporation into such molecules is thought to increase half-life and decrease the metabolic clearance within an individual of the peptide molecules of the invention.

By "a condition induced and/or worsened by kisspeptin activity in an individual" we include conditions in which the symptoms and/or progression and/or outcome of that condition in an individual are initiated, induced, elevated, increased and/or made more severe as a consequence of the activity of kisspeptin.

Preferably, the condition induced and/or worsened by kisspeptin activity in an individual is selected from the group comprising: a proliferative disorder; endometriosis; uterine fibroids; precocious puberty; pre-eclampsia; inter-uterine growth retardation (IUGR); ectopic pregnancy; menorrhagia; hypertension; coronary heart disease; pathologies of the central nervous system (CNS), pancreas and/or immune system; suppressed or inhibited ovulation; fertility; chemotherapy-induced and/or radiotherapy-induced damage to reproductive tissues; suppressed and/or inhibited wound healing; suppressed and/or inhibited growth hormone production.

For example, in reproductive tissues stimulated by gonadotropins and sex steroid hormones, kisspeptin antagonists will inhibit GnRH secretion, thereby inhibiting stimulation of reproductive tissues and reproductive cancers. Accordingly, antagonists of kisspeptin can be used to inhibit endogenous gonadotropin so that exogenous gonadotropin can be administered in a controlled manner to treat individuals having suppressed or inhibited ovulation, thereby inducing or elevating ovulation in that individual. Antagonists of kisspeptin may therefore also be used to reduce or inhibit fertility, resulting in a means of contraception in both males and females. Furthermore, the inhibition of stimulation of reproductive tissues by kisspeptin antagonists will permit their use in preventing chemotherapy-induced or radiotherapy-induced damage to reproductive tissues, thereby protecting reproductive tissues in an individual treated with chemotherapy and/or radiation therapy of cancer.

As demonstrated in the accompanying examples, the antagonists of the invention are capable of inhibiting and/or reducing the inhibitory effect of kisspeptin on cell migration. Since cell migration occurs, and is required, in wound healing, kisspeptin therefore plays a role in inhibiting wound healing. Accordingly, in one embodiment, the antagonists of the invention may be used to induce and/or promote wound healing in an individual in need thereof.

As demonstrated in the accompanying examples, the antagonists of the invention surprisingly elevated growth hormone levels in test individuals. Accordingly, the antagonists of the invention may be used to promote and/or induce growth hormone production in an individual in need thereof. For example, the antagonists of the invention could be used alongside existing treatments in which growth hormone therapy is used, such as in the treatment of renal failure.

Kisspeptin independently inhibits trophoblast invasion into the uterine wall (i.e. implantation), as occurs in pre-eclampsia or IUGR. In relation to pre-eclampsia, it has been shown that KiSS-1 mRNA is increased, preventing proper trophoblast invasion of the maternal blood supply [54]. Thus kisspeptin antagonists may be used to relieve that inhibition and, for example, allow trophoblast invasiveness during pregnancy in disorders such as pre-eclampsia.

It is known that kisspeptin independently induces vasoconstriction, and kisspeptin antagonists could therefore be used to treat hypertension, for example in peripheral tissues as a hypertensive agent to reduce vasoconstriction of blood vessels. GPR54 is expressed in the CNS and kisspeptin antagonists may be employed in modulating CNS function (such as in the hypocampul dentate granule cells).

In one embodiment, the acetyl group on the N-terminal residue of any of peptides (e) to (s), above, is replaced with a group y which removes the charge on that residue, and is preferably selected from the group consisting of: an acetyl group; a trifluoroacetyl group; a cyclised amino acid; or a synthetic amino acid lacking a charge at the N-terminus.

Kisspeptin is known to be expressed at high levels in the placenta and has been implicated in implantation. Poor implantation can cause pre-eclampsia and intra-uterine growth retardation, for which (until the present invention) there is no effective treatment.

Kisspeptin and its receptor (GPR54) is also expressed in trophoblast and in uterine cells (Hiden et al., 2007, *Rev. Endocr. Metab. Disord.*, 8:31-39) and, as shown in the accompanying Examples, the inventors have shown that kisspeptin causes foetal growth retardation. Accordingly, modulation of kisspeptin input will have application in pre-eclampsia, inter-uterine growth retardation (IUGR) and ectopic pregnancy.

Furthermore, kisspeptin and GPR54 induce increased vasoconstriction (Mead et al., 2007, *Endocrinology*, 148:140-147) and are present in atherosclerotic plaque, such that kisspeptin antagonists could be used to treat hypertension and coronary heart disease.

Kisspeptin and its receptor (GPR54) are also expressed widely in the central nervous system, pancreas and immune system (Muir et al., 2001, *J. Biol. Chem.*, 276:28969-28975; Kotani et al., 2001, *J. Biol. Chem.*, 276:34631-34636) such that antagonists may have application in pathologies of those tissues.

Preferably, the condition induced and/or worsened by kisspeptin activity is a condition of an animal. The animal may be a human, or may be any mammal such as a domesticated mammal (preferably of agricultural or commercial significance including a chicken; cat; dog; pig; sheep; cow; horse).

More preferably, the proliferative disorder is selected from the group consisting or comprising: benign prostatic hyperplasia; cancer; cancer of reproductive tissues; gynaecological cancer; prostate cancer; breast cancer; ovarian cancer; uterine cancer; cervical cancer; endometrial cancer; melanoma; pancreatic cancer; gastric cancer.

All cancers which express the kisspeptin receptor could potentially be treated using the molecules of the invention. Preferably, the cancer is a reproductive cancer (including prostate, endometrial, cervical, ovarian and breast cancers), all of which express the kisspeptin receptor.

Methods for detecting expression of cellular proteins are well known in the art. Methods suitable for detecting expression of the kisspeptin receptor include: in situ hybridisation and/or PCR for detecting the presence of mRNA encoding the kisspeptin receptor; radio-ligand binding for detecting the presence of the kisspeptin receptor protein; and methods involving antibodies capable of specifically binding to the kisspeptin receptor (for example, immunoblotting, immunohistochemistry, immunofluorescence, and ELISA).

It is preferred that the peptide molecule as defined in the third and/or fourth aspects of the invention is an antagonist of kisspeptin, or that the fragment or variant thereof is an antagonist of kisspeptin.

Preferably, the invention provides an antagonist according to the first and/or second aspect of the invention or the peptide molecule as defined in the third or fourth aspect of the invention for use in medicine. More preferably, the peptide molecule is an antagonist of kisspeptin.

In a fifth embodiment, the invention provides a peptide molecule comprising or consisting of the sequence:

$X^1$-G/W-$X^2$-R/(D)R-$X^3$        (SEQ ID NO: 3)

wherein:
$X^1$ is F or A or any D-amino-acid residue;
$X^2$ is L or A or any D-amino-acid residue;
$X^3$ is F or W; and
wherein the C-terminal amino acid residue of the peptide molecule contains group z which removes the charge on that residue;
or a fragment or variant thereof;
and wherein the peptide sequence is not:

F-G-L-R-F;        (SEQ ID NO: 4)

F-G-L-R-W;        (SEQ ID NO: 5)

```
F-G-(D)F-R-F;          (SEQ ID NO: 6)

F-G-A-R-W;             (SEQ ID NO: 7)

F-G-L-(D)R-W;          (SEQ ID NO: 8)

F-G-(D)L-R-W;          (SEQ ID NO: 9)

A-G-L-R-W;             (SEQ ID NO: 17)
or (D)F-G-L-R-W.          (SEQ ID NO: 10)
```

Preferably, the invention provides a peptide molecule wherein $X^1$ is (D)F. Typically, $X^2$ is a D-amino-acid residue selected from the group consisting of: (D)F, (D)L and (D)W.

Conveniently, the peptide molecule according to the fifth aspect of the invention is selected from the group consisting of:

```
(D)F-W-L-R-W;          (SEQ ID NO: 11)
or

F-G-(D)W-R-F.          (SEQ ID NO: 12)
```

In a preferred embodiment, the N-terminal residue contains group y which removes the charge on that residue. Preferably, $X^1$ contains group y which removes the charge on that residue. It is particularly preferred that group y is selected from the group consisting of: an acetyl group; a trifluoroacetyl group; a cyclised amino acid; or a synthetic amino acid lacking a charge at the N-terminus.

In one embodiment, $X^3$ contains group z which removes the charge on that residue.

Preferably, the peptide sequence is selected from the group consisting of:

```
I)   ac.F-G-(D)F-R-W.z;     (SEQ ID NO: 13)

II)  ac.F-G-(D)L-R-W.z;     (SEQ ID NO: 14)

III) ac.F-G-L-(D)R-W.z;     (SEQ ID NO: 15)

IV)  ac.F-G-A-R-W.z;        (SEQ ID NO: 16)

V)   ac.A-G-L-R-W.z;        (SEQ ID NO: 17)

VI)  ac.(D)F-W-L-R-W.z;     (SEQ ID NO: 18)
or

VII) ac.F-G-(D)W-R-F.z.     (SEQ ID NO: 19)
```

In one embodiment, the acetyl group on the N-terminal residue of any of peptides (I) to (VI), above, is replaced with a group y which removes the charge on that residue, and is preferably selected from the group consisting of: an acetyl group; a trifluoroacetyl group; a cyclised amino acid; or a synthetic amino acid lacking a charge at the N-terminus.

In one embodiment, the peptide molecule according to the fifth aspect of the invention involves a molecule comprising or consisting of additional amino acid residues, or peptides, at the N- and/or C-terminus of the peptide sequence of the fifth aspect of the invention, thereby incorporating the peptide sequence into a larger polypeptide or protein molecule.

Thus, the peptide sequence of the fifth aspect of the invention may comprise at the N- and/or C-terminus between 0 and 10 amino acids; or between 10 and 20 amino acids; or between 20 and 30 amino acids; or between 30 and 40 amino acids; or between 40 and 50 amino acids; or between 50 and 60 amino acids; or between 60 and 70 amino acids; or between 70 and 80 amino acids; or between 80 and 90 amino acids; or between 90 and 100 amino acids; or more than 100 amino acids.

In a preferred embodiment, the peptide molecule according to the fifth aspect of the invention comprises or consists of the additional peptide sequence R-R-M-K-W-K-K-Y (SEQ ID NO:20) or ac.R-R-M-K-W-K-K-Y (SEQ ID NO:20) at the N-terminus.

The R-R-M-K-W-K-K-Y (SEQ ID NO:20) sequence is a heptapeptide sequence from Antennapedia, as described above. Accordingly, the peptide molecule of the fifth aspect of the invention may comprise or consist of the sequence:

```
R-R-M-K-W-K-K-Y-(D)F-W-L-R-W;      (SEQ ID NO: 26)

R-R-M-K-W-K-K-Y-F-G-(D)W-R-F;      (SEQ ID NO: 27)

R-R-M-K-W-K-K-Y-F-G-(D)F-R-W.z;    (SEQ ID NO: 21)

R-R-M-K-W-K-K-Y-F-G-(D)L-R-W.z;    (SEQ ID NO: 22)

R-R-M-K-W-K-K-Y-F-G-L-(D)R-W.z;    (SEQ ID NO: 23)

R-R-M-K-W-K-K-Y-F-G-A-R-W.z;       (SEQ ID NO: 24)

R-R-M-K-W-K-K-Y-A-G-L-R-W.z;       (SEQ ID NO: 25)

R-R-M-K-W-K-K-Y-(D)F-W-L-R-W.z;    (SEQ ID NO: 26)
or

R-R-M-K-W-K-K-Y-F-G-(D)W-R-F.z.    (SEQ ID NO: 27)
```

Optionally, the N-terminal residue may comprise group y at the N-terminus, as defined above, and is preferably acetyl (ac).

Preferably, the peptide sequence of the fifth aspect of the invention is incorporated within some or all of the sequence of the full-length kisspeptin peptide. More preferably, the N-terminus of the peptide sequence of the fifth aspect of the invention can be extended to any length incorporating the peptide sequence of kisspeptin 1-54 (i.e. amino acid residues 1 to 54 of the kisspeptin sequence) and/or the peptide sequence of kisspeptin 1-45 (i.e. amino acid residues 1 to 45 of the kisspeptin sequence). For example, the peptide sequence of the fifth aspect of the invention may have the following sequence at its N-terminus:

```
                                          (SEQ ID NO: 28)
GTSLSPPPESSGSRQQPGLSAPHSRQIPAPQGAVLVQREKDLPNYNWNS
```

Alternatively, the peptide sequence of the fifth aspect of the invention can be incorporated within a protein, such as an albumin and/or immunoglobulin protein. Incorporation into such molecules is thought to increase half-life and decrease the metabolic clearance within an individual of the peptide molecules of the invention.

In a sixth aspect, the invention provides a peptide molecule comprising or consisting of the sequence:

```
X^A-X^B-X^C-N-X^D-X^E-G-X^F-R-F     (SEQ ID NO: 29)
``` wherein:
$X^A$ is Y or any D-amino-acid residue;
$X^B$ is N or any D-amino acid residue;
$X^C$ is W or any D-amino acid residue;
$X^D$ is G or S or any D-amino acid residue;
$X^E$ is F or (D)W or (D)L;
$X^F$ is W or L or any D-amino acid residue; and wherein the C-terminal amino acid residue of the peptide molecule contains group z which removes the charge on that residue;
or a fragment or variant thereof;
and wherein the peptide sequence is not:

```
Y-N-W-N-S-F-G-L-R-F;           (SEQ ID NO: 30)

(D)Y-(D)N-W-N-S-F-G-W-R-F;     (SEQ ID NO: 31)

(D)Y-(D)N-W-N-G-F-G-W-R-F;     (SEQ ID NO: 32)

(D)Y-(D)N-W-N-S-F-G-(D)W-R-F;  (SEQ ID NO: 33)
or (D)Y-(D)N-W-N-G-F-G-(D)W-R-F.  (SEQ ID NO: 34)
```

Preferably, the peptide molecule of the sixth aspect of the invention provides that $X^A$ is a D-amino-acid residue selected from the group consisting of: (D)F and (D)Y and (D)A. It is preferred that $X^B$ is a D-amino-acid residue selected from the group consisting of: (D)A and (D)N.

In one embodiment, the invention provides a peptide molecule wherein when one of $X^A$ or $X^B$ is (D)Y, the other is not (D)N. One particularly preferred embodiment is wherein $X^A$ and $X^B$ are not both a D-amino acid residue. In one embodiment, when $X^F$ is (D)W, $X^A$ is (D)F.

Preferably, $X^C$ is a D-amino-acid residue selected from the group consisting of: (D)A and (D)W. Conveniently, $X^D$ is a D-amino-acid residue selected from the group consisting of: (D)A and (D)W. Typically, $X^F$ is a D-amino-acid residue selected from the group consisting of: (D)L and (D)W.

In one embodiment, when $X^D$ is S, $X^F$ is (D)W and/or $X^A$ is not (D)Y. Preferably, when $X^D$ is S, $X^F$ is (D)W and/or $X^A$ is (D)A.

In one embodiment, when $X^E$ and $X^F$ are both (D)W, $X^A$ is not (D)Y. Preferably, when $X^E$ and $X^F$ are both (D)W, $X^A$ is (D)A.

Conveniently, the invention provides a peptide molecule wherein the N-terminal residue contains group y which removes the charge on that residue. In one embodiment, $X^1$ contains group y which removes the charge on that residue. Typically, group y is selected from the group consisting of: an acetyl group; a trifluoroacetyl group; a cyclised amino acid; or a synthetic amino acid lacking a charge at the N-terminus.

In a preferred embodiment, the C-terminal F residue of the peptide molecule contains group z which removes the charge on that residue.

It is most preferred that the peptide molecule according to the sixth aspect of the invention comprises or consists of a peptide sequence selected from the group consisting of:

```
a) Y-N-W-N-G-F-G-L-R-F.z;                 (SEQ ID NO: 35)

b) Y-N-W-N-G-F-G-(D)L-R-F.z;              (SEQ ID NO: 36)

c) Y-N-W-N-G-F-G-(D)W-R-F.z;              (SEQ ID NO: 37)

d) Y-N-W-N-G-(D)W-G-L-R-F.z;              (SEQ ID NO: 38)

e) ac.Y-N-W-N-G-F-G-(D)W-R-F.z;           (SEQ ID NO: 39)

f) ac.Y-N-W-N-(D)W-F-G-(D)W-R-F.z;        (SEQ ID NO: 40)

g) ac.(D)Y-N-W-N-G-F-G-(D)W-R-F.z;        (SEQ ID NO: 41)

h) ac.Y-N-(D)W-N-G-F-G-(D)W-R-F.z;        (SEQ ID NO: 42)

i) ac.Y-(D)N-W-N-G-F-G-(D)W-R-F.z;        (SEQ ID NO: 43)

j) ac.Y-N-W-N-(D)A-F-G-(D)W-R-F.z;        (SEQ ID NO: 44)

k) ac.(D)A-N-W-N-G-F-G-(D)W-R-F.z;        (SEQ ID NO: 45)

l) ac.Y-N-(D)A-N-G-F-G-(D)W-R-F.z;        (SEQ ID NO: 46)

m) ac.Y-(D)A-W-N-G-F-G-(D)W-R-F.z;        (SEQ ID NO: 47)

n) ac.(D)W-N-W-N-G-F-G-(D)W-R-F.z;        (SEQ ID NO: 48)

o) ac.(D)F-N-W-N-G-F-G-(D)W-R-F.z;        (SEQ ID NO: 49)

p) ac.(D)Y-N-W-N-G-(D)W-G-(D)W-R-F.z;     (SEQ ID NO: 50)

q) ac.(D)A-N-W-N-G-(D)W-G-(D)W-R-F.z;     (SEQ ID NO: 51)

r) ac.(D)A-N-W-N-S-F-G-(D)W-R-F.z;        (SEQ ID NO: 52)

s) ac.(D)-A-N-W-N-G-F-G-W-R-F.z;          (SEQ ID NO: 53)

t) ac.(D)A-N-W-N-(D)S-F-G-(D)W-R-F.z;     (SEQ ID NO: 54)
or u) ac.(D)A-N-W-N-G-F-G-(D)L-R-F.z.        (SEQ ID NO: 55)
```

In one embodiment, the acetyl group on the N-terminal residue of any of peptides (e) to (s), above, is replaced with a group y which removes the charge on that residue, and is preferably selected from the group consisting of: an acetyl group; a trifluoroacetyl group; a cyclised amino acid; or a synthetic amino acid lacking a charge at the N-terminus.

In one embodiment, the peptide molecule according to the sixth aspect of the invention involves a molecule comprising or consisting of additional amino acid residues, or peptides, at the N- and/or C-terminus of the peptide sequence of the sixth aspect of the invention, thereby incorporating the peptide sequence into a larger polypeptide or protein molecule. Thus, the peptide sequence of the sixth aspect of the invention may comprise at the N- and/or C-terminus between 0 and 10 amino acids; or between 10 and 20 amino acids; or between 20 and 30 amino acids; or between 30 and 40 amino acids; or between 40 and 50 amino acids; or between 50 and 60 amino acids; or between 60 and 70 amino acids; or between 70 and 80 amino acids; or between 80 and 90 amino acids; or between 90 and 100 amino acids; or more than 100 amino acids.

In a preferred embodiment, the peptide molecule according to the sixth aspect of the invention involves a molecule comprising or consisting of the additional peptide sequence R-R-M-K-W-K-K-Y(SEQ ID NO:20) or ac.R-R-M-K-W-K-K-Y(SEQ ID NO:20) at the N-terminus of the peptide sequence.

The R-R-M-K-W-K-K-Y (SEQ ID NO:20) sequence is a heptapeptide sequence from Antennapedia, as discussed above. Accordingly, the peptide of the invention may comprise or consist of the sequence:

R-R-M-K-W-K-K-Y-Y-N-W-N-G-F-G-L-R-F.z; (SEQ ID NO: 56)

R-R-M-K-W-K-K-Y-Y-N-W-N-G-F-G-(D)L-R-F.z; (SEQ ID NO: 57)

R-R-M-K-W-K-K-Y-Y-N-W-N-G-F-G-(D)W-R-F.z; (SEQ ID NO: 58)

R-R-M-K-W-K-K-Y-Y-N-W-N-G-(D)W-G-L-R-F.z; (SEQ ID NO: 59)

R-R-M-K-W-K-K-Y-Y-N-W-N-G-F-G-(D)W-R-F.z; (SEQ ID NO: 60)

R-R-M-K-W-K-K-Y-Y-N-W-N-(D)W-F-G-(D)W-R-F.z; (SEQ ID NO: 61)

R-R-M-K-W-K-K-Y-(D)Y-N-W-N-G-F-G-(D)W-R-F.z; (SEQ ID NO: 62)

R-R-M-K-W-K-K-Y-Y-N-(D)W-N-G-F-G-(D)W-R-F.z; (SEQ ID NO: 63)

R-R-M-K-W-K-K-Y-Y-(D)N-W-N-G-F-G-(D)W-R-F.z; (SEQ ID NO: 64)

R-R-M-K-W-K-K-Y-Y-N-W-N-(D)A-F-G-(D)W-R-F.z; (SEQ ID NO: 65)

R-R-M-K-W-K-K-Y-(D)A-N-W-N-G-F-G-(D)W-R-F.z; (SEQ ID NO: 66)

R-R-M-K-W-K-K-Y-Y-N-(D)A-N-G-F-G-(D)W-R-F.z; (SEQ ID NO: 67)

R-R-M-K-W-K-K-Y-Y-(D)A-W-N-G-F-G-(D)W-R-F.z; (SEQ ID NO: 68)

R-R-M-K-W-K-K-Y-(D)W-N-W-N-G-F-G-(D)W-R-F.z; (SEQ ID NO: 69)

R-R-M-K-W-K-K-Y-(D)F-N-W-N-G-F-G-(D)W-R-F.z; (SEQ ID NO: 70)

R-R-M-K-W-K-K-Y-(D)Y-N-W-N-G-(D)W-G-(D)W-R-F.z; (SEQ ID NO: 71)

R-R-M-K-W-K-K-Y-(D)A-N-W-N-G-(D)W-G-(D)W-R-F.z; (SEQ ID NO: 72)

R-R-M-K-W-K-K-Y-(D)A-N-W-N-S-F-G-(D)W-R-F.z; (SEQ ID NO: 73)

R-R-M-K-W-K-K-Y-(D)A-N-W-N-G-F-G-W-R-F.z; (SEQ ID NO: 74)

R-R-M-K-W-K-K-Y-(D)A-N-W-N-(D)S-F-G-(D)W-R-F.z; (SEQ ID NO: 75)

or

R-R-M-K-W-K-K-Y-(D)A-N-W-N-G-F-G-(D)L-R-F.z. (SEQ ID NO: 76)

Optionally, the N-terminal residue may comprise group y at the N-terminus, as defined above, and is preferably acetyl (ac).

In a particularly preferred embodiment, the peptide sequence is selected from the group consisting of:

R-R-M-K-W-K-K-Y-(D)A-N-W-N-G-F-G-(D)W-R-F.z; (SEQ ID NO: 77)

or ac.R-R-M-K-W-K-K-Y-(D)A-N-W-N-G-F-G-(D)W-R-F.z. (SEQ ID NO: 77)

As demonstrated in the accompanying examples, peptides of the invention comprising the N-terminal Antennapedia heptapeptide retain kisspeptin antagonist function.

Preferably, the peptide sequence of the sixth aspect of the invention is incorporated within some or all of the sequence of the full-length kisspeptin peptide. More preferably, the N-terminus of the peptide sequence of the sixth aspect of the invention can be extended to any length incorporating the peptide sequence of kisspeptin 1-54 (i.e. amino acid residues 1 to 54 of the kisspeptin sequence) and/or the peptide sequence of kisspeptin 1-45 (i.e. amino acid residues 1 to 45 of the kisspeptin sequence). For example, the peptide sequence of the sixth aspect of the invention may have the following sequence at its N-terminus:

GTSLSPPPESSGSRQQPGLSAPHSRQIPAPQGAVLVQREKDLP (SEQ ID NO: 78)

Alternatively, the peptide sequence of the sixth aspect of the invention can be incorporated within a protein, such as an albumin and/or immunoglobulin protein. Incorporation into such molecules is thought to increase half-life and decrease the metabolic clearance within an individual of the peptide molecules of the invention.

In one embodiment, the invention provides a peptide molecule wherein z is $NH_2$ or N-propylamide or N-ethylamide (NHEt) or N-methylamide or N-butylamide.

Preferably, z has a molecular weight of less than 200, preferably less than 150, preferably less than 100. Preferably, z is NHR' wherein R' is H or $C_1$ to $C_4$ alkyl or z is OR" wherein R" is $C_1$ to $C_4$ alkyl. Preferably, z is an amide. Preferably, z is $NH_2$ or N-propylamide or N-ethylamide (NHEt) or N-methylamide or N-butylamide.

In a seventh embodiment, the invention provides a pharmaceutical composition comprising or consisting of an effective amount of an antagonist according to the invention or a peptide molecule according to the invention, and a pharmaceutically-acceptable excipient or diluent.

By "effective amount" we include an amount of the molecule of the invention that is sufficient to reduce and/or alleviate and/or prevent symptoms associated with a condition induced and/or worsened by kisspeptin activity in an individual. An "effective amount" may, for example, be determined by undertaking dose studies in animals (and, if possible, humans) for inhibition of gonadotrophin and/or steroid hormones; doses would likely be in the region of 1-100 mg per day delivered subcutaneously or intraperitoneally or orally.

An effective amount could also be determined in vitro by using the methods described in the Examples (for example, the methods used to monitor antagonism of kisspeptin binding to the kisspeptin receptor and/or antagonism of kisspeptin-mediated stimulation of inositol phosphate production in a cell) or in vivo by monitoring the reduction and/or alleviation and/or prevention of symptoms in an individual (such as an animal) associated with a condition induced and/or worsened by kisspeptin activity in an individual, which symptoms will be know to those skilled in the relevant medical field.

In relation to in vitro methods of monitoring kisspeptin antagonism, those skilled in the art will understand that other or additional cellular and enzymatic activities could be monitored to measure kisspeptin-mediated stimulation. For example, it is known that the Gq G protein activates phospholipase (which generates IP and diacylglycerol that in turn mobilise $Ca^{2+}$ and activate protein kinase C, respectively) and that protein kinase C phosphorylates and activates extracellular-regulated kinase (ERK) and/or the mitogen-activated protein kinase (MAPK) cascade and members thereof; accordingly, a skilled person could monitor the activity and/or presence of any or all of those cellular components to determine kisspeptin-mediated stimulation.

In an eighth embodiment, the invention provides a method of treating a condition induced and/or worsened by kisspeptin activity in an individual comprising or consisting of the step of administering to the individual a pharmaceutical composition according to the seventh aspect of the invention, or an effective amount of an antagonist of kisspeptin according to the first or second aspect of the invention, or an effective amount of a peptide molecule according to the second, third, fourth and/or fifth aspect of the invention.

The molecules, medicaments and pharmaceutical compositions of the present invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period. Preferably, delivery is performed intra-muscularly (i.m.) and/or sub-cutaneously (s.c.) and/or intravenously (i.v.).

The molecules, medicaments and pharmaceutical compositions of the present invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of the agents, medicaments and pharmaceutical compositions of the invention. A device which delivers a pulsed electric field to cells increases the permeability of the cell membranes to the drug, resulting in a significant enhancement of intracellular drug delivery.

The molecules, medicaments and pharmaceutical compositions of the invention can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of delivery of the molecules, medicaments and pharmaceutical compositions of the invention is the ReGel injectable system that is thermo-sensitive. Below body temperature, ReGel is an injectable liquid while at body temperature it immediately forms a gel reservoir that slowly erodes and dissolves into known, safe, biodegradable polymers. The active substance is delivered over time as the biopolymers dissolve.

The molecules, medicaments and pharmaceutical compositions of the invention can also be delivered orally. The process employs a natural process for oral uptake of vitamin $B_{12}$ and/or vitamin D in the body to co-deliver proteins and peptides. By riding the vitamin $B_{12}$ and/or vitamin D uptake system, the nucleic acids, molecules and pharmaceutical formulations of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The molecules, medicaments and pharmaceutical compositions of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al. (1998), Trends Cell Biol 8, 84-87.

Preferably, the medicament and/or pharmaceutical composition of the present invention is a unit dosage containing a daily dose or unit, daily sub-dose or an appropriate fraction thereof, of the active ingredient.

The molecules, medicaments and pharmaceutical compositions of the invention will normally be administered orally or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the molecules, medicaments and pharmaceutical compositions of the invention can be administered alone but will generally be administered in admixture with a suitable pharmaceutical excipient, diluent or carrier selected with regard to the intended route of administration and standard pharmaceutical practice.

For example, the molecules, medicaments and pharmaceutical compositions of the invention can be administered orally, buccally or sublingually in the form of tablets, capsules, ovules, elixirs, solutions or suspensions, which may contain flavouring or colouring agents, for immediate-, delayed- or controlled-release applications. The molecules, medicaments and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents of the invention may be combined with various sweetening or flavouring agents, colouring matter or dyes, with emulsifying and/or suspending agents and with diluents such as water, ethanol, propylene glycol and glycerin, and combinations thereof.

The molecules, medicaments and pharmaceutical compositions of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The medicaments and compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the molecules, medicaments and pharmaceutical compositions of the invention will usually be from 0.1 to 100 mg per adult per day administered in single or divided doses.

Thus, for example, the tablets or capsules of the molecules of the invention may contain from 0.1 mg to 100 mg of active agent for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The molecules, medicaments and pharmaceutical compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a agent of the invention and a suitable powder base such as lactose or starch.

Aerosol or dry powder formulations are preferably arranged so that each metered dose or "puff" contains at least 0.1 mg of a molecule of the invention for delivery to the patient. It will be appreciated that the overall daily dose with an aerosol will vary from patient to patient, and may be administered in a single dose or, more usually, in divided doses throughout the day.

Alternatively, the molecules, medicaments and pharmaceutical compositions of the invention can be administered in the form of a suppository or pessary, or they may be applied topically in the form of a lotion, solution, cream, gel, ointment or dusting powder. The molecules, medicaments and pharmaceutical compositions of the invention may also be transdermally administered, for example, by the use of a skin patch. They may also be administered by the ocular route, particularly for treating diseases of the eye.

For ophthalmic use, the molecules, medicaments and pharmaceutical compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the molecules, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or parenteral administration of the molecules, medicaments and pharmaceutical compositions of the invention agents of the invention is the preferred route, being the most convenient.

For veterinary use, the molecules, medicaments and pharmaceutical compositions of the invention is administered as a suitably acceptable formulation in accordance with normal veterinary practice and the veterinary surgeon will determine the dosing regimen and route of administration which will be most appropriate for a particular animal.

Conveniently, the formulation is a pharmaceutical formulation.

Advantageously, the formulation is a veterinary formulation.

It is particularly preferred that the molecules of the invention are formulated using peptide formulations already known in the arts of medicine and pharmacy, such as those used in formulations of GnRH peptide agonists (for example, formulations comprising or consisting of polyglycyl lactide copolymer and/or polyethylene glycol and/or oil and/or microcrystalline suspensions may be useful for injecting the molecules of the invention).

In a ninth aspect of the invention, the invention provides a method for identifying an antagonist of kisspeptin comprising or consisting of the step(s) of:
 i) providing a compound to be tested;
 ii) determining the ability of the compound in (i) to bind to the kisspeptin receptor;
 iii) determining the ability of the compound in (i) to antagonise kisspeptin-mediated stimulation of inositol phosphate production in a cell; and
 iv) identifying the compound as an antagonist of kisspeptin in the event that it is capable of binding to the kisspeptin receptor and capable of antagonising kisspeptin-mediated stimulation of inositol phosphate production in a cell.

Thus, the method of the ninth aspect of the invention may be performed to determine whether a particular test compound or test molecule (for example, a test compound or test molecule comprising or consisting of a peptide sequence that is an analogue of part or all of the kisspeptin peptide sequence) has the ability to bind to the kisspeptin receptor and functionally antagonise kisspeptin-mediated stimulation of inositol phosphate production in a cell (such as cell lines, like CHO, HEK or COS cell lines, transiently or stably transfected with the human kisspeptin receptor, GPR54). The accompanying Examples describe experimental methods suitable for determining the binding ability of a compound to the kisspeptin receptor and for measuring kisspeptin-mediated stimulation of inositol phosphate production in a cell. Other appropriate methods will be known to those skilled in the art.

For example, as discussed above, those skilled in the art will understand that other or additional cellular and enzymatic activities could be monitored to measure kisspeptin-mediated stimulation. For example, it is known that the Gq G protein activates phospholipase (which generates IP and diacylglycerol that in turn mobilise $Ca^{2+}$ and activate protein kinase C, respectively) and that protein kinase C phosphorylates and activates extracellular-regulated kinase (ERK) and/or the mitogen-activated protein kinase (MAPK) cascade and members thereof; accordingly, a skilled person could monitor the activity and/or presence of any or all of those cellular components to determine kisspeptin-mediated stimulation.

Preferably, the test compound or molecule will be identified as capable of binding to the kisspeptin receptor if it has a binding affinity (that is, a Kd) of <100 nM.

Preferably, the test compound or molecule will be identified as capable of antagonising the ability of 10 nM of kisspeptin to stimulate inositol phosphate production in a cell, as described in the accompanying examples. Preferably, the test compound or molecule will be identified as capable of achieving at least 40% inhibition of the stimulation by 10 nM kisspeptin; more preferably, at least 50% or 60% or 70% or 80% or 90% or 100% inhibition will be achieved.

For example, a compound capable of achieving 40% or less inhibition of stimulation by 10 mM kisspeptin may not be regarded as an antagonist. A compound capable of achieving between around 40% to 80% inhibition of stimulation by 10 mM kisspeptin may be regarded as a "poor" antagonist. A compound capable of achieving 80% or more inhibition of stimulation by 10 mM kisspeptin may be regarded as a "good" antagonist.

Preferably, the method of the ninth aspect of the invention further comprises or consisting of the step of making or synthesising the compound or molecule identified as an antagonist of kisspeptin in step (iv), according to the methods described herein or known to those skilled in the art.

More preferably, the method further comprises or consisting of the step of formulating the compound or molecule identified in the ninth aspect of the invention (or the synthesised compound or molecule) into a pharmaceutical composition or medicament, according to the methods described herein or known to those skilled in the art.

The listing or discussion of a prior-published document in this specification should not necessarily be taken as an acknowledgement that the document is part of the state of the art or is common general knowledge.

Preferred, non-limiting examples which embody certain aspects of the invention will now be described, with reference to the following figures:

Table 1: The stimulation of inositol phosphate (IP) and inhibition of 10 nM Kisspeptin stimulation of IP by Kisspeptin analogues.

FIG. 1: A—Binding dose response for kisspeptin in CHO cells stably transfected with GPR54.
  B—IP dose response for kisspeptin in CHO cells stably transfected with GPR54.

Figure 2A:
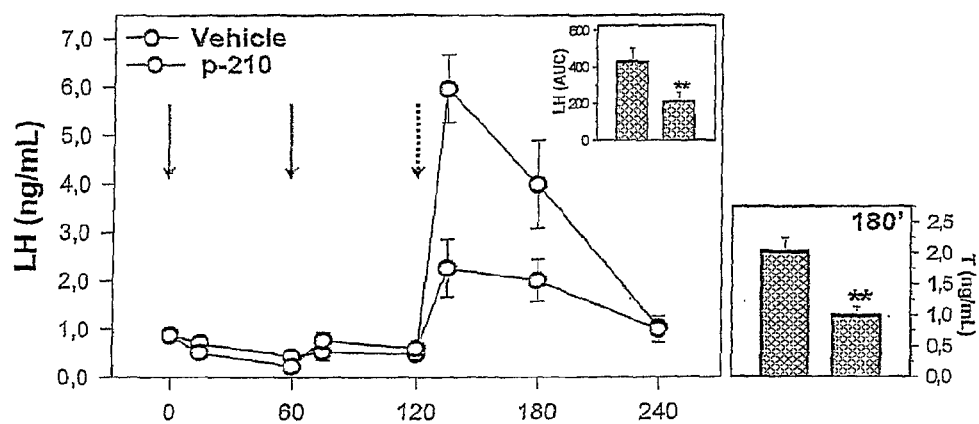
Figure 2B:
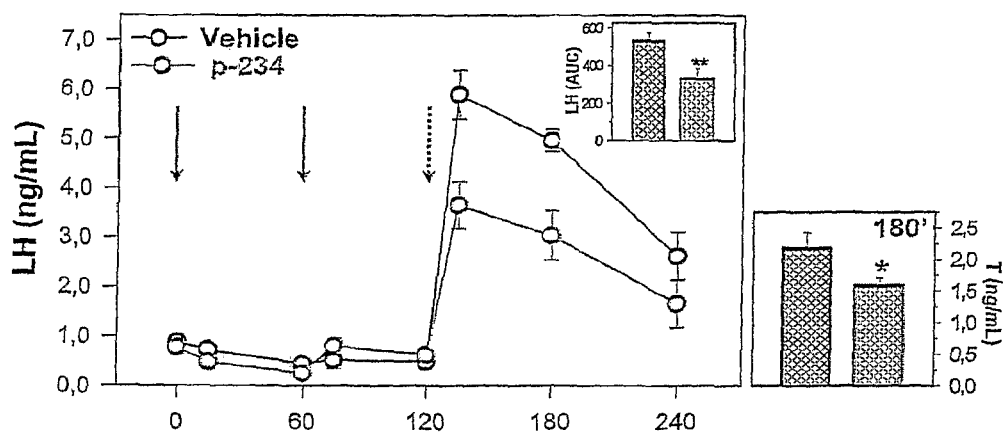
Figure 2C:
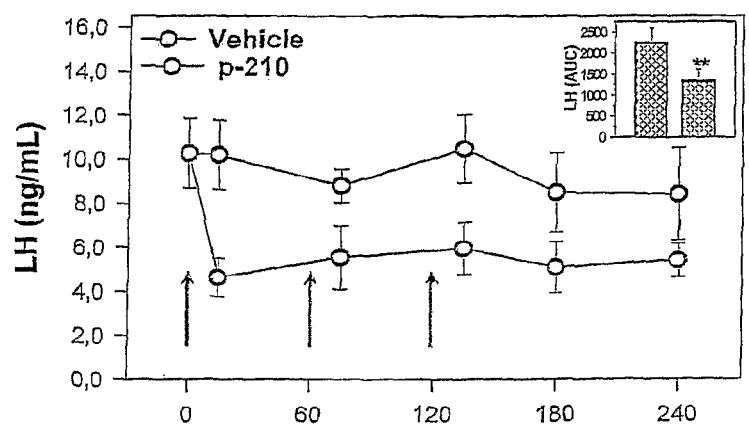

FIG. 2: A—Ability of repeated injections of compound 210 (0, 60, 120 min) to interfere with the potent LH- and testosterone releasing effect of kisspeptin-10 (100 pmol) (120 min) in intact male rats.
  B—Ability of repeated injections of compound 234 to interfere with the potent LH and testosterone-releasing effect of kisspeptin-10 (100 pmol) in intact male rats.
  C—Ability of repeated injections (0, 60, 120 min) of compound 210 to attenuate the elevated LH levels in orchidectomised male rats.

Figure 3:
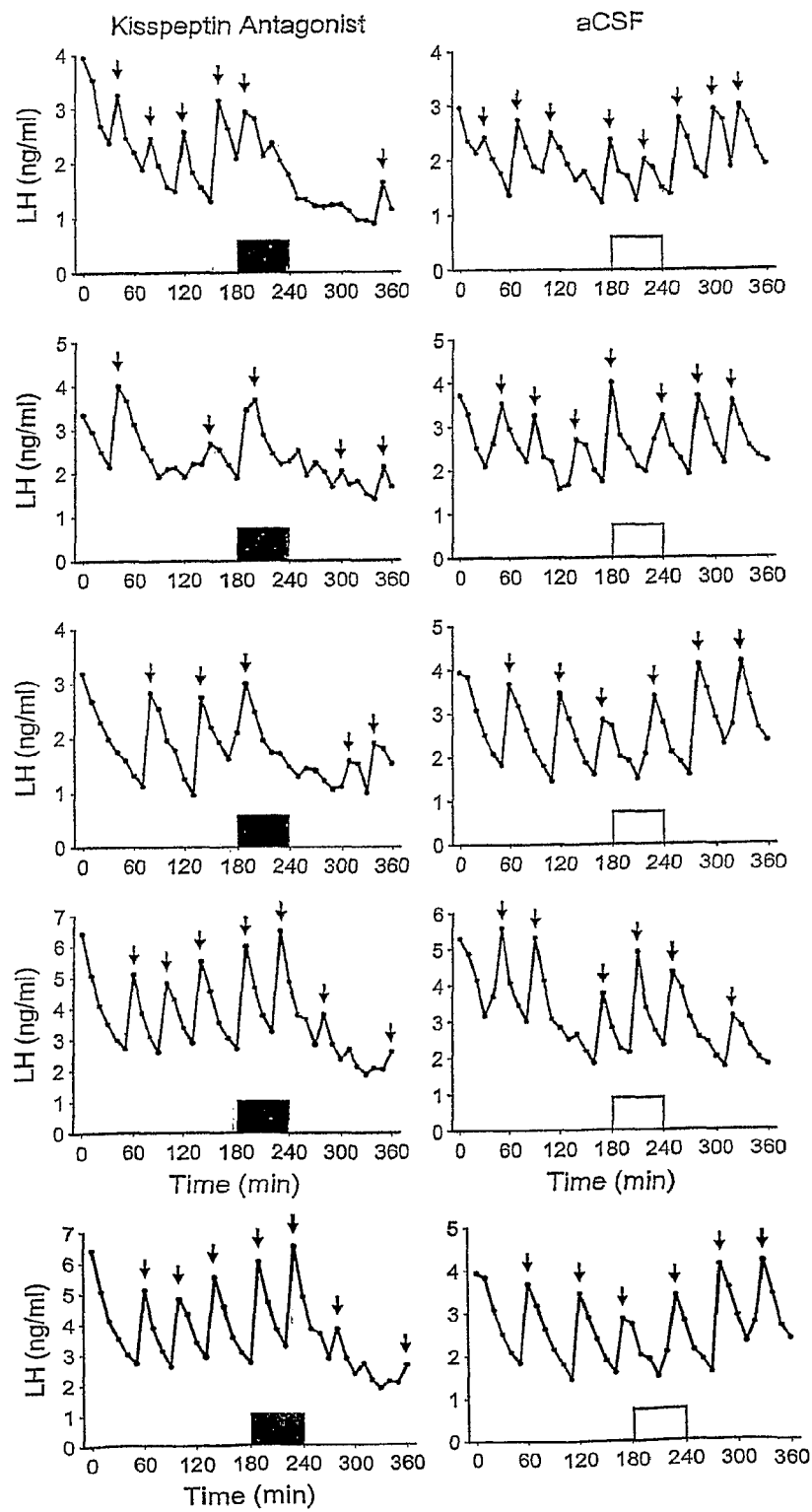

FIG. 3: Central infusion of kisspeptin antagonist inhibits the secretory pulses of LH in OVX ewes. Concentrations of LH are shown in ewes treated with kisspeptin antagonist (closed bars) or control (opened bars). Arrows indicate LH pulses as defined in the Materials and Methods.

Figure 4:
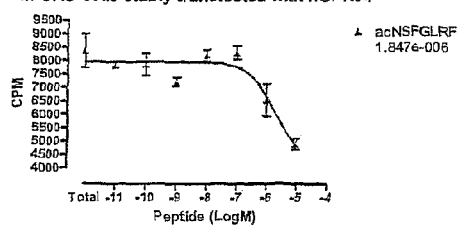
Figure 4:
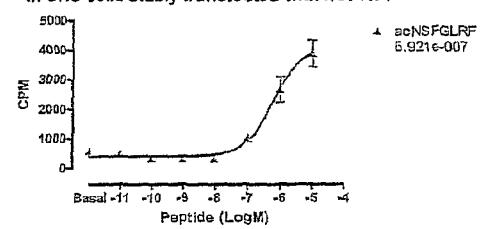
Figure 4:
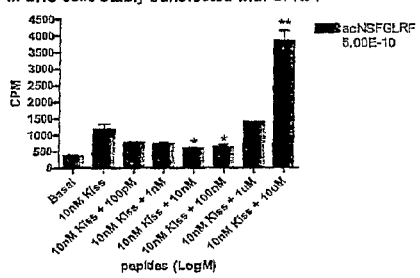
Figure 4:
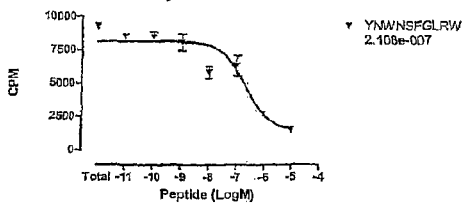
Figure 4:
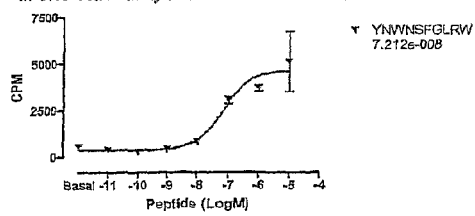
Figure 4:
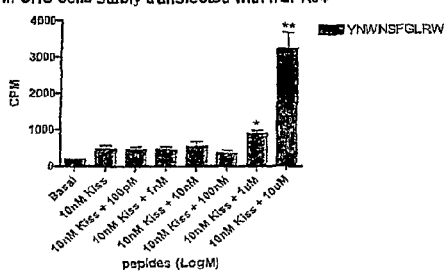
Figure 4:
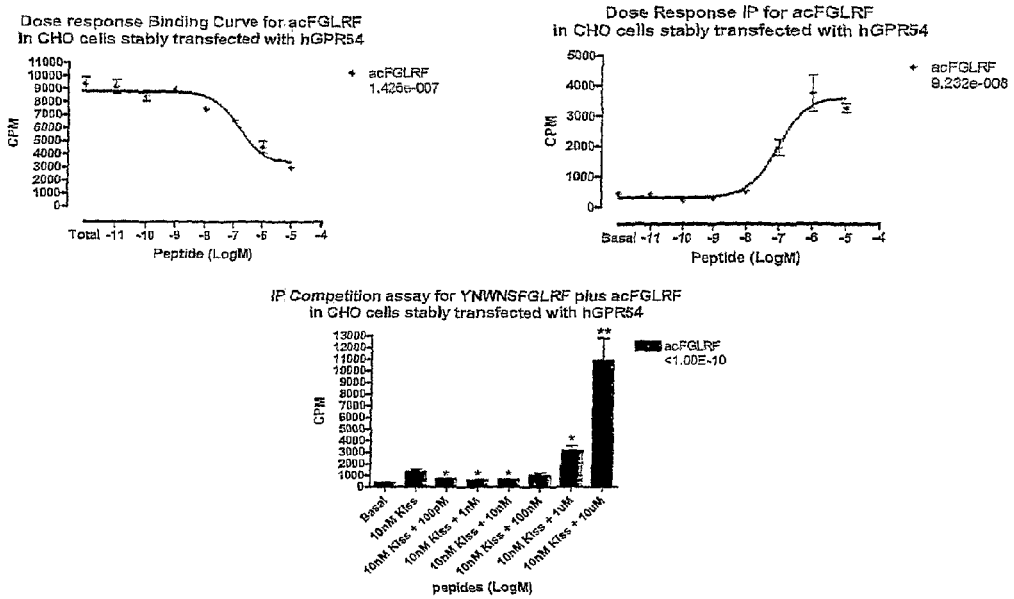
Figure 4:
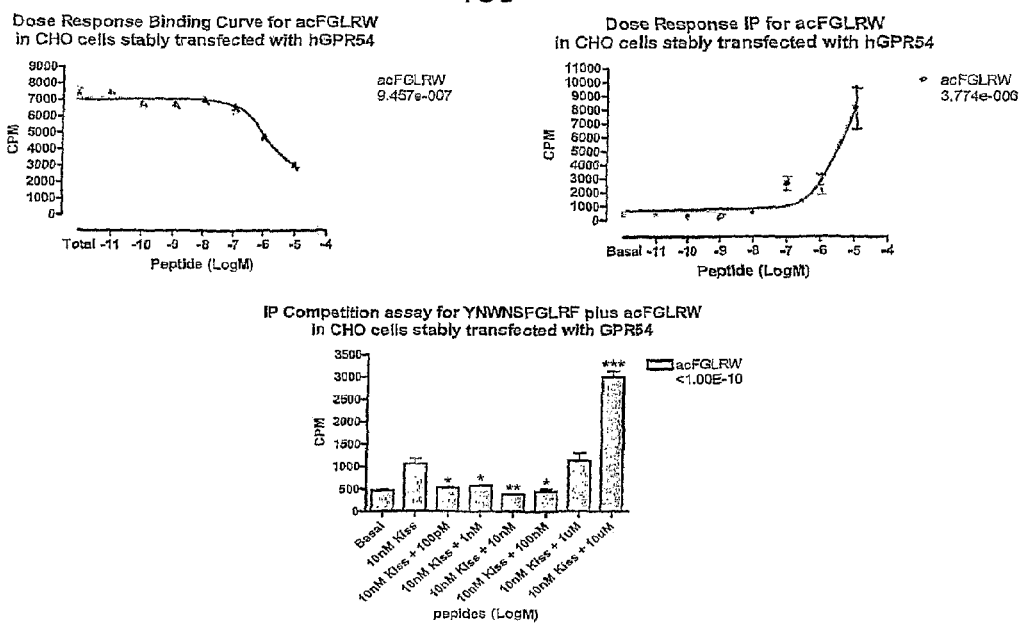
Figure 4:
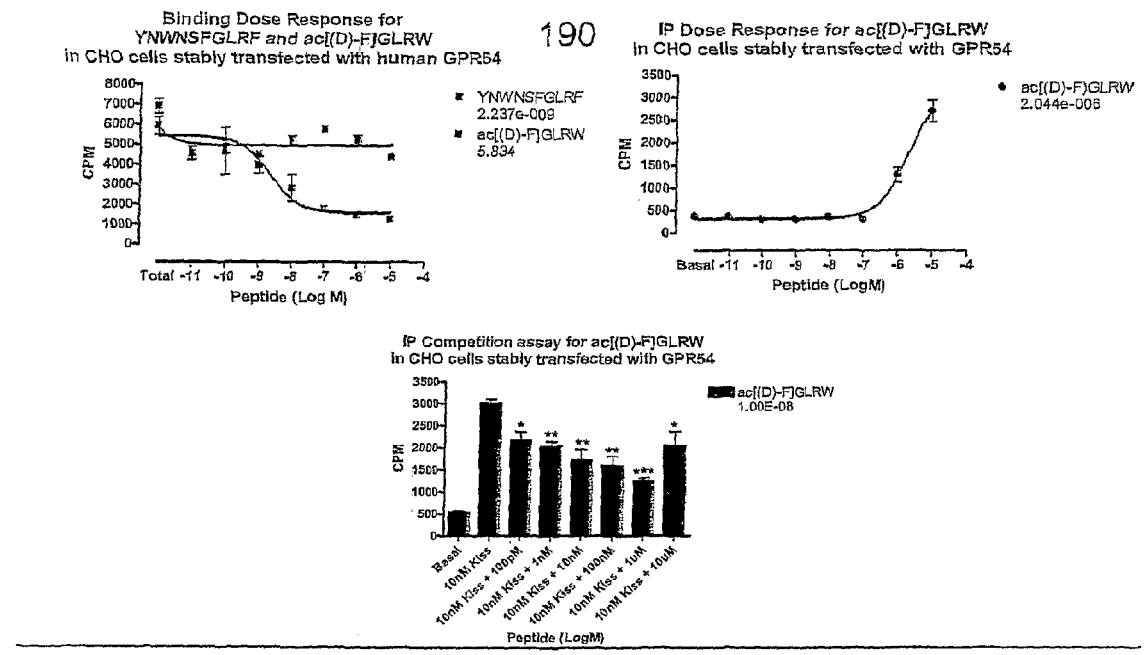
Figure 4:
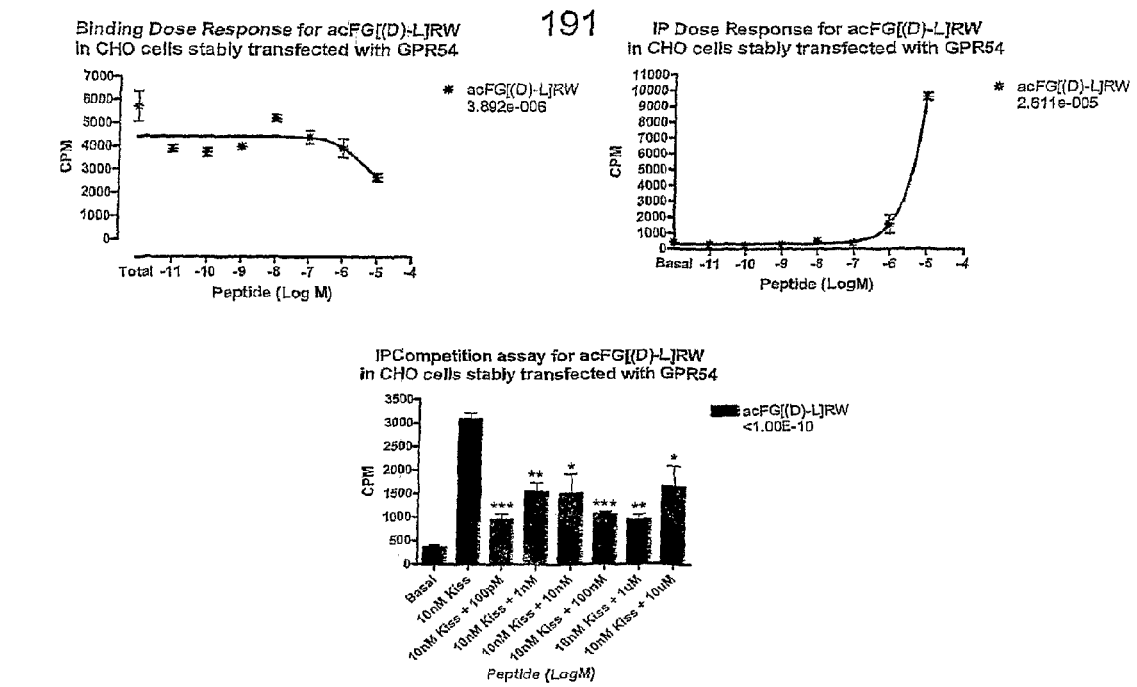
Figure 4:
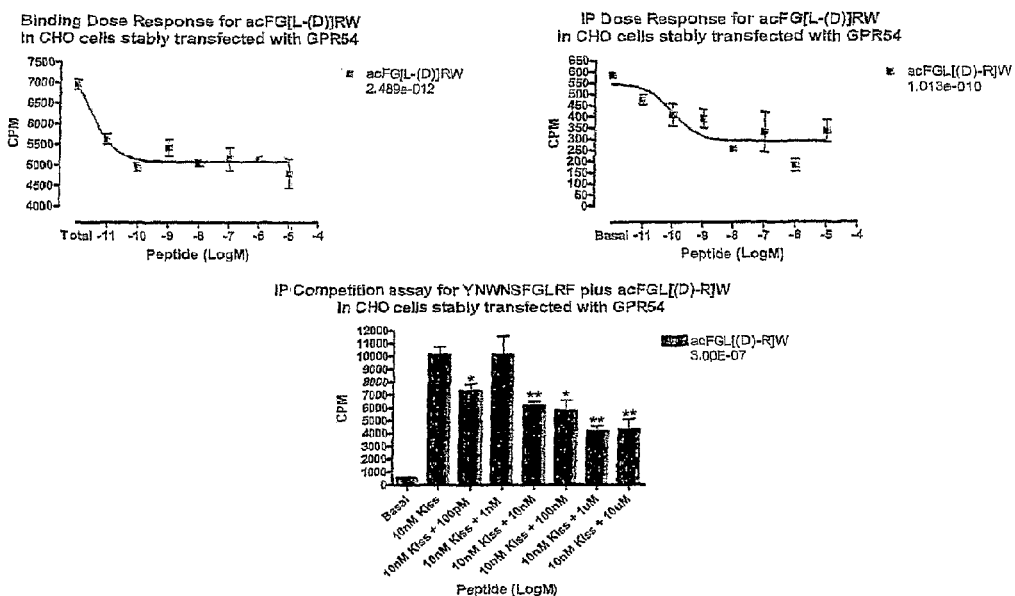
Figure 4:
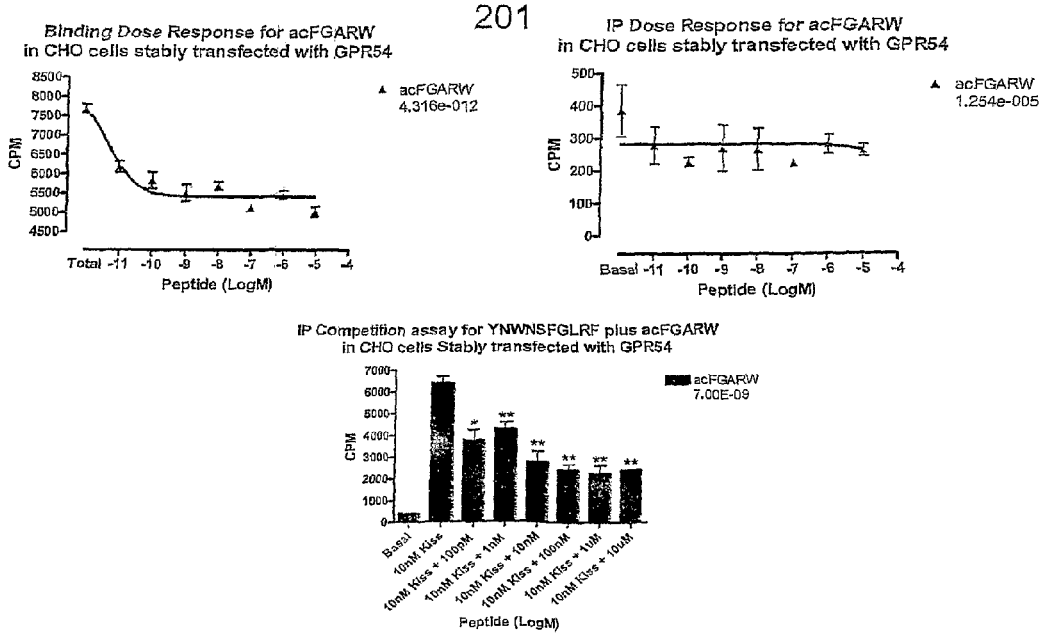
Figure 4:
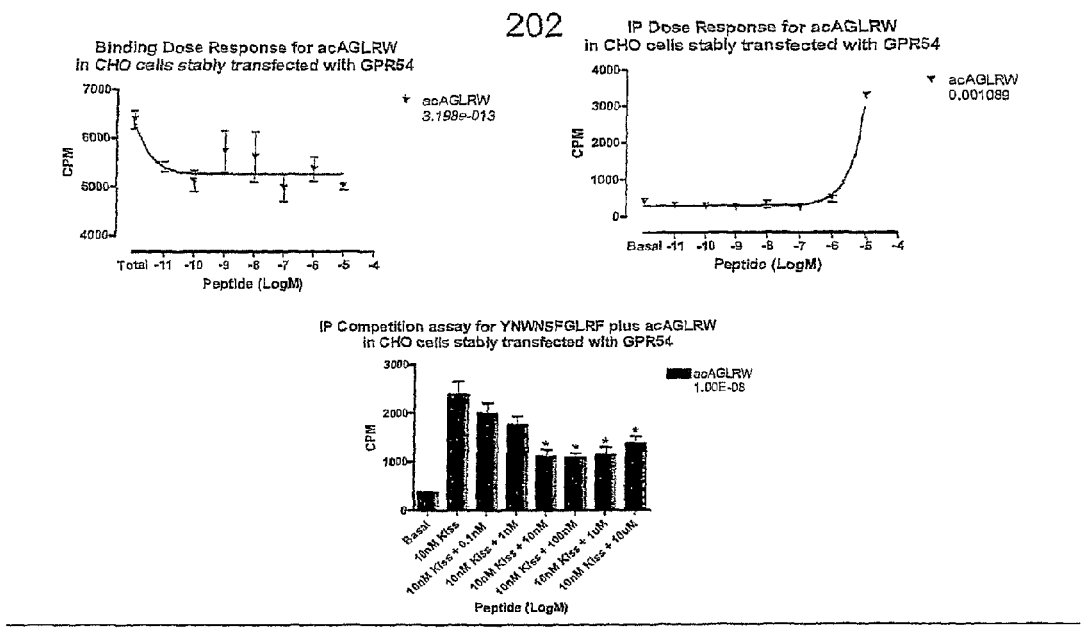
Figure 4:
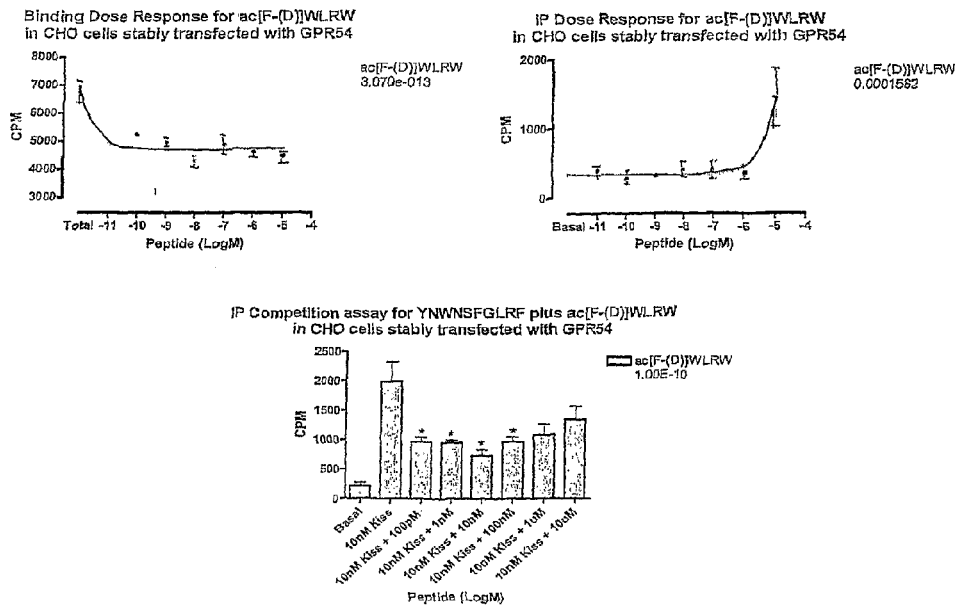
Figure 4:
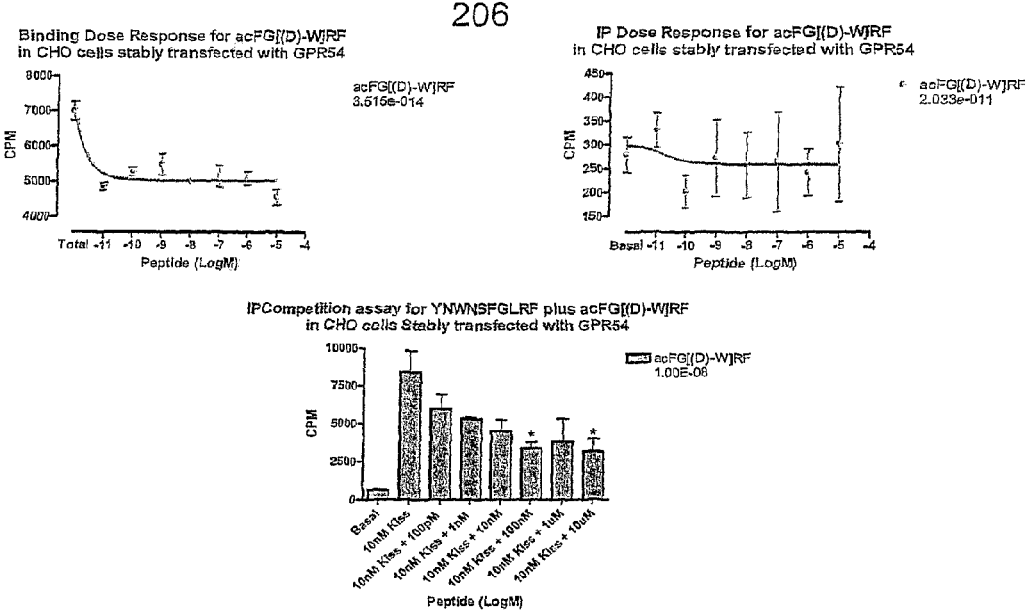
Figure 4:
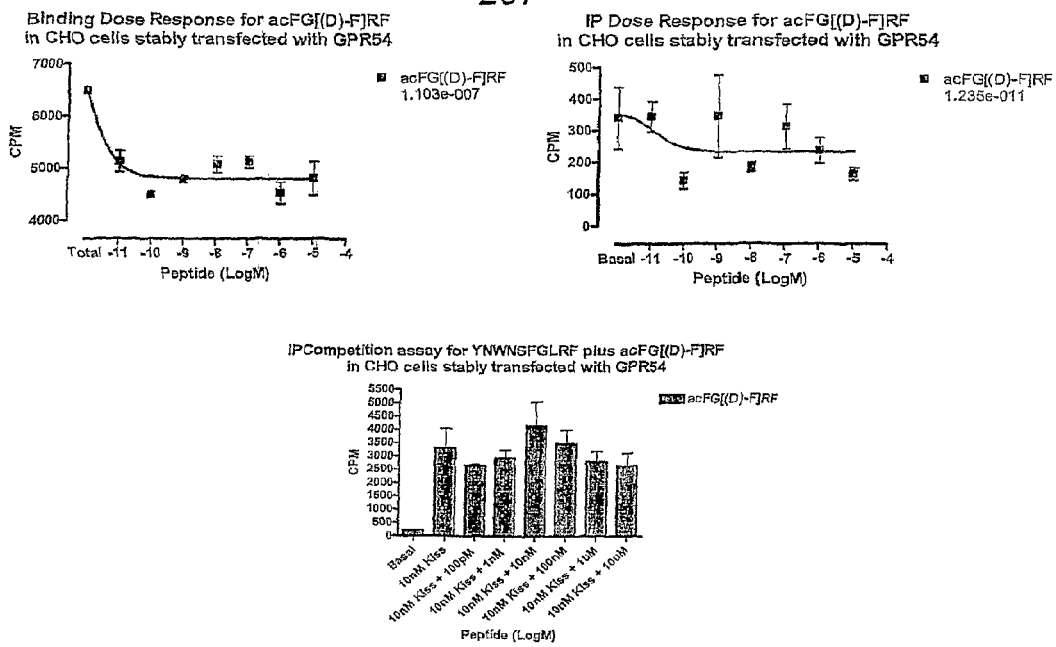
Figure 4:
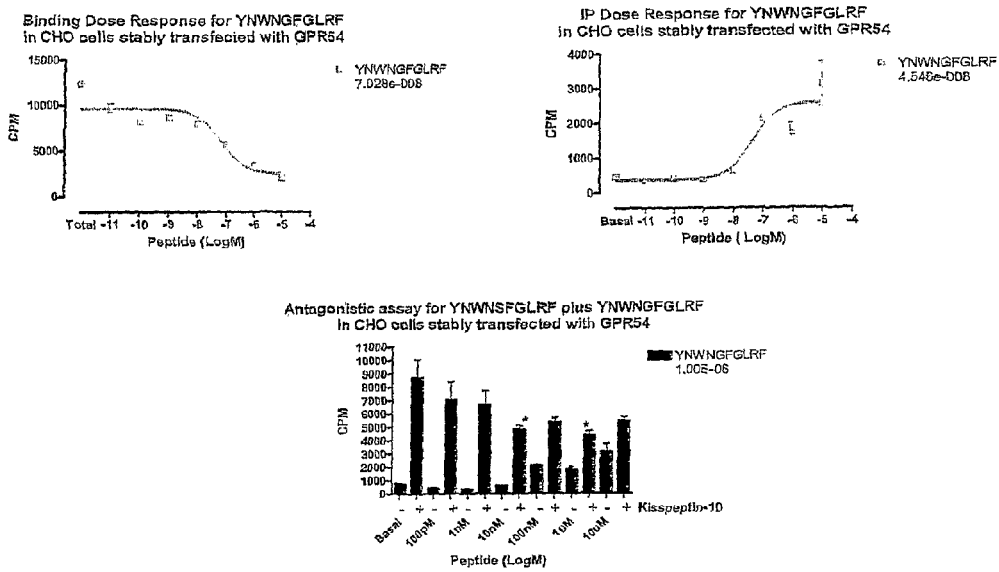
Figure 4:
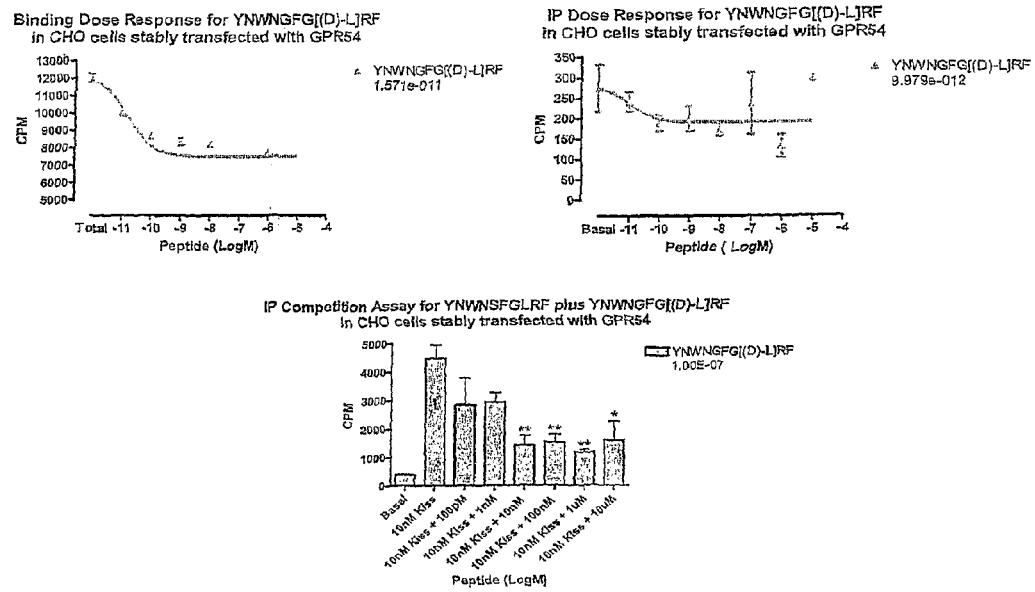
Figure 4:
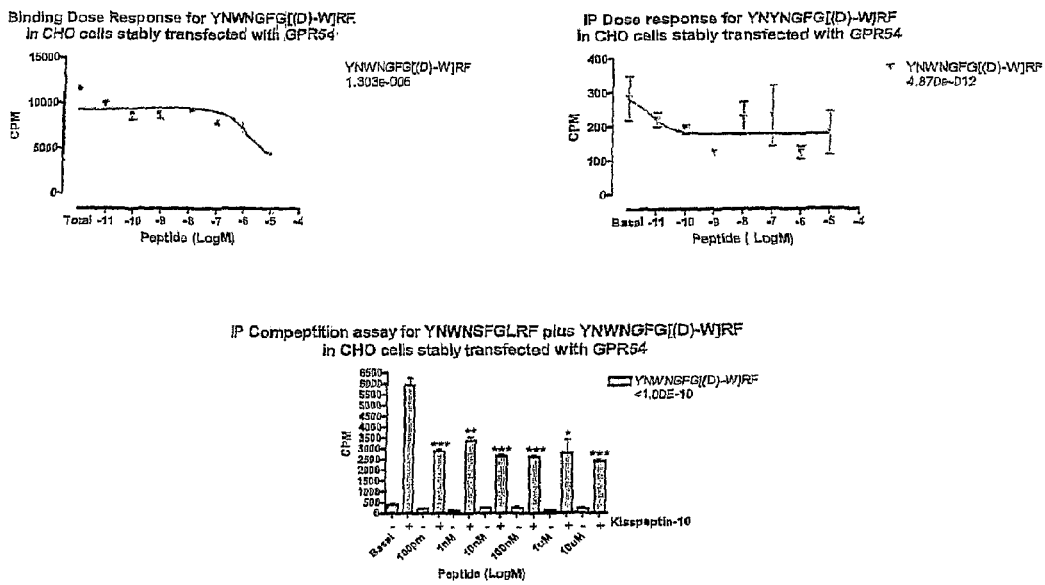
Figure 4:
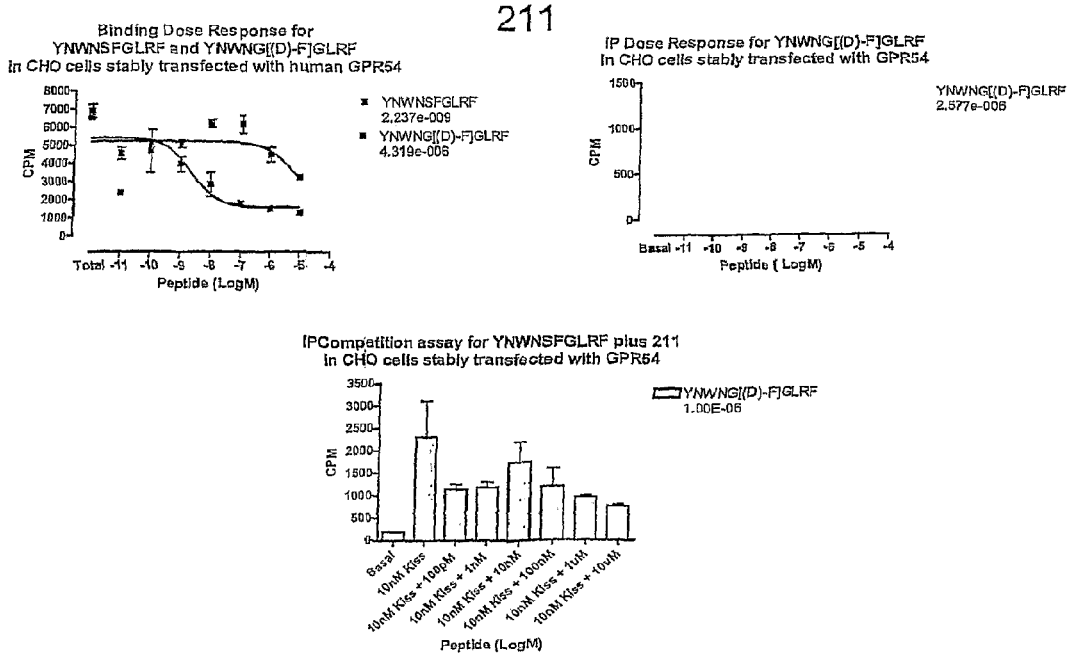
Figure 4:
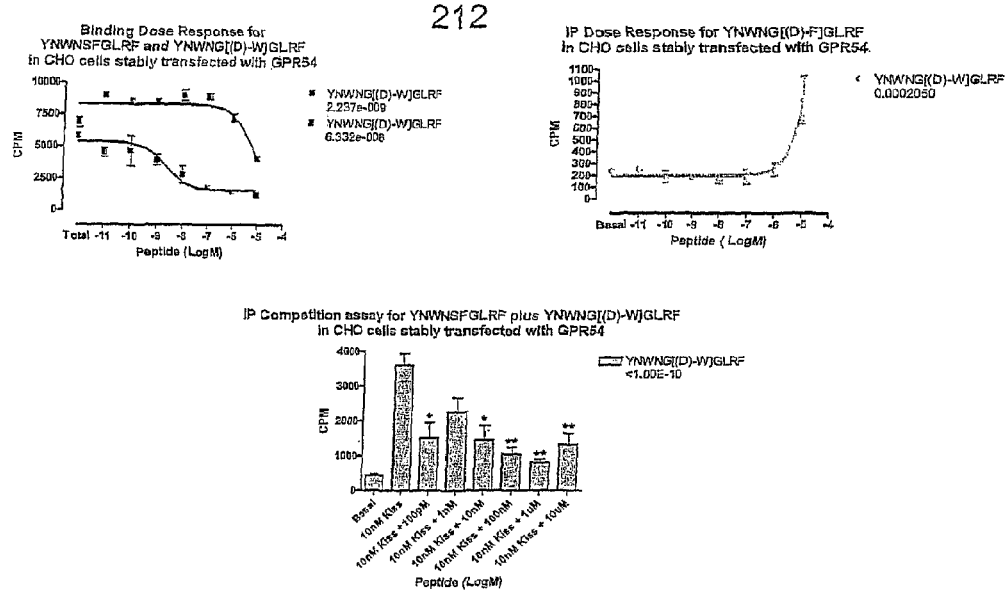
Figure 4:
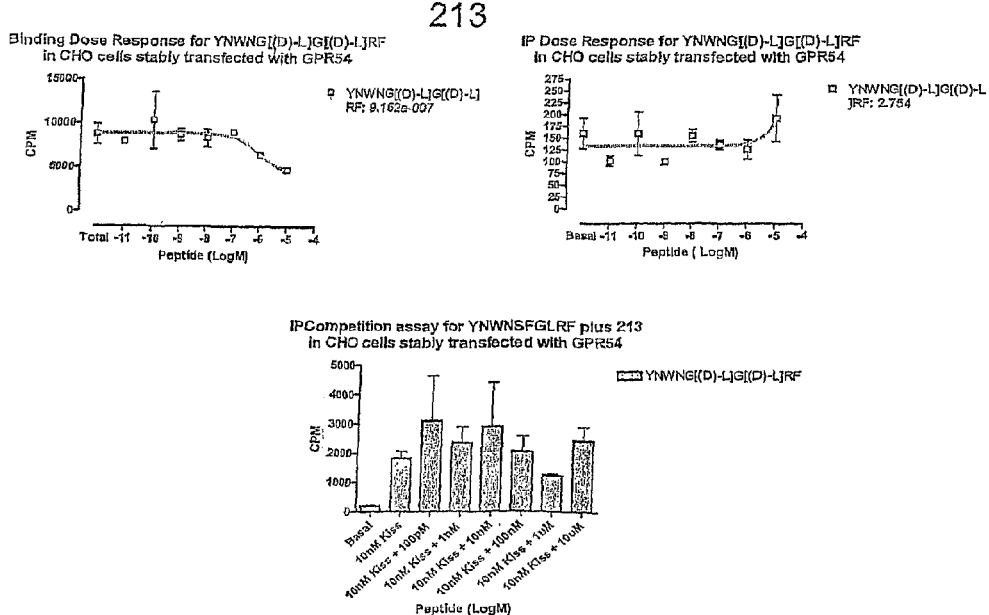
Figure 4:
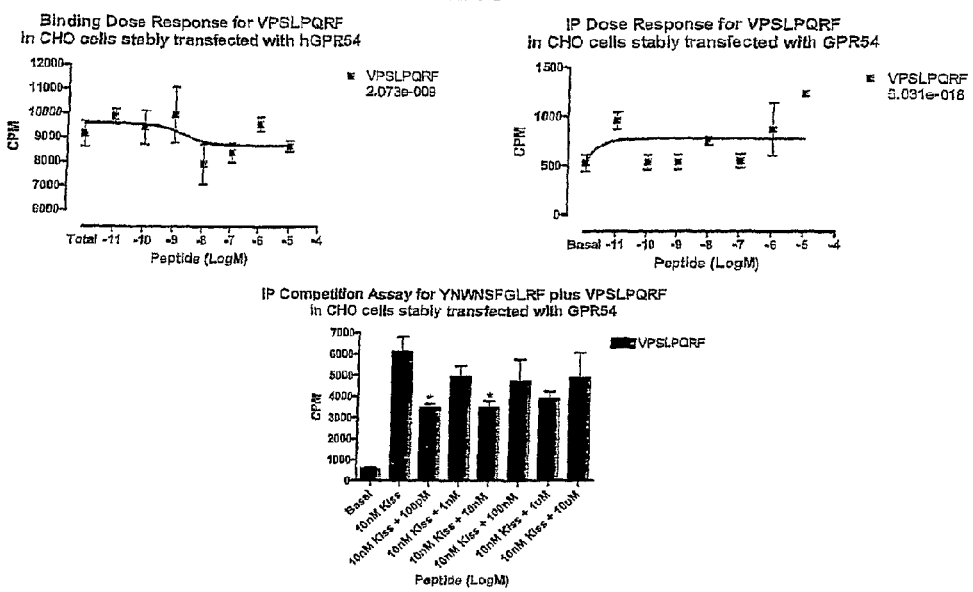
Figure 4:
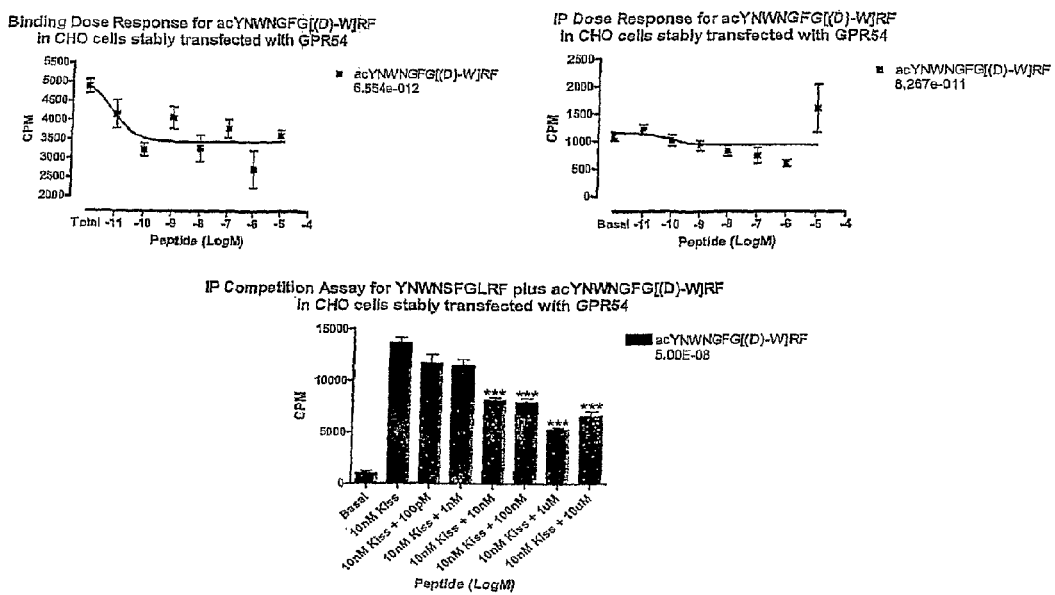
Figure 4:
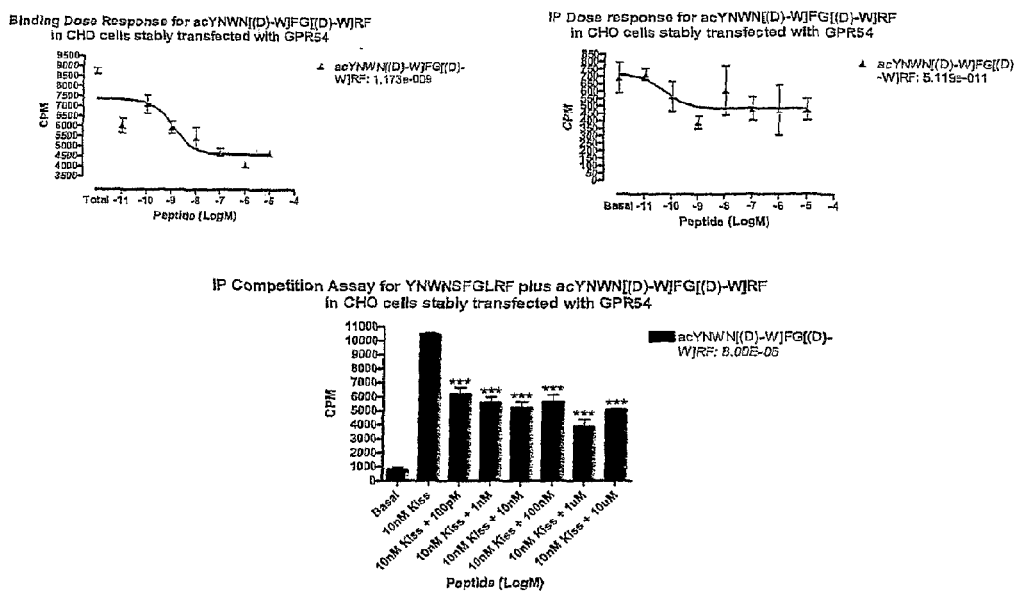
Figure 4:
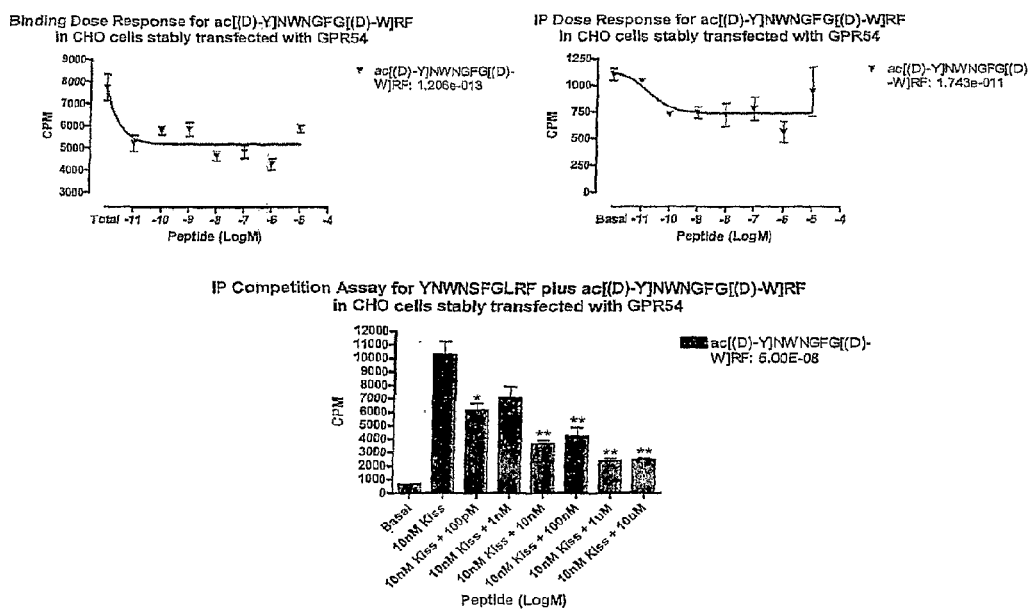
Figure 4:
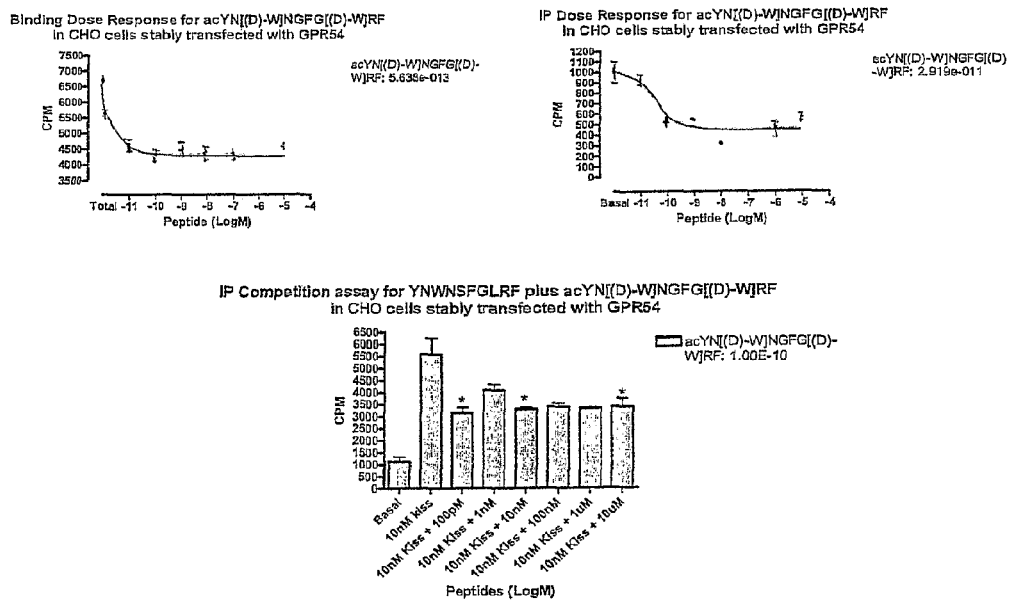
Figure 4:
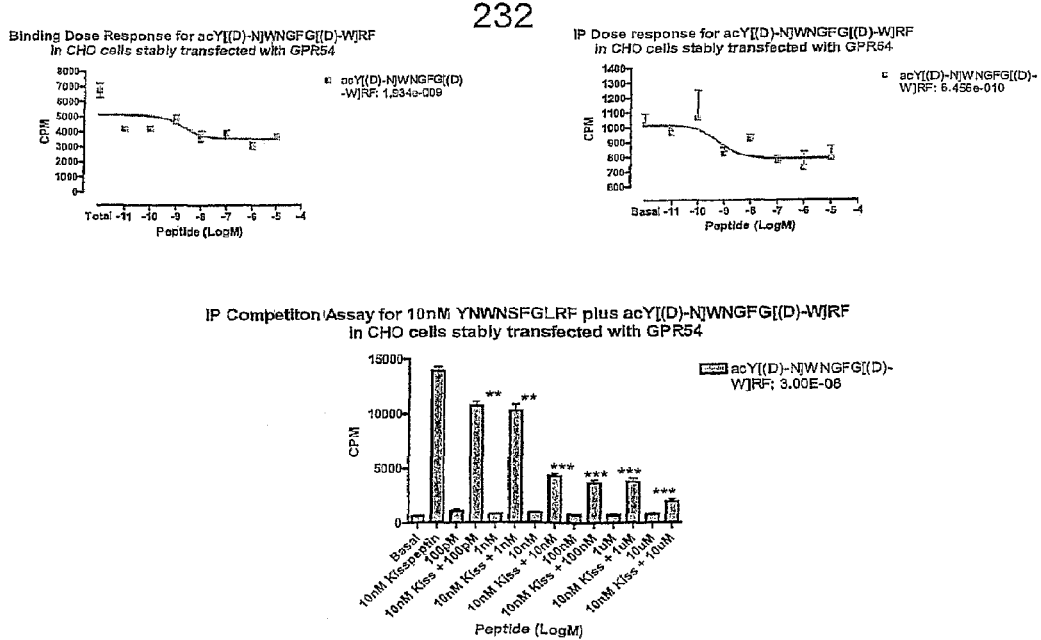
Figure 4:
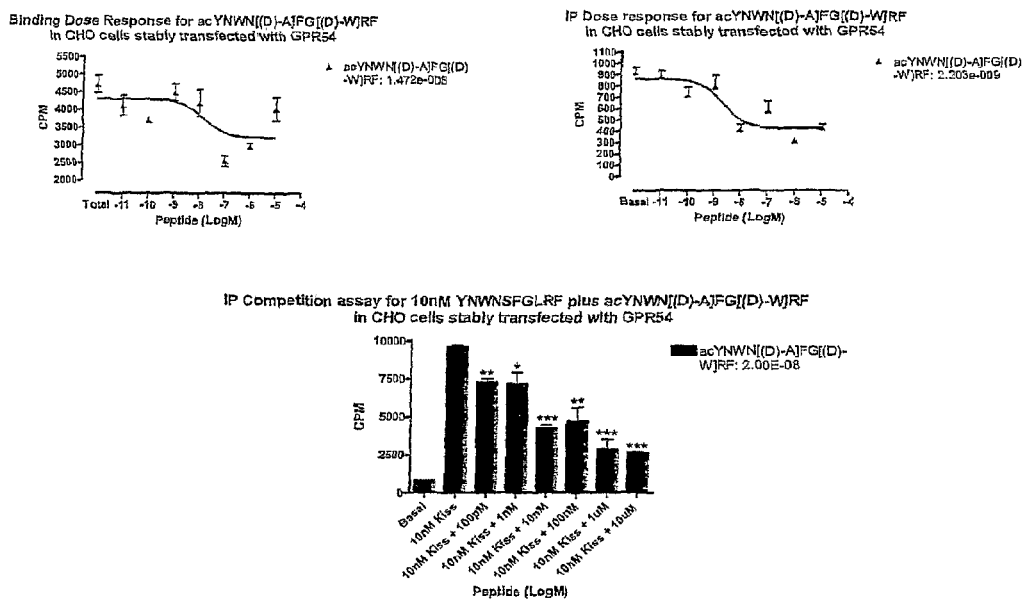
Figure 4:
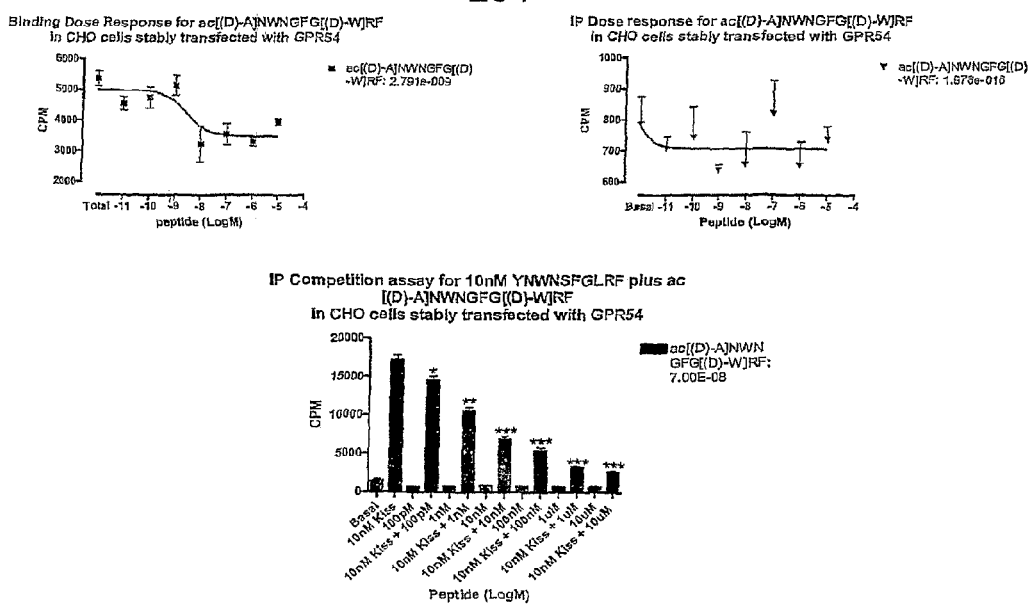
Figure 4:
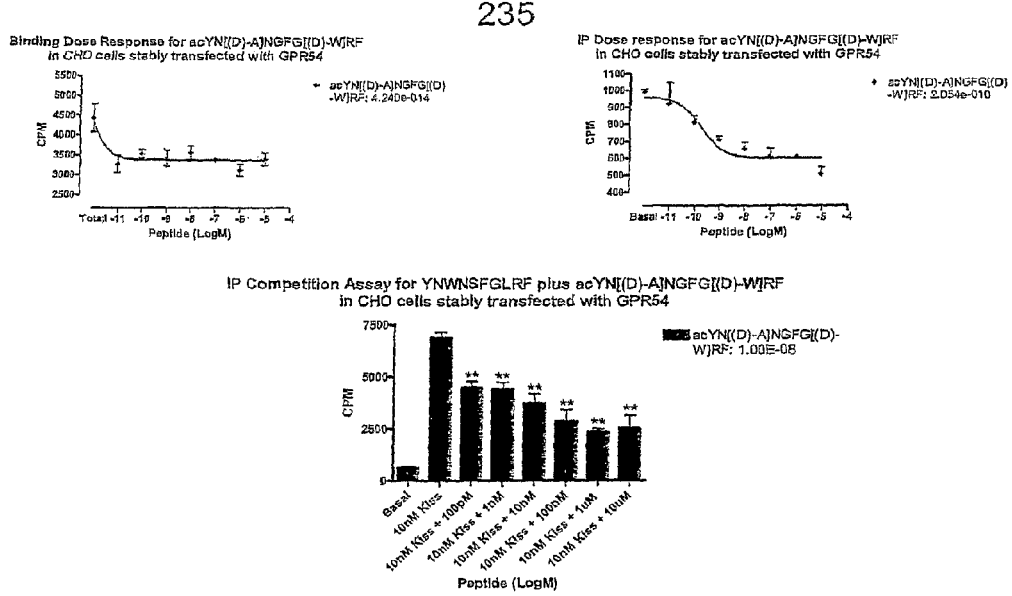
Figure 4:
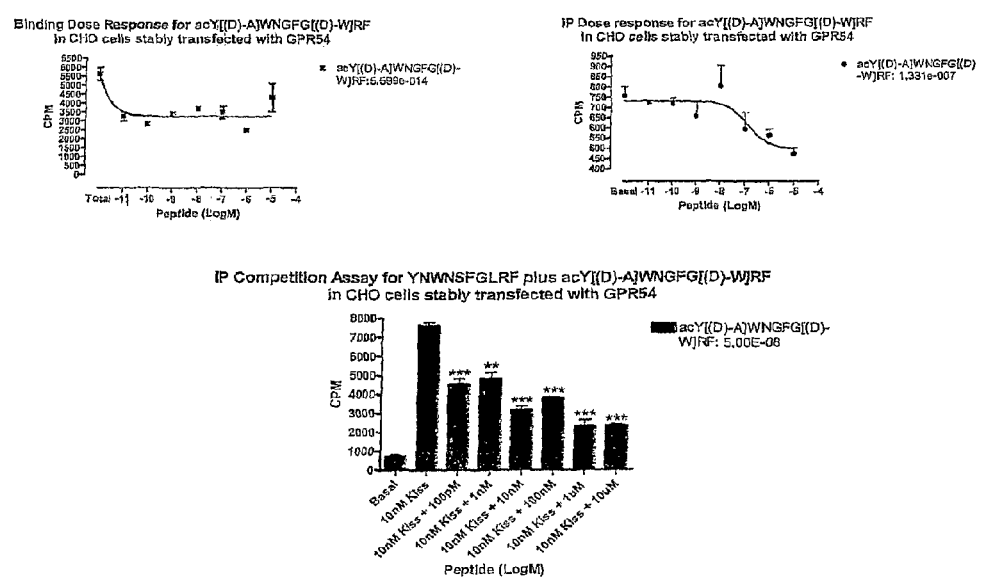
Figure 4:
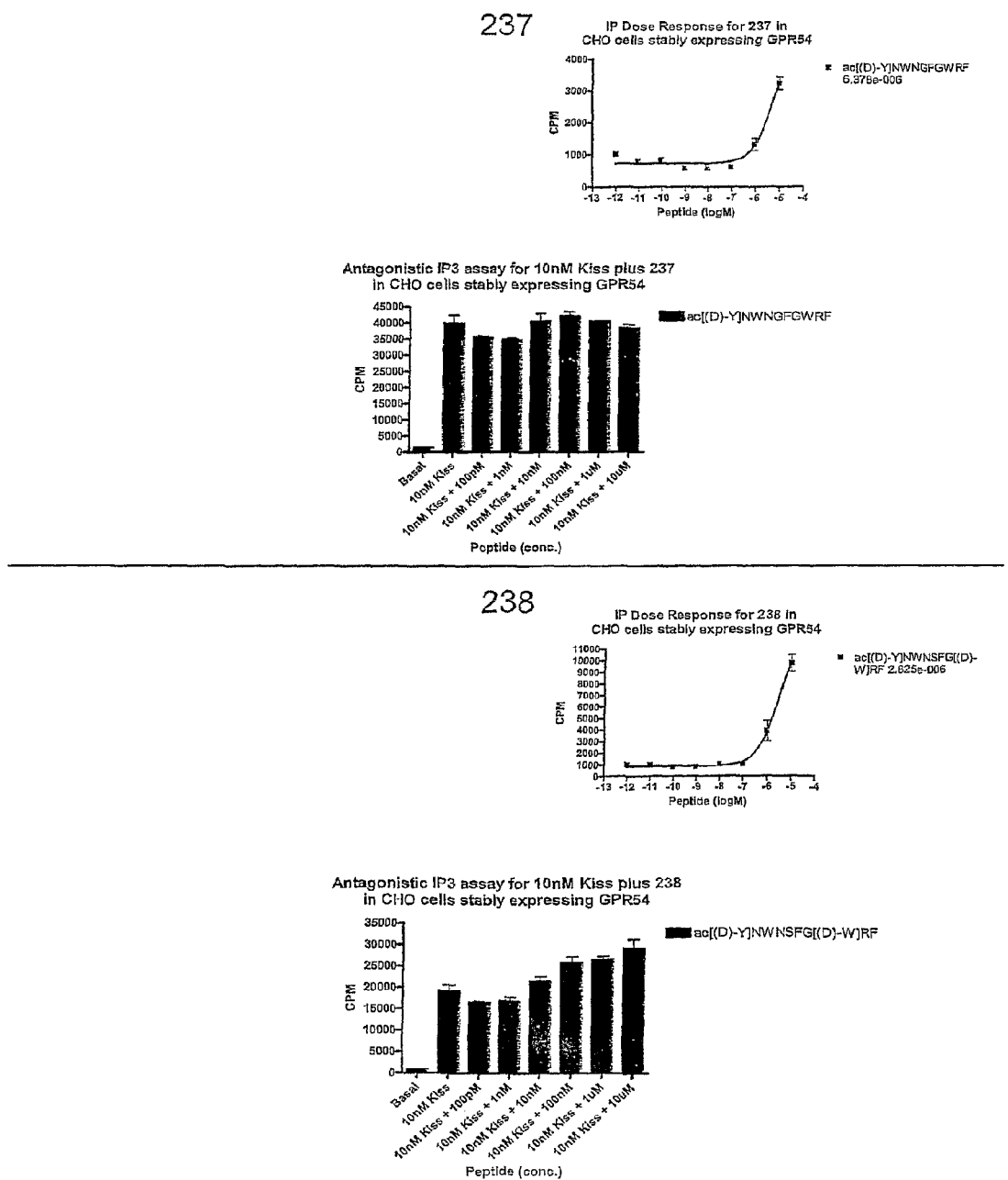
Figure 4:
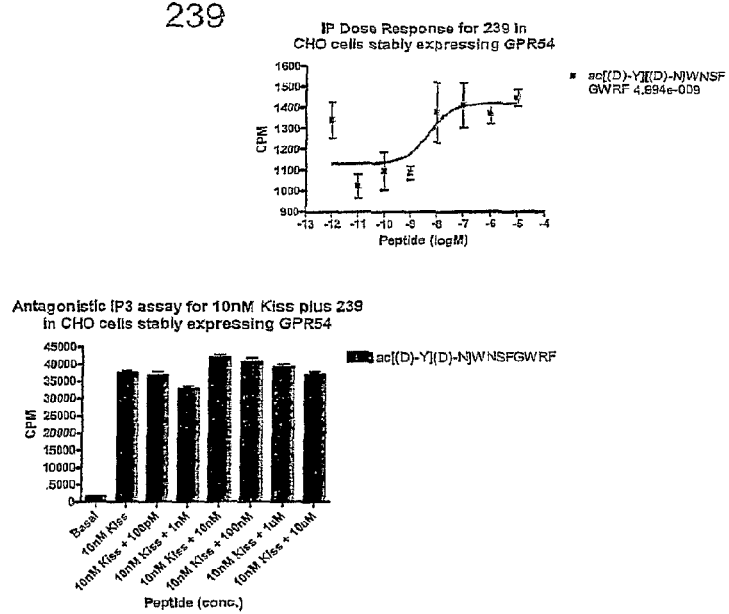
Figure 4:
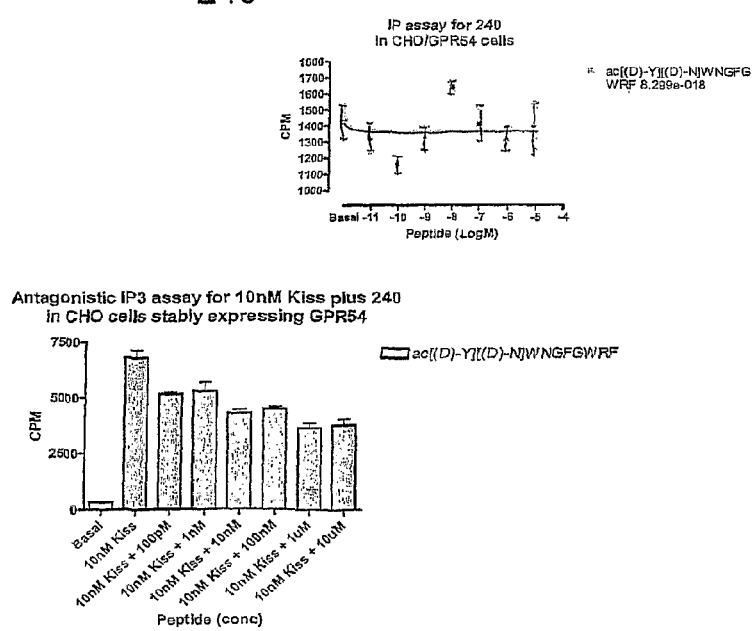
Figure 4:
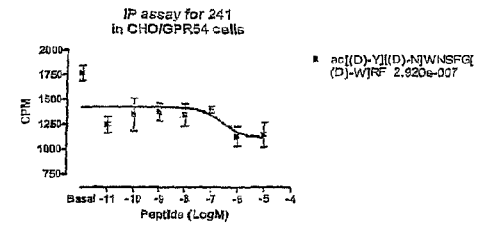
Figure 4:
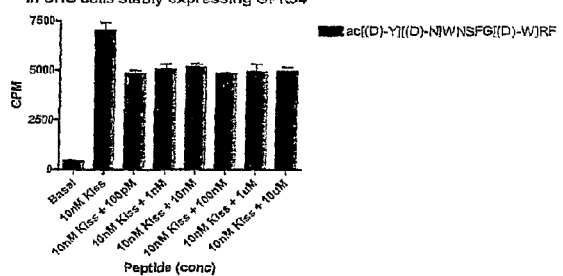
Figure 4:
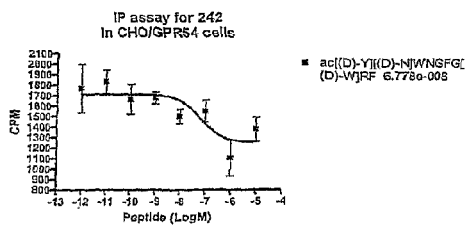
Figure 4:
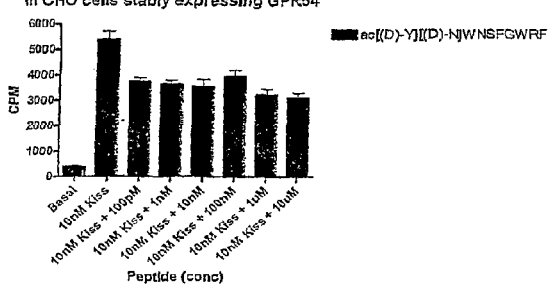
Figure 4:
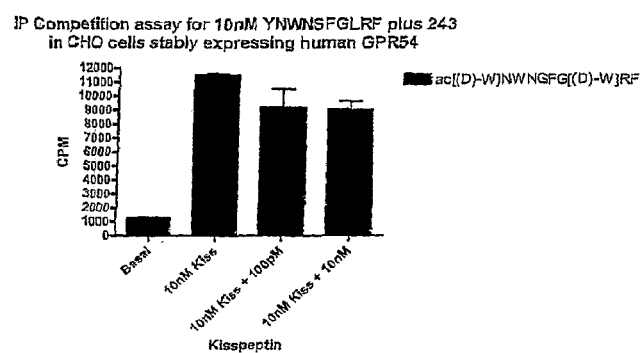
Figure 4:
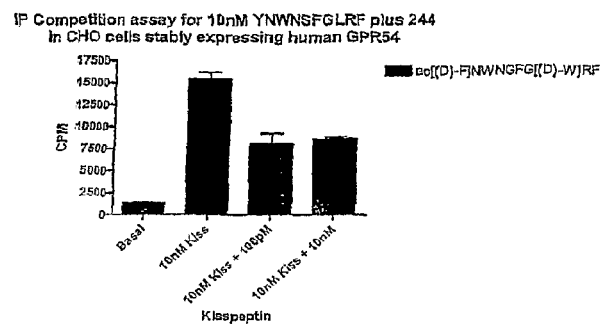
Figure 4:
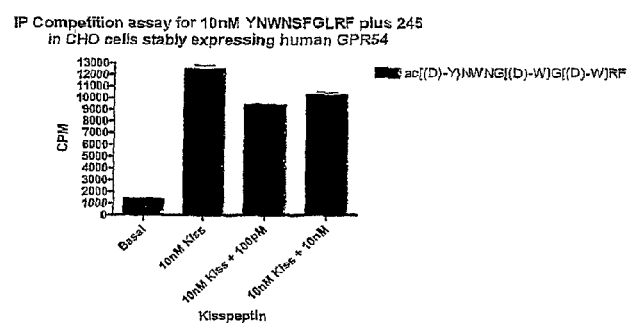
Figure 4:
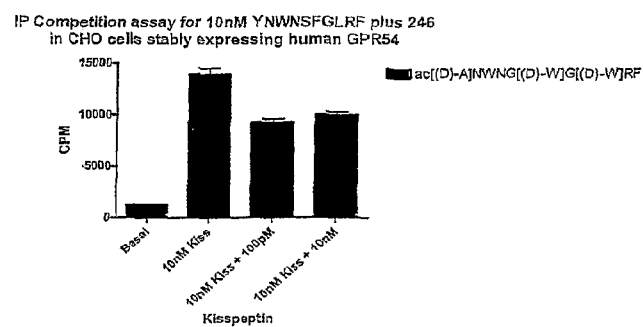
Figure 4:
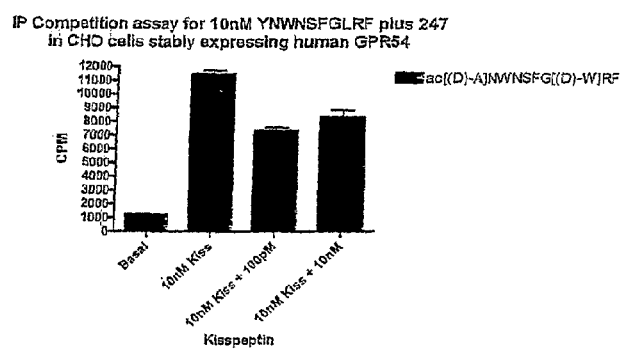
Figure 4:
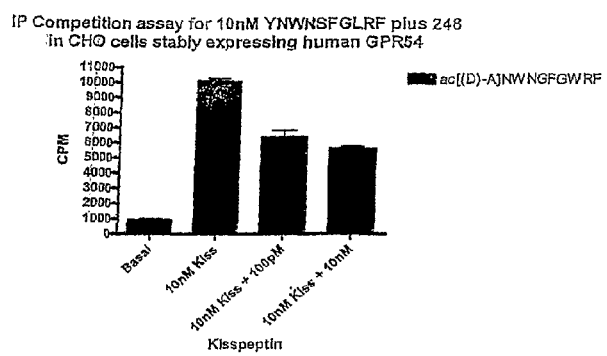

FIG. 4: Dose response binding curve and dose response IP curve and IP competition assays for peptide antagonists.

Figure 5:
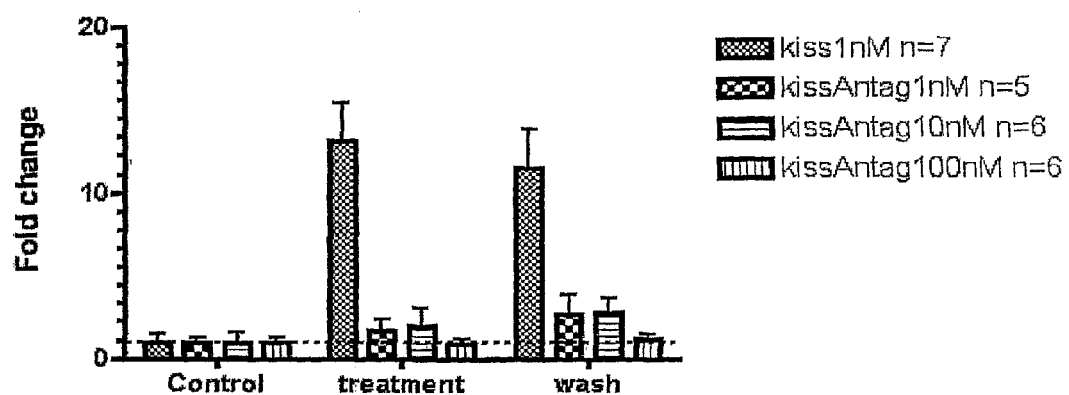

FIG. 5: Inhibition of kiss stimulation of GnRH neurone firing by antagonist 234.

Figure 6:
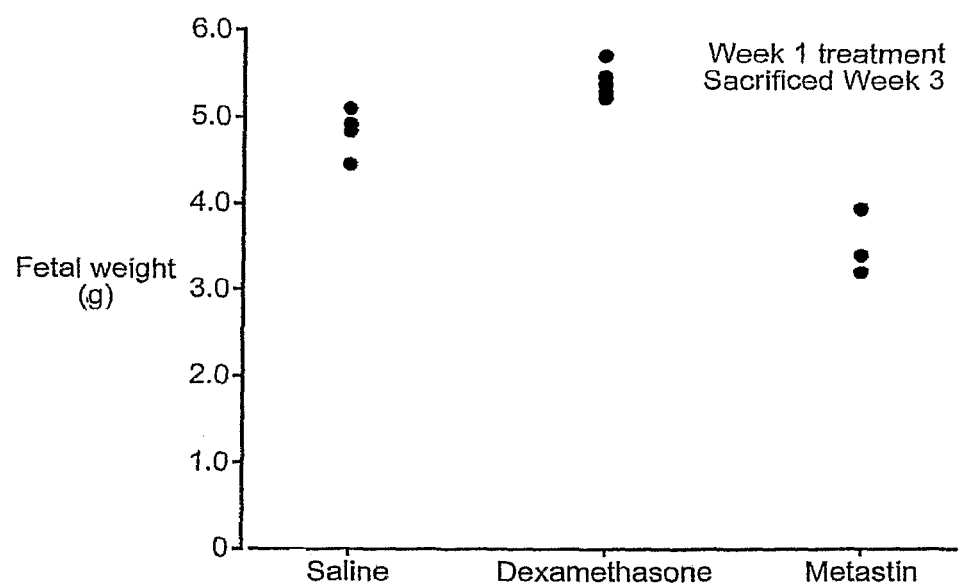

FIG. 6: Fetal weight is decreased by kisspeptin treatment which causes poor implantation. Therefore kisspeptin plays a role in fetal growth retardation suggesting that antagonists could be used to treat females with a history of poor implantation (which leads to, for example, miscarriage and pre-eclampsia).

Figure 7:
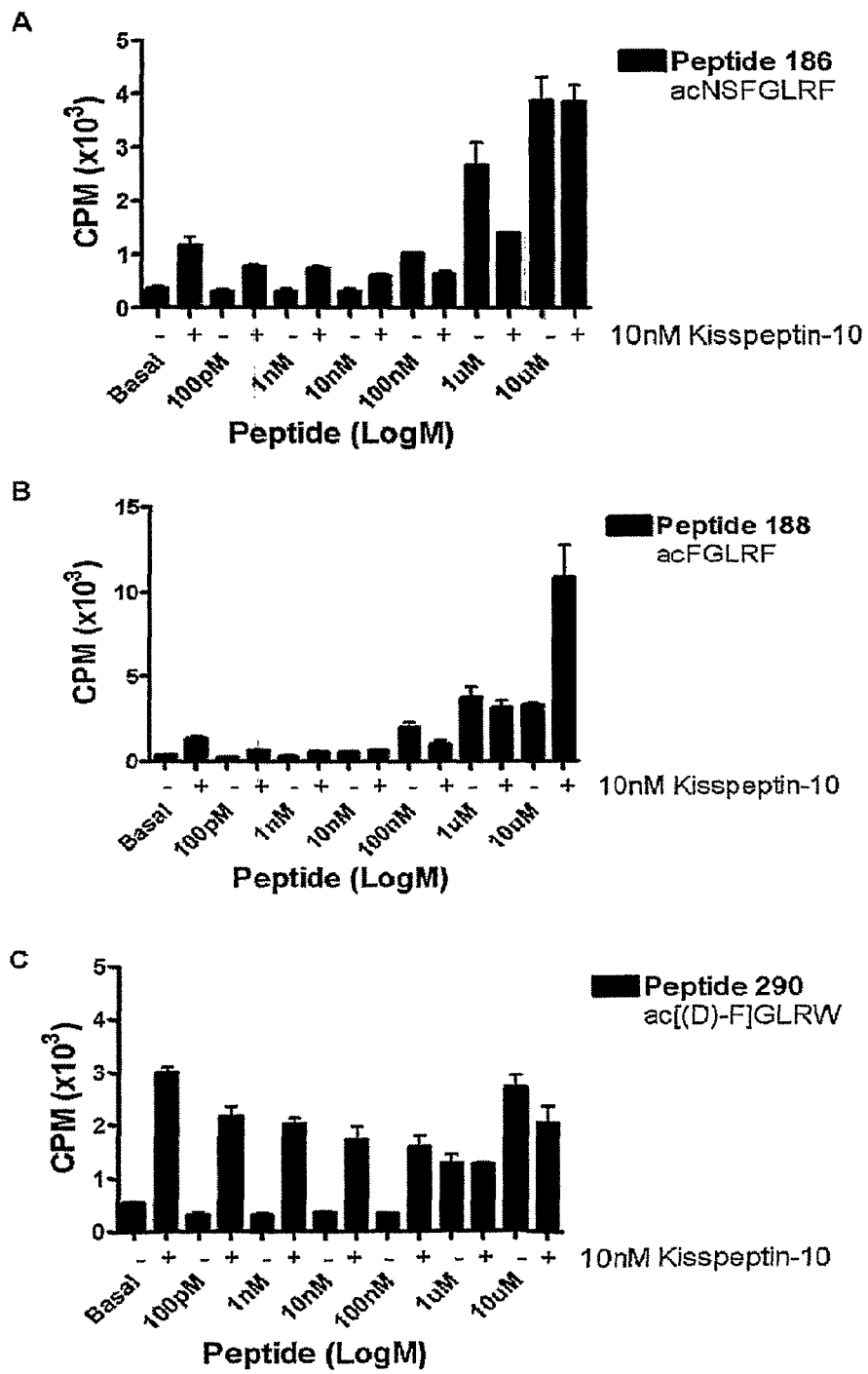

FIG. 7: N-terminal substitutions and C-terminal truncations create partial agonists. Amino acid substitutions were made at the N-terminus and truncations were made at the c-terminus of kisspeptin-10. Truncation to 7 amino acids (a) or 5 amino acids (b) in length caused partial agonism. When truncation to 5 amino acids was combined with (D)-Leu at Leu$^8$ this further enhanced the partial agonism (c).

Figure 8:
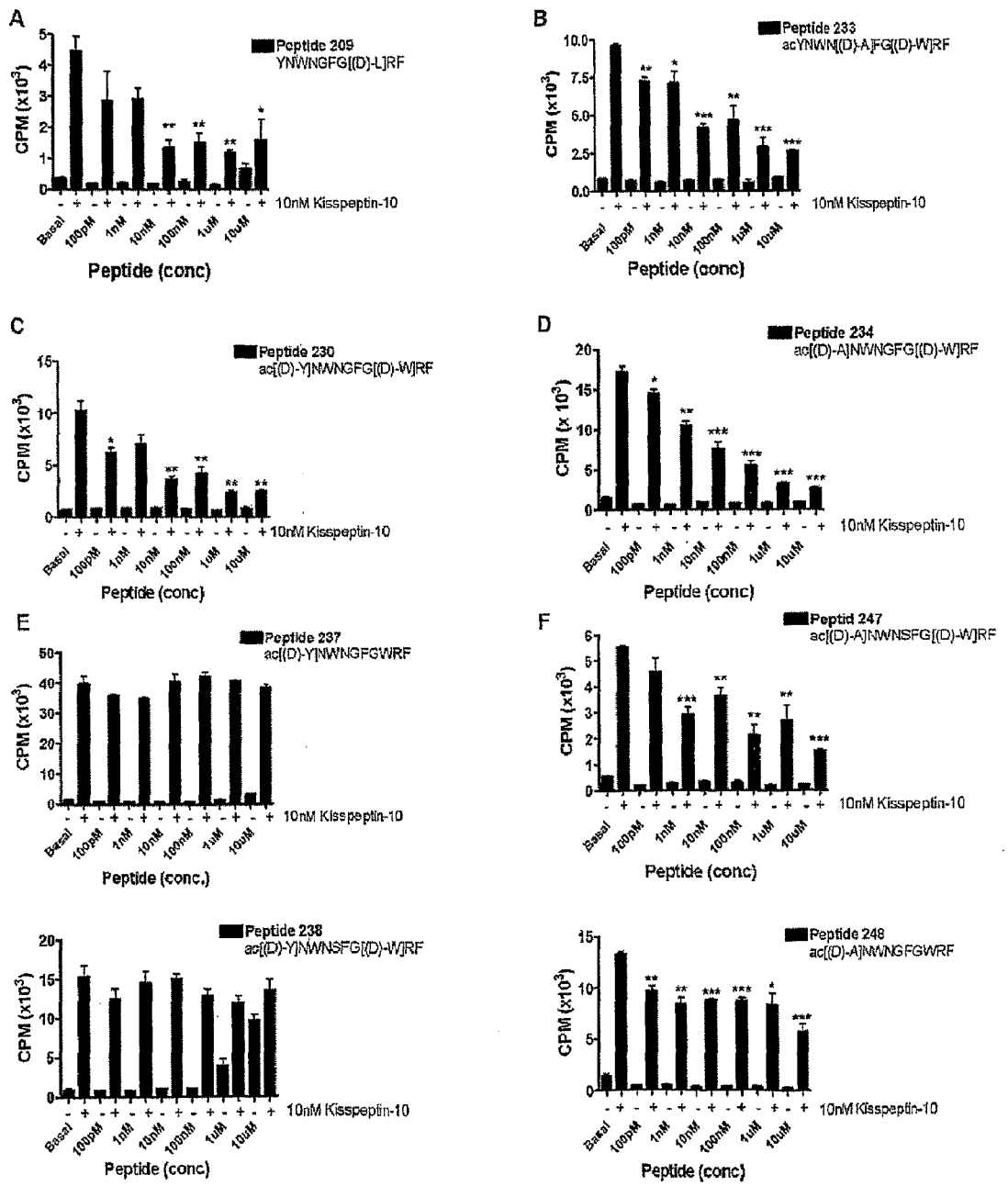

FIG. 8: Amino acid substitutions create antagonists at the human gpr-54 receptor with Gly5$^5$ and D-Trp$^8$ being critical. (a, b) Amino acid substitutions at serine$^5$ with glycine or D-Ala combined with substitutions at Leu$^8$ with D-amino acids created partial agonist. (c, d) Further substitutions at Tyr$^1$ with D-Ala or D-Tyr enhance this antagonism further to create full antagonists at the gpr-54 receptor. However, removal of Gly$^5$ and D-Trp$^8$ substitutions from antagonist with a D-amino acid at Tyr$^1$ decreases or abolishes antagonistic properties of analogues. (e) This is most pronounced when Tyr$^1$ is replaced with a D-Tyr as removal of one or both substitutions abolishes antagonism. (f) The effect is less obvious when Tyr$^1$ is replaced with D-Ala but antagonism is still reduced (*=p<0.05, =p<0.01, *=p<0.001).

Figure 9:
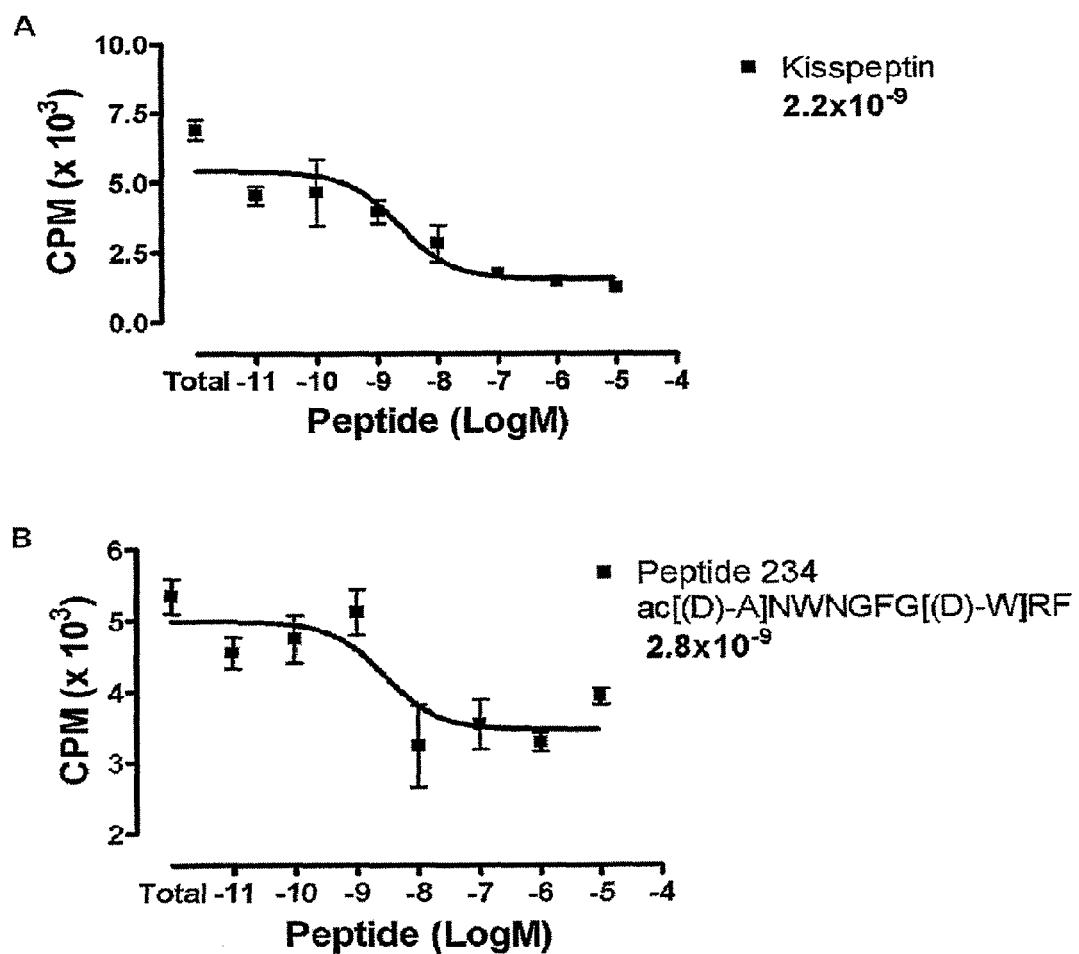

FIG. 9: Peptide 234 binds with the same affinity as Kisspeptin-10. When $I^{125}$-labelled kisspeptin-10 was competed with either kisspeptin-10 (a) or peptide 234 (b) they both bound with an affinity of 2 nM.

Figure 10:
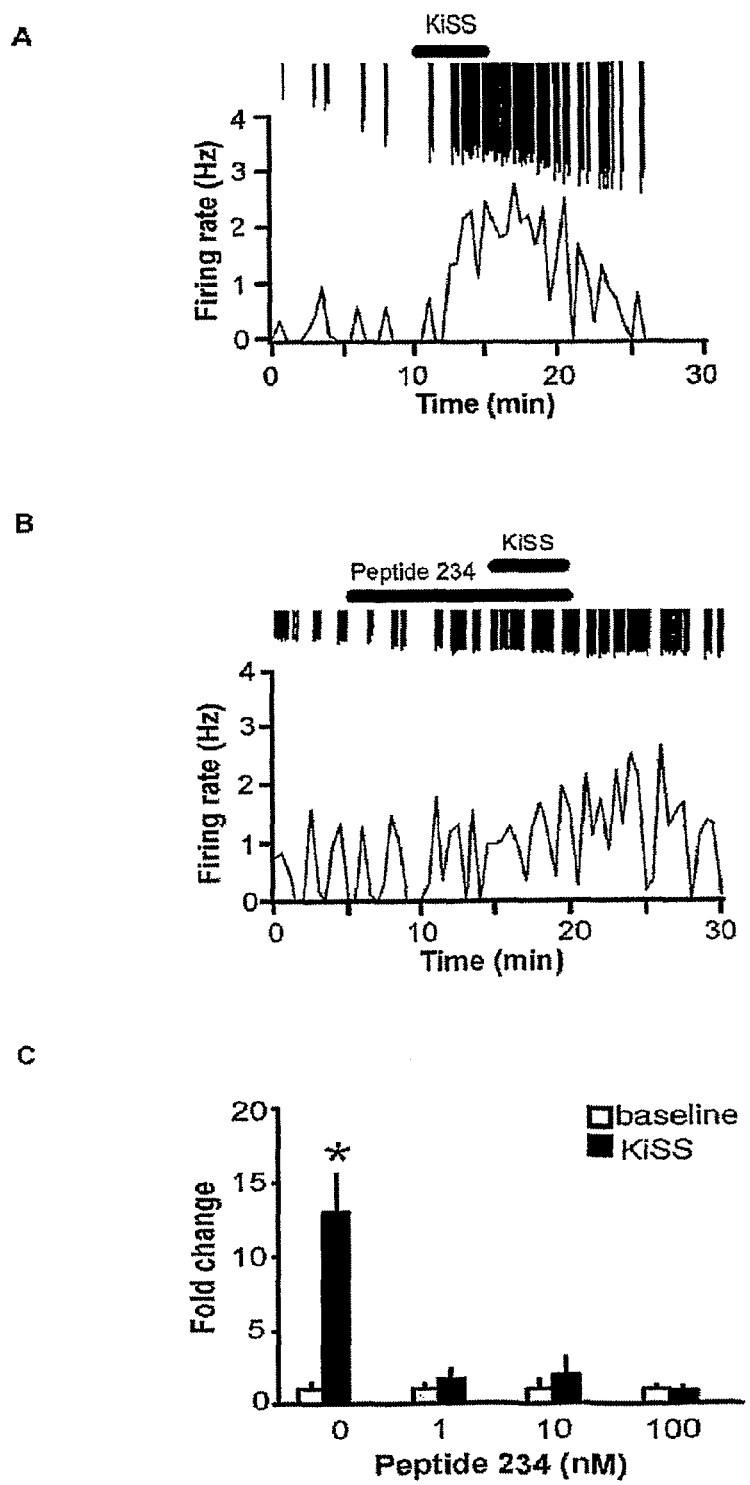

FIG. 10: Peptide 234 antagonizes kisspeptin-10 excitation of GnRH neurons.

Representative traces of GnRH neuronal firing rate over time. (a) Increased GnRH firing rate after 1 nM kisspeptin-10 (bar). Downward spikes are individual action currents. (b) Inhibition of kisspeptin-10 (1 nM) stimulation by peptide 234 (1 nM, bar). (c) Summary bar graph showing mean±SEM fold change in firing rate during baseline (white bars) and kisspeptin-10 (black bars) kisspeptin-10 significantly increased firing activity of GnRH neurons (n=7, * p<0.002). Response to kisspeptin-10 was significantly reduced with the presence of 1, 10, 100 nM peptide 234 (1 nM n=5, 10 nM n=6, 100 nM n=7, #p<0.001 all groups).

Figure 11:
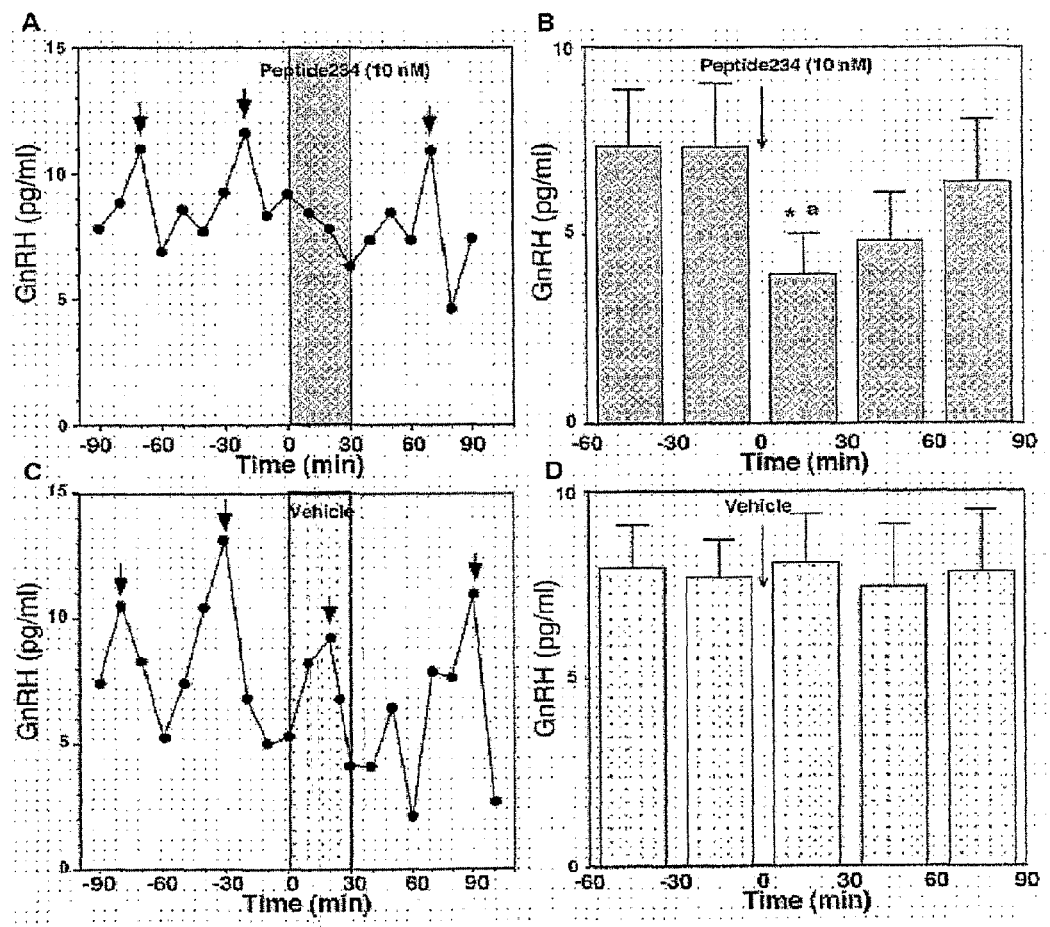

FIG. 11: Peptide 234 suppresses GnRH release in vivo. Representative cases from the effects of peptide 234 on GnRH release and group mean (±sem, n=6) are shown. (a) Pulsatile GnRH release in the hypothalamus was suppressed by 10 nM peptide 234 infusion to the stalk-median eminence regions (dark shaded bar). Short arrows indicate GnRH peaks identified by PULSAR. (b) In contrast, vehicle infusion as a control did not cause any significant changes in GnRH release (light shaded bar). (c) Data analysis indicated that peptide 234 significantly ($p<0.05$) suppressed GnRH release as compare to levels prior to peptide 234 as well as to the vehicle control. (d) Vehicle infusion did not cause any significant changes. The estimated concentration of peptide 234 in the stalk-median eminence region was 1 nM, based on our previous assessment that the dialysis membrane passes ~10% of peptides with a similar size. * $p<0.05$ vs. before peptide 234; a $p<0.05$ vs. control at corresponding time period.

Figure 12:
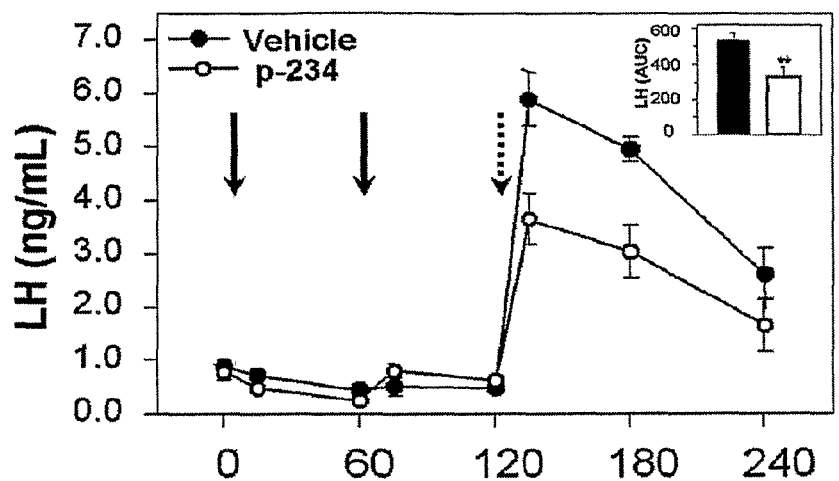
Figure 12:
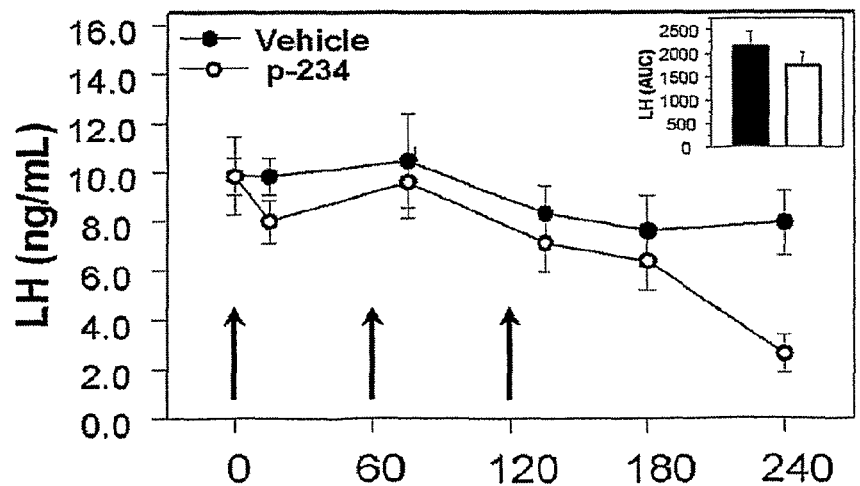

FIG. 12: Peptide 234 effects on basal and kisspeptin-10-stimulated plasma LH in intact and castrated male rats. Peptide 234 (a) inhibits kisspeptin-10 induced LH secretion in intact male rats. The animals were given two boluses of peptide 234 at 0 and 60 min, followed by one infusion of kisspeptin-10 at 120 mins. The peptide significantly inhibited LH production over the following 2 hours, calculated as area under the curve (AUC; $p<0.05$). Testosterone levels at 60 min after kisspeptin infusion (i.e., at 180-min of experiment) are also shown as bars. In addition, castrated male rats were given three infusions of peptide 234, which inhibited LH secretion (b).

Figure 13:
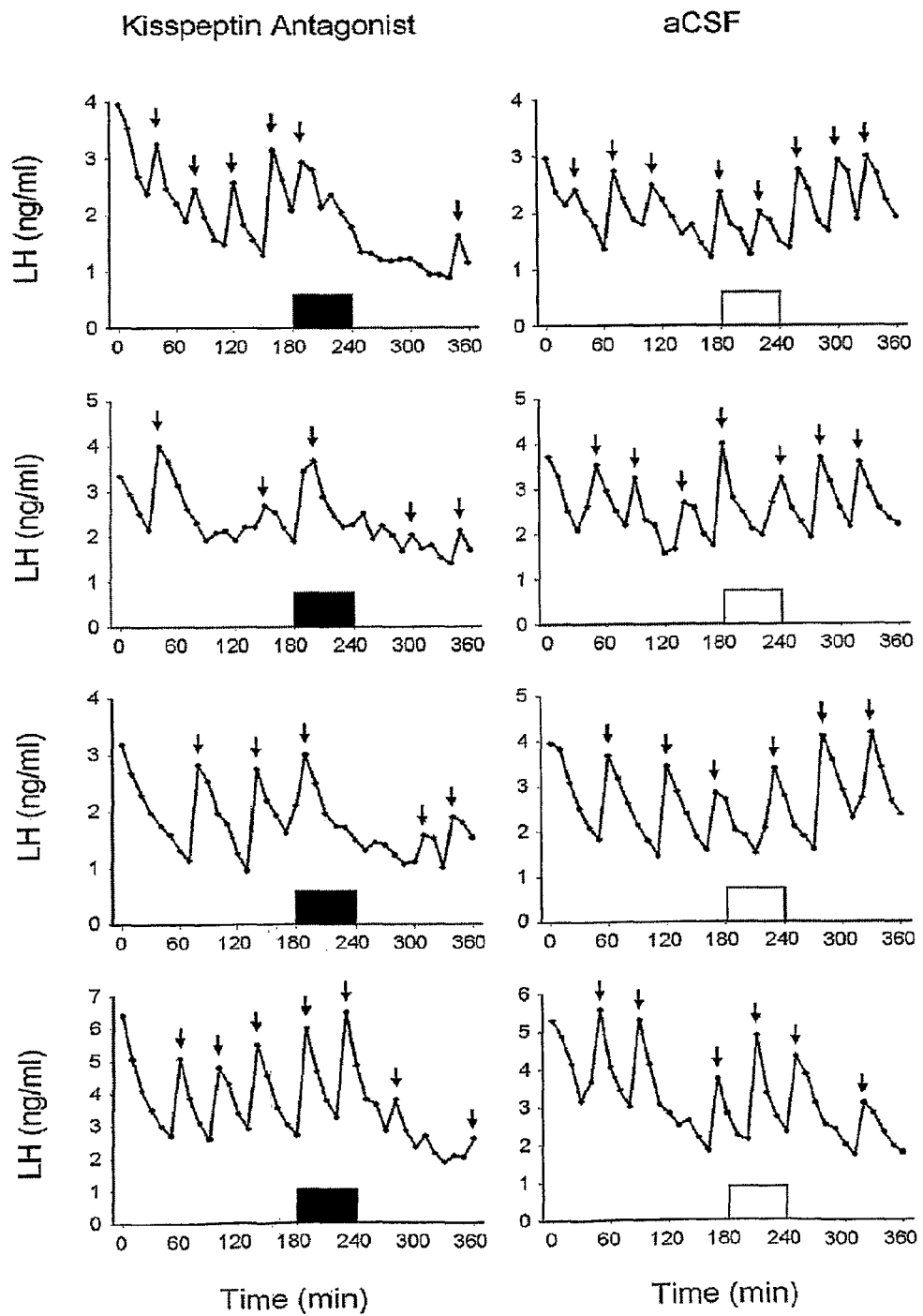

FIG. 13: Central infusion of peptide 234 inhibits the secretory pulses of LH in OVX ewes. Concentrations of LH are shown in ewes treated with peptide 234 (closed bars) or control (opened bars). Arrows indicate LH pulses as defined in the Materials and Methods. Analysis revealed a significant reduction in the mean LH concentration and pulse amplitude after peptide 234 infusion.

Table 2: Mean LH pulse amplitude, LH concentration, and GH concentration (ng/ml) before, during and after infusion with peptide 234. Data are the mean±SEM for vehicle and peptide-234 treated ewes before (0-180 min), during (180-240 min), and after (240-360 min) infusion. Repeated measures ANOVAs revealed a significant interaction between treatment and time ($P<0.05$). Individual P values for each time period are shown.

Figure 14:
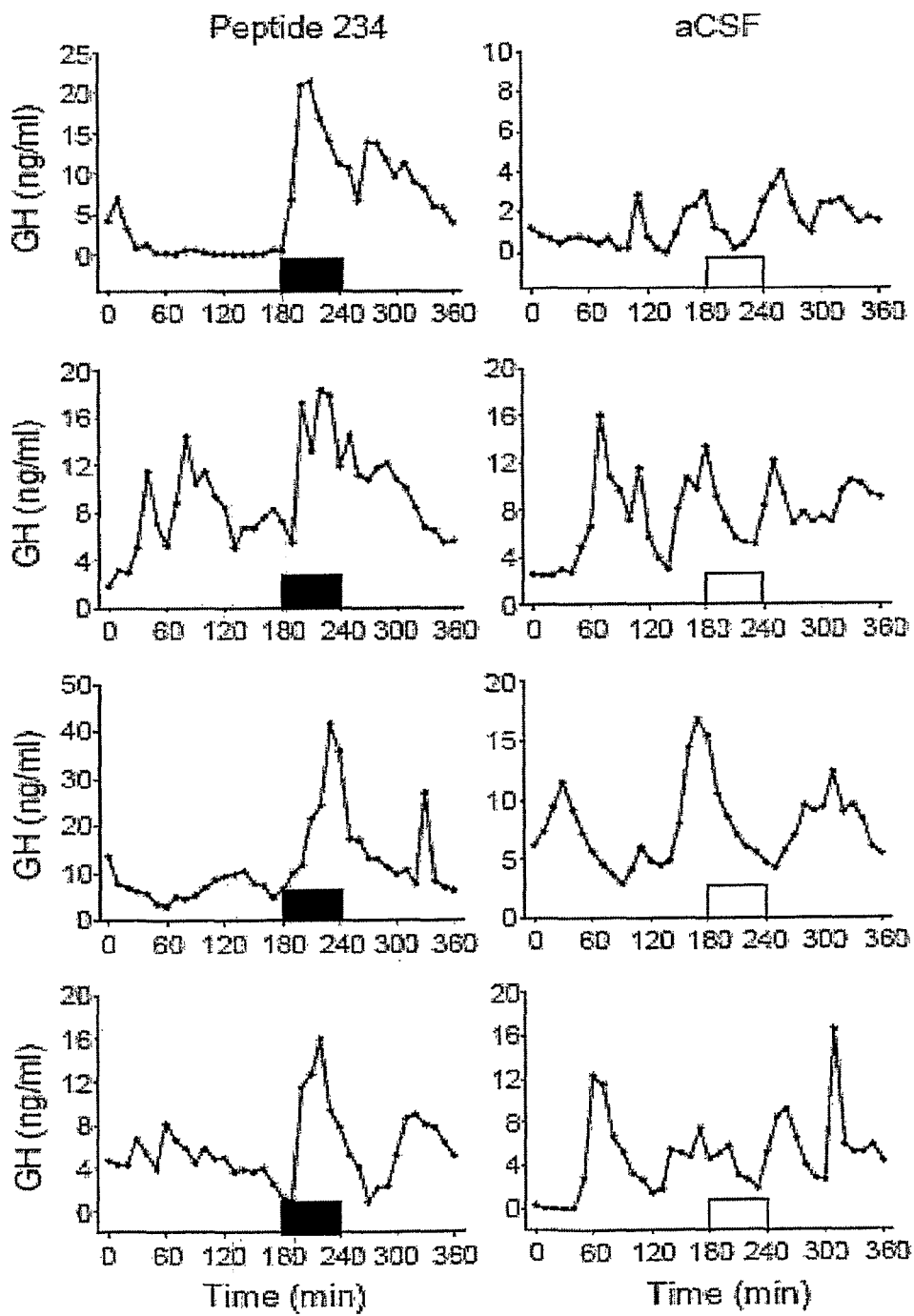

FIG. 14: Effect of central infusion of antagonist 234 on GH in OVX ewes. Concentrations of GH are shown in ewes treated with peptide 234 (closed bars) or control (opened bars). Analysis revealed a significant increase in the mean GH concentration during peptide 234 infusion.

Figure 15:
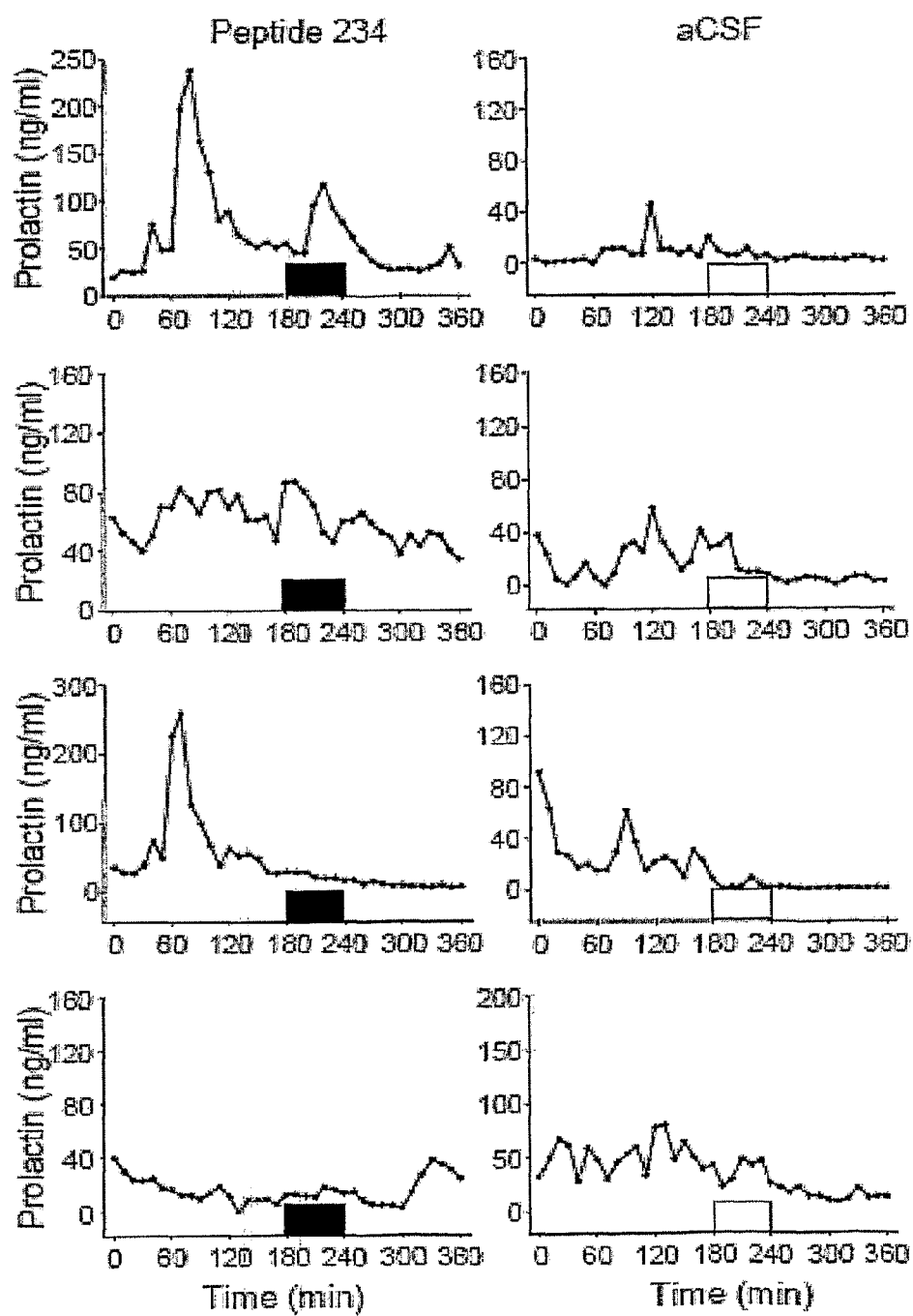

FIG. 15: Effect of central infusion of antagonist 234 on prolactin in OVX ewes. Concentrations of prolactin are shown in ewes treated with peptide 234 (closed bars) or control (opened bars). Analysis showed no effect of peptide 234 infusion on prolactin.

Figure 16:
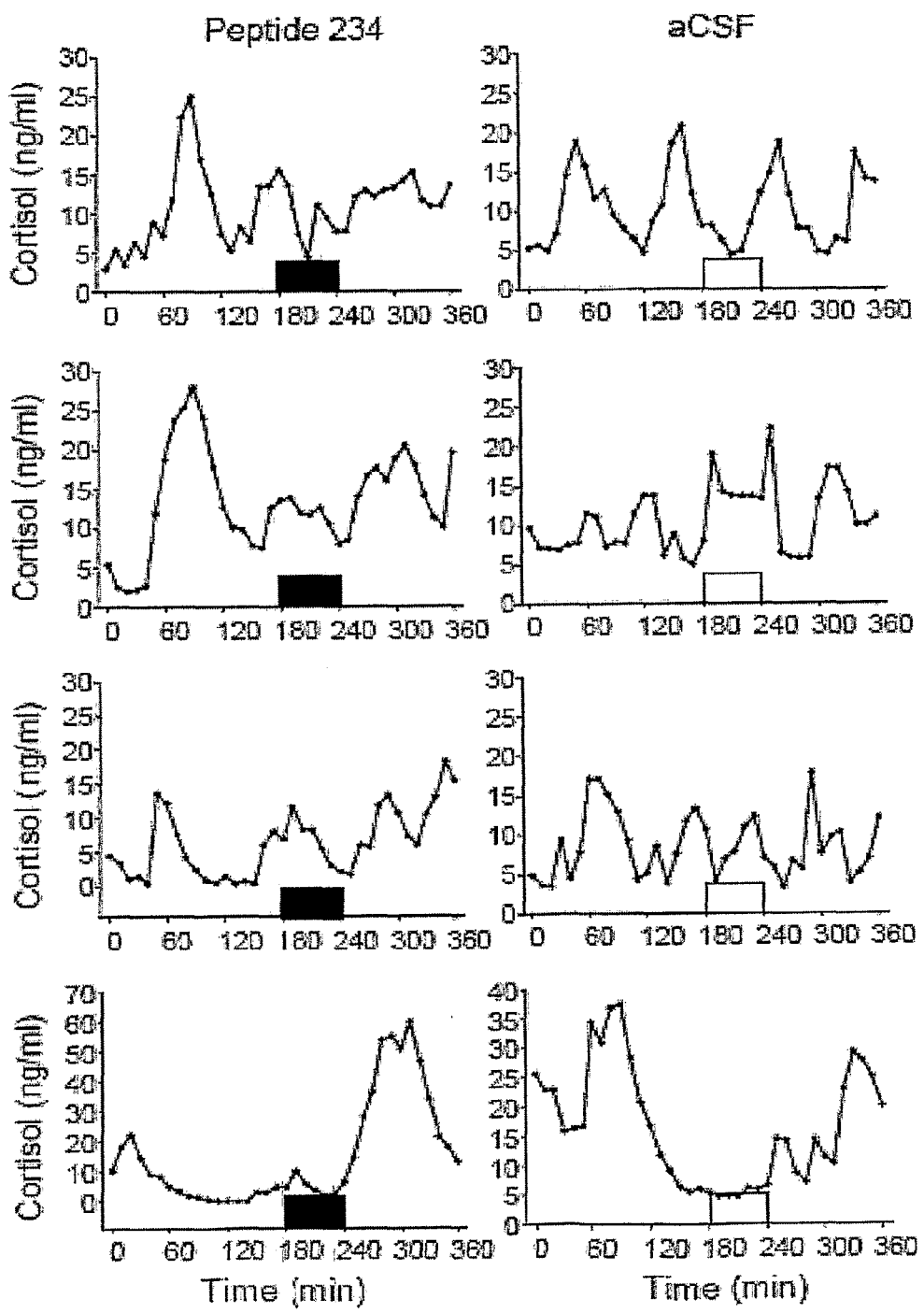

FIG. 16: Effect of central infusion of antagonist 234 on cortisol in OVX ewes. Concentrations of cortisol are shown in ewes treated with peptide 234 (closed bars) or control (opened bars). Analysis showed no effect of peptide 234 infusion on cortisol.

Figure 17:
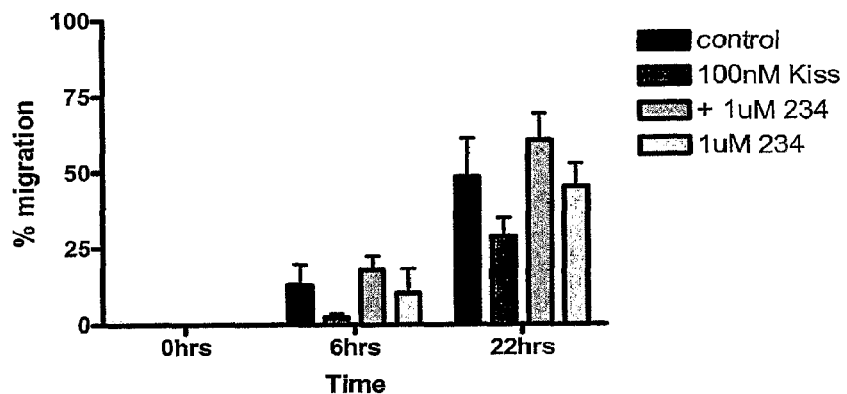
Figure 17:
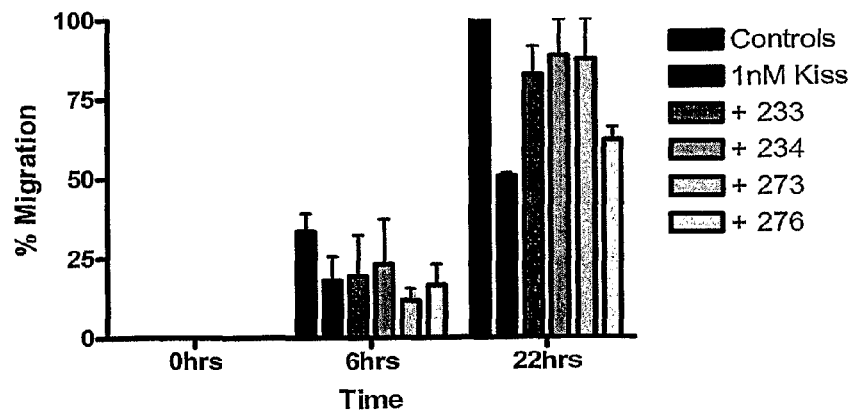

FIG. 17: Effect of antagonists on cell migration

Peptides 233, 234 and 273 act as antagonist in HUVEC and CHO cells at the human gpr-54, as they almost completely inhibit the effect of kisspeptin on migration. (A) In CHO (Chinese hamster ovary) cells, 100 nM Kisspeptin inhibits cell migration by 50%. Peptide 234 completely abolishes this inhibition. (B) In HUVECs (Human Umbilical Vein Endothelial Cells), 1 nM Kisspeptin inhibits migration in to the wound by 50%. However, in the presence of peptides 233, 234 or 273, inhibition is reduced to only 10%.

EXAMPLE 1

Experimental Data Relating to Kisspeptin Analogues

TABLE 1

| No. | | | | | Peptide Sequence | | | | | | |
|---|---|---|---|---|---|---|---|---|---|---|---|
| Kiss | | Y | N | W | N | S | F | G | L | R | F | NH$_2$ |
| 186 | | | | | ac | N | S | F | G | L | R | F | NH$_2$ |
| 187 | | Y | N | W | N | S | F | G | L | R | W | NH$_2$ |
| 188 | | | | | | ac | F | G | L | R | F | NH$_2$ |
| 189 | | | | | | ac | F | G | L | R | W | NH$_2$ |
| 190 | | | | | | ac | F | G | (D)-F | R | W | NH$_2$ |
| 191 | | | | | | ac | F | G | (D)-L | R | W | NH$_2$ |
| 200 | | | | | | ac | F | G | L | (D)-R | W | NH$_2$ |
| 201 | | | | | | ac | F | G | A | R | W | NH$_2$ |
| 202 | | | | | | ac | A | G | L | R | W | NH$_2$ |
| 203 | | | | | | ac | (D)-F | W | L | R | W | NH$_2$ |
| 206 | | | | | | ac | F | G | (D)-W | R | F | NH$_2$ |
| 207 | | | | | | ac | F | G | (D)-F | R | F | NH$_2$ |
| 208 | | Y | N | W | N | G | F | G | L | R | F | NH$_2$ |
| 209 | | Y | N | W | N | G | F | G | (D)-L | R | F | NH$_2$ |
| 210 | | Y | N | W | N | G | F | G | (D)-W | R | F | NH$_2$ |
| 211 | | Y | N | W | N | G | (D)-F | G | L | R | F | NH$_2$ |
| 212 | | Y | N | W | N | G | (D)-W | G | L | R | F | NH$_2$ |
| 213 | | Y | N | W | N | G | (D)-L | G | (D)-L | R | F | NH$_2$ |
| 228 | ac | Y | N | W | N | G | F | G | (D)-W | R | F | NH$_2$ |
| 229 | ac | Y | N | W | N | (D)-W | F | G | (D)-W | R | F | NH$_2$ |
| 230 | ac | (D)-Y | N | W | N | G | F | G | (D)-W | R | F | NH$_2$ |
| 231 | ac | Y | N | (D)-W | N | G | F | G | (D)-W | R | F | NH$_2$ |
| 232 | ac | Y | (D)-N | W | N | G | F | G | (D)-W | R | F | NH$_2$ |
| 233 | ac | Y | N | W | N | (D)-A | F | G | (D)-W | R | F | NH$_2$ |
| 234 | ac | (D)-A | N | W | N | G | F | G | (D)-W | R | F | NH$_2$ |
| 235 | ac | Y | N | (D)-A | N | G | F | G | (D)-W | R | F | NH$_2$ |
| 236 | ac | Y | (D)-A | W | N | G | F | G | (D)-W | R | F | NH$_2$ |
| 237 | ac | (D)-Y | N | W | N | G | F | G | W | R | F | NH$_2$ |
| 238 | ac | (D)-Y | N | W | N | S | F | G | (D)-W | R | F | NH$_2$ |

TABLE 1-continued

| No. | | | | | | | | | | | | |
|---|---|---|---|---|---|---|---|---|---|---|---|---|
| 239 | ac | (D)-Y | (D)-N | W | N | S | F | G | W | R | F | NH$_2$ |
| 240 | ac | (D)-Y | (D)-N | W | N | G | F | G | W | R | F | NH$_2$ |
| 241 | ac | (D)-Y | (D)-N | W | N | S | F | G | (D)-W | R | F | NH$_2$ |
| 242 | ac | (D)-Y | (D)-N | W | N | G | F | G | (D)-W | R | F | NH$_2$ |
| 243 | ac | (D)-W | N | W | N | G | F | G | (D)-W | R | F | NH$_2$ |
| 244 | ac | (D)-F | N | W | N | G | F | G | (D)-W | R | F | NH$_2$ |
| 245 | ac | (D)-Y | N | W | N | G | (D)-W | G | (D)-W | R | F | NH$_2$ |
| 246 | ac | (D)-A | N | W | N | G | (D)-W | G | (D)-W | R | F | NH$_2$ |
| 247 | ac | (D)-A | N | W | N | S | F | G | (D)-W | R | F | NH$_2$ |
| 248 | ac | (D)-A | N | W | N | G | F | G | W | R | F | NH$_2$ |
| 271* | ac | (D)-A | N | W | N | G | F | G | (D)-W | R | F | NH$_2$ |
| 273 | ac | (D)-A | N | W | N | (D)-S | F | G | (D)-W | R | F | NH$_2$ |
| 274 | ac | (D)-A | N | W | N | P | F | G | (D)-W | R | F | NH$_2$ |
| 275 | ac | (D)-A | N | W | N | (D)-P | F | G | (D)-W | R | F | NH$_2$ |
| 276 | ac | (D)-A | N | W | N | G | F | G | (D)-L | R | F | NH$_2$ |
| 277 | ac | (D)-A | N | W | N | (D)-A | F | G | L | R | F | NH$_2$ |
| 278 | ac | (D)-A | N | W | N | G | F | G | L | (D)-R | F | NH$_2$ |

| | IP stimulation | Inhibition of IP stimulation by 10 nM Agonist | | |
|---|---|---|---|---|
| No. | (IC50) | IC50 | P-Value | % Inhibition of Max |
| Kiss | 5.00E−09 | n/a | n/a | n/a |
| 186 | 1.50E−07 | ? | 0.028 | 70% |
| 187 | 4.00E−08 | none | n/a | 36% |
| 188 | 1.25E−07 | ? | 0.015 | 74% |
| 189 | 6.00E−08 | ? | 0.0063 | 94% |
| 190 | 2.00E−06 | 1.00E−08 | 0.0001 | 71% |
| 191 | 2.00E−05 | ? | 0.0001 | 79% |
| 200 | none | 3.00E−07 | 0.0012 | 63% |
| 201 | none | 7.00E−09 | 0.001 | 69% |
| 202 | >1.00E−04 | 1.00E−08 | 0.0112 | 64% |
| 203 | 1.50E−04 | 1.00E−10 | 0.0236 | 71% |
| 206 | none | 1.00E−08 | 0.0336 | 68% |
| 207 | none | none | n/a | 0% |
| 208 | 4.56E−08 | 1.00E−06 | 0.033 | 55% |
| 209 | none | 1.00E−07 | 0.0022 | 61% |
| 210 | none | <1.00E−10 | 0.0004 | 64% |
| 211 | 2.57E−06 | 1.00E−06 | n/a | 73% |
| 212 | 3.00E−04 | <1.00E−10 | 0.0013 | 68% |
| 213 | none | NONE | n/a | 38% |
| 228 | none | 5.00E−08 | 0.0001 | 58% |
| 229 | none | 8.00E−06 | <0.0001 | 68% |
| 230 | none | 5.00E−08 | 0.0013 | 81% |
| 231 | none | 1.00E−10 | 0.0275 | 55% |
| 232 | none | 3.00E−08 | <0.0001 | 75% |
| 233 | none | 2.00E−08 | <0.0001 | 80% |
| 234 | none | 7.00E−08 | 0.0001 | 93% |
| 235 | none | 1.00E−08 | 0.001 | 71% |
| 236 | none | 5.00E−08 | <0.0001 | 66% |
| 237 | 6.40E−06 | none | n/a | 0% |
| 238 | 2.80E−06 | none | n/a | 0% |
| 239 | 5.00E−09 | none | n/a | 0% |
| 240 | none | none | n/a | 39% |
| 241 | none | none | n/a | 24% |
| 242 | none | none | n/a | 15% |
| 243 | none | 1.00E−08 | 0.0029 | 55% |
| 244 | none | 1.00E−08 | 0.0004 | 60% |
| 245 | none | 1.00E−05 | 0.0015 | 66% |
| 246 | none | 5.00E−08 | <0.0001 | 80% |
| 247 | none | 8.00E−09 | 0.0006 | 80% |
| 248 | none | 5.00E−06 | <0.0001 | 64% |
| 271* | none | 5.00E−09 | <0.0001 | 57% |
| 273 | none | 4.00E−09 | 0.0002 | 79% |
| 274 | 5.30E−04 | 1.00E−10 | <0.0001 | 73% |
| 275 | 2.10E−08 | >1.00E−07 | 0.0083 | 44% |
| 276 | No IP | 1.00E−12 | 0.0013 | 65% |
| 277 | 1.50E−06 | 5.00E−11 | 0.0119 | 57% |
| 278 | No IP | >2.00E−07 | 0.0073 | 47% |

* = The sequence-RRMKWKKY is added to the N-terminus of 234 in this peptide

Materials and Methods
Method used for Dose response Bind (IC50) column in Table 1

Whole Cell Receptor Binding Assay—Kisspeptin-10 and analogues were prepared at 1:1000 dilutions in HEPES modified Dulbecco's modified Eagle's medium (DMEM) supplemented with $^{125}$I-labelled Kisspeptin to produce 100,000 counts per minute (cpm). Cell monolayers were placed on ice and exposed to 0.5 mls peptide (10 pM-1 uM); the cells were then incubated at 4° C. for 4 hr. After 4 hrs, cells were washed twice with ice cold Dulbecco's phosphate buffered saline (DPBS; with Calcium and Magnesium) and then 0.5 mls 0.1M Sodium Hydroxide (NaOH) were added to cells for 20 minutes, shaking to lyse cells. Lysates were transferred to plastic tubes and bound radioactivity counted on the gamma counter for 60 seconds. IC50s were measured as the concentration at which 50% of receptor binding was competed for by the analogue.

Method Used for Dose Response IP (EC50) Column in Table 1

Inositol-3-phoshate Stimulation Assay—Cell monolayers had 0.5 mls HEPES modified DMEM supplemented with 1% Penicillin/Streptomycin for 30 mins at 37° C. to block $IP_3$ breakdown. Cells were then stimulated with 0.5 mls Kisspeptin-10 and analogues (10 pM-1 uM) diluted at 1:1000 in the above media for 1 hr at 37° C., then in 10 mM Formic acid at 4° C. for 1 hr to lyse cells. Lysate was then transferred to plastic tubes containing 0.5 mls Dowex resin to bind the radioactive IP3 and the resin was then washed with 1 ml $H_2O$. The resin was then washed with 60 mM NH4 formate/5 mM Sodium tetraborate followed by 1M NH4 formate/0.1M Formic acid to release the bound radiation. Then 800 μls of the radioactive solution were transferred to scintillation vials containing 2.5 mls scintillation fluid and radioactivity counted on a Beta counter for 60 seconds. EC50s were measured as the concentration that stimulated a response at 50% of the maximum stimulation.

Method Used for Antagonist IP Inhibition (IC50) Column in Table 1

Inositol-3-phoshate Antagonistic Assay—Cell monolayers had 0.5 mls HEPES modified DMEM supplemented with 1% Penicillin/Streptomycin for 30 mins at 37° C. to block $IP_3$ breakdown. Cells were then stimulated with 0.25 mls 10 nM Kisspeptin-10 plus 0.25 mls of 10 nM Kisspeptin-10 or analogues (10 pM-10 uM) diluted at 1:1000 in the above media for 1 hr at 37° C., then in 10 mM Formic acid at 4° C. for 1 hr to lyse cells. Lysate was then transferred to plastic tubes containing 0.5 mls Dowex resin to bind the radioactive IP3 and the resin was then washed with 1 ml $H_2O$. The resin was then washed with 60 mM NH4 formate/5 mM Sodium tetraborate followed by 1M NH4 formate/0.1M Formic acid to release the bound radiation. Then 800 μls of the radioactive solution were transferred to scintillation vials containing 2.5 mls scintillation fluid and radioactivity counted on a Beta counter for 60 seconds. IC50s were calculated as the concentration required to inhibit 10 nM Kisspeptin-10 stimulation by 50%.

P-values were calculated using student's T-tests and the most significant value for each analogue is quoted.

IP stimulation refers to intrinsic residual agonist activity where estimateable.

IC50 is dose of antagonist required to inhibit to inhibit IP stimulation by 10 nM Kisspeptin-10 by 50%.

Central Kisspeptin Antagonist Treatment in OVX Ewes

All experimental procedures were conducted under a protocol approved by the Monash School of Biomedical Sciences "A" Animal Ethics Committee.

Adult Corriedale ewes were housed under natural lighting and were bilaterally ovariectomized (OVX) at least 1 month before any experimental manipulations. Permanent indwelling third cerebral ventricular (3V) cannulae were implanted in a subsequent surgical procedure as previously described (Barker-Gibb et al., 1995, *J. Endocrinol.*, 147:565-79). Approximately two weeks after 3V surgery, one external jugular vein was cannulated for blood sampling and animals housed in single pens; cannulae were kept patent with heparinized saline.

Ewes were assigned to two treatment groups (n=4 per group); kisspeptin antagonist (diluted in artificial cerebrospinal fluid, aCSF; 150 mM NaCl, 1.2 mM $CaCl_2$, 1 mM $MgCl_2$, 2.8 mM KCl) or control (aCSF only). The following day, infusion lines were connected to 3V cannulae and blood sampling commenced at 07.00 h. Samples were collected every 10 min. After 3 h of sampling, kisspeptin antagonist (or control) was infused into the 3V at a dose of 40 μg/h for 1 h, with an initial loading dose of 10 μg. Both kisspeptin antagonist and vehicle were infused at 200 μl/h for 1 h using Graseby® MS16A infusion pumps (Smiths Medical Australasia Pty. Ltd., Gold Coast, Qld, Australia). After infusion, 3V lines remained in place and blood sampling continued for a further 2 h (total of 6 h). Plasma was harvested immediately from samples, and frozen at −20 C until assayed.

Plasma LH concentrations were measured in duplicate, using the method of Lee et al. (1976, *J. Reprod. Fertil.*, 46:1-6) with NIH-oLH-518 as standard. Assay results were calculated using the program of Burger et al. (1972, *J. Lab. Clin. Med.*, 80:302-12). Assay sensitivity was 0.08 ng/ml and the intra-assay coefficient of variation was less than 10% over the range of 0.3-12.8 ng/ml. A pulse analysis of the LH data was performed based on the method described for GnRH (Clarke, 1993, *Endocrinology*, 133:1624-32).

Results

Central Kisspeptin Antagonist Treatment in OVX Ewes

Central infusion of kisspeptin antagonist appeared to inhibit the secretory pulses of LH in OVX ewes (FIG. 3). LH pulse analysis revealed in control treated OVX ewes—and in OVX ewes prior to kisspeptin antagonist treatment—the major secretory episodes of LH were clearly distinguishable. The number of secretory pulses was reduced after ventricular administration of kisspeptin antagonist. Where LH pulses were identified, these appeared to be of diminished amplitude.

EXAMPLE 2

Further Experimental Data Relating to Kisspeptin Analogues

TABLE 2

|  | Control | Peptide-234 | P Value |
|---|---|---|---|
| LH pulse amplitude (ng/ml) |  |  |  |
| Before Infusion | 1.46 ± 0.31 | 1.63 ± 0.28 | 0.71 |
| During Infusion | 1.84 ± 0.37 | 1.82 ± 0.52 | 0.98 |
| After Infusion | 1.68 ± 0.19 | 0.68 ± 0.05 | <0.01 |
| Mean LH (ng/ml) |  |  |  |
| Before Infusion | 2.70 ± 0.34 | 2.73 ± 0.43 | 0.96 |
| During Infusion | 2.44 ± 0.25 | 2.89 ± 0.55 | 0.50 |
| After Infusion |  |  | <0.05 |
| Mean GH (ng/ml) |  |  |  |
| Before Infusion | 4.70 ± 1.47 | 5.11 ± 1.48 | 0.85 |
| During Infusion | 5.32 ± 1.62 | 14.07 ± 2.78 | <0.05 |
| After Infusion | 6.34 ± 1.46 | 9.11 ± 1.44 | 0.23 |

Overview

Gonadotropin releasing hormone (GnRH) is the central regulator of the reproductive system and GnRH analogues are extensively employed for treating infertility and hormone-dependent diseases such as prostatic cancer and endometriosis. GnRH neuron activity is modulated by numerous factors, including photoperiod, nutrition, stress and steroid hormones. The discovery that mutations in gpr-54 cause hypogonadotropic hypogonadism led to the recognition that its cognate ligand (kisspeptin) mediates these effects on GnRH neurons. We report on the development of kisspeptin antagonists and their application in elucidating the role of kisspeptin in puberty and steroid hormone feedback. Substitution of amino acids in kisspeptin-10 identified a series of potent antagonists. A selected antagonist inhibited GnRH neuron firing in mouse brain and ablated GnRH pulses in pubertal female rhesus monkeys; the latter supporting the key role of kisspeptin in puberty onset. Moreover, the antagonist blunted the luteinizing hormone (LH) responses to exogenous kisspeptin in rats, and inhibited the LH increase after gonadectomy in ewes, rats and mice, which indirectly evidences that kisspeptin-neurons are targets for the feedback action of sex steroids. The development of kisspeptin antagonists thus provides novel tools for interrogating the physiological and pathophysiological roles of kisspeptin in the regulation of reproduction and therapeutics for intervention in hormone-dependent diseases.

Introduction

Gonadotropin-releasing hormone (GnRH) is the primary effector of gonadotropin secretion, which is critical for downstream regulation of gamete and steroid hormone production by the testes and ovaries. Neurons that produce GnRH are modulated by a host of factors, including photoperiod, metabolic signals, stress and gonadal steroids, which control GnRH secretion by activating or inhibiting neural circuits in the hypothalamus but the mechanisms transducing these effects into changes in GnRH secretion have remained elusive (1-3). These mechanisms are now emerging through the discovery of a unique type of infertility termed hypogonadotropic hypogonadism which was found to be associated with a mutation in a G protein-coupled receptor (gpr-54) (4, 5). Gpr-54 is the cognate receptor for a family of neuropeptides, called kisspeptins (6, 7), and kisspeptin/gpr-54 signaling has emerged as a linchpin in the neuroendocrine regulation of reproduction (8). Indeed, it has been revealed that kisspeptins (encoded by the Kiss1 gene) are potent secretagogues for GnRH and that GnRH neurons express the kisspeptin receptor (9, 10). Moreover, kisspeptin neurons have been implicated as conduits that relay environmental and hormonal inputs to GnRH neurons (11-16).

Through their modulation of the hypothalamic-pituitary-gonadal (HPG) axis, GnRH analogues are extensively employed to treat hormone-dependent diseases including prostatic, breast and ovarian cancers, endometriosis, uterine fibroids and precocious puberty, as well as in the induction of ovulation for infertility and IVF (17, 18). Since kisspeptin exerts such a powerful stimulatory effect on GnRH and gonadotropin secretion, intervention at the level of the kisspeptin/gpr-54 system may have potential for treatment of these conditions, and possibly with greater and more effective control than achieved with GnRH analogues.

Kisspeptin is markedly elevated in pregnancy (19) and is produced by the trophoblast (20) and inhibits trophoblast cell invasion (implantation) through gpr-54 receptors in trophoblast cells and in the uterine epithelium by inhibiting matrix metalloproteinases (MMPs) (21). Thus kisspeptin/gpr-54 dysregulation may play a role in placental and fetal pathologies such as pre-eclampsia, placenta acretia, ectopic pregnancy and inter-uterine growth retardation but direct evidence for this is lacking. Kisspeptin is also a potent vasoconstrictor through gpr-54 in selective regions of the human vasculature (22).

The development of kisspeptin antagonists would therefore provide the wherewithal to elucidate the role of kisspeptin in the positive and negative gonadal feedback on GnRH cells and in mediating metabolic and stress effects on the reproductive system. Kisspeptin antagonists also offer potential therapeutic intervention in a wide range of hormone-dependent diseases and possibly also in placental and vasculature dysfunction.

We report on a systematic structure-activity study of kisspeptin analogues and the development of potent and specific antagonists that are active in vitro and in vivo in laboratory rodents, sheep and a non-human primate. The studies indicate a pivotal role for kisspeptin in puberty and steroid hormone feedback underlining the wide utility of these antagonists Results Effects of Substitutions of Amino Acids within Kisspeptin-10 on Stimulation of Inositol Phosphate (IP) Release in CHO Cells Stably-Expressing Human gpr-54

As kisspeptin-10 is the minimal sequence required for full receptor binding and activation, we explored the effect of systematic substitution of amino acids in this region monitoring IP production in cells stably-expressing the human gpr-54. Because the C-terminal sequence $RF.NH_2$ is conserved in this large and ancient peptide family, we reasoned that this is essential for receptor binding and focused our attention on the preceding eight amino acids. We truncated the N-terminal five amino acids and introduced various substitutions with D-amino acids. This resulted in a reduced efficacy in IP production and a weaker ability to inhibit IP stimulation by 10 nM-kisspeptin-10 (FIG. 7; Table 1). This indicated the first five amino acids are involved in receptor activation. We then substituted residues alone or in combination in the full ten amino acid peptide, and monitored the effect this had on intrinsic IP stimulation and any inhibitory effects these substitutions had on IP stimulation by 10 nM kisspeptin-10. This systematic substitution of amino acids allowed us to develop a range of analogues with partial agonistic and antagonistic properties at this receptor (Table 1). Many of these analogues incorporated a glycine substitution for $Ser^6$ in combination with a D-amino acid (tryptophan or leucine) at $Leu^8$. Although these substitutions alone did significantly (P<0.01) inhibit 10 nM kisspeptin-10 stimulation of IP, they generally did not reduce this stimulation to basal levels (FIG. 8a,b; Table 1).

To develop full antagonists, further D-amino acid substitutions were made at $Tyr^1$, $Asn^2$ and $Trp^3$. The most effective antagonists with substitutions in these positions were peptides 230, 232, 233, 234, 235 and 236 which alone had little or no stimulation of IP, but had $IC_{50}$s of $<10^{-8}$M and a maximal inhibition of 66-93% of kisspeptin stimulation of IP (FIG. 8b-d; Table 1). The most complete inhibition was achieved with $D-Ala^1$ substitution (234 in Table 1; FIG. 8d). This combination of substitutions inhibited 10 nM kisspeptin-10 stimulation of IP by 93%, with an $IC_{50}$ of 7 nM and had no intrinsic IP stimulation, signifying high antagonist activity. These studies have also highlighted the significance of the glycine substitution at $Ser^6$ and the D-Trp at $Leu^8$, as removal of one or both of these substitutions from the above analogues either reduces the antagonist activity when D-Tyr is substituted at $Tyr^1$ (FIG. 8e) or reduces the antagonism when D-Ala is substituted (FIG. 8f). This suggests that these residues may be important for receptor activation. The active analogues displayed high binding affinities using $^{125}$I-kisspeptin-10, for example peptide 234 had a binding affinity of 2.7 nM (FIG. 9).

Peptide 234 Inhibits Kisspeptin-10 Stimulation of GnRH Neuron Firing

As has been demonstrated previously (23) (J. Pieleka-Fortuna, Z Chu, S M Meonter, Endocrine Society Meeting 2006, Abstract P1-8), 1 nM kisspeptin-10 markedly increased GnRH neuron firing activity (FIG. 10a,c). Under these experimental conditions, there was no effect on GnRH neuron firing activity of peptide 234 alone (1 nM pre 0.18±0.12 Hz, post 0.27±0.08 Hz, n=5, P>0.05; 10 nM pre 0.34±0.15 Hz, post 0.29±0.17 Hz, n=6, P>0.05; 100 nM pre 0.45±0.12 Hz, 0.62±0.14 Hz, n=7, P>0.05, paired t test). In contrast to the lack of effect of peptide 234 on basal firing, pretreatment with this peptide blocked the response to 1 nM kisspeptin-10 (P<0.001 for all doses) compared to cells treated with kisspeptin-10 alone (FIG. 10b, c).

Peptide 234 Inhibits Pulsatile GnRH Release in Female Rhesus Monkeys

Since peptide 234 inhibited GnRH neuronal firing we examined whether this resulted in an inhibition of GnRH release in pubertal female rhesus monkeys using methods previously described (24). Infusion of 10 nM peptide 234 over 30 min through a microdialysis probe located in the stalk-median eminence region promptly and consistently suppressed GnRH pulses as well as mean GnRH levels (FIG. 11a,c). In contrast, vehicle infusion through the probe did not cause any significant changes in GnRH release (FIG. 11b,d). The peptide 234-induced GnRH suppression was significantly different from values prior to peptide 234 infusion as well as those from the vehicle control (for both p<0.05). Based on our previous assessment that the dialysis membrane passes ~10% of peptides with a similar size (25), it is estimated that the concentration of peptide 234 in the stalk-median eminence region was 1 nM.

Peptide 234 Inhibits Kisspeptin-10 Stimulated LH in Intact Male Rats and the Increase in LH after Castration The effects of the putative kisspeptin antagonist activity of peptide 234 were tested in vivo using adult male rats. Pharmacological tests involved repeated (×3) intracerebral injections of the compounds and serial blood sampling, in order to assess potential effects of antagonists on basal LH levels. The third injection was accompanied by co-administration of a submaximal dose (100 pmol) of kisspeptin-10 and a 1 nmol dose of peptide 234, in order to monitor the ability to inhibit the kisspeptin-10 stimulation of LH and testosterone via its stimulation of GnRH. Administration of 1 nmol peptide 234 icv did not significantly modify basal LH levels at 15, 60, 75 and 120 min after injection, Central injection of 1 pmol kisspeptin-10 to vehicle-treated animals (at 120-min) evoked the expected rise in serum LH levels (FIG. 12a). In spite of its lack of effect on basal levels, co-administration of peptide 234 significantly blunted the LH secretory responses induced by central injection of kisspeptin-10, with a significant (P<0.01) reduction in the net LH secretory mass (AUC) during the 120-min period following co-injection of peptide 234 and kisspeptin-10. In good agreement, testosterone levels at 60-min after combined injection of peptide 234 and kisspeptin-10 were significantly (P<0.01) lower than in animals injected with kisspeptin-10 alone (FIG. 12a). LH levels were elevated in castrated rats over the 240 min monitoring period. Administration of 1 nmol peptide 234 at 0-, 60 and 120 min tended to reduce serum LH levels in castrated males; a reduction that reached statistical significance at 240 min (FIG. 12b).

Peptide 234 Inhibits LH Pulse Frequency and Amplitude in Ovariectomized Ewes

Major secretory episodes of LH were clearly distinguishable in control ovariectomized ewes and in treated ewes prior to peptide 234 administration (FIG. 13). The number of secretory pulses was reduced after ventricular administration of peptide 234. Where LH pulses were identified, these were of diminished amplitude following peptide 234 infusion (P<0.05, (Table 2). Mean LH levels were similar before and during the infusion, but reduced following peptide 234 infusion (P<0.05)

Infusion of peptide 234 significantly (P<0.05) increased the mean concentration of GH in OVX ewes (FIG. 14 and Table 2). This effect was only seen during the infusion, with mean GH levels similar between control and peptide 234 treated ewes before and after the infusion. Interestingly, this stimulatory effect appeared to be more immediate than the inhibitory effect on LH. Peptide 234 had no effect on the concentrations of prolactin or cortisol before, during or after infusion (FIGS. 15 & 16).

As can be seen in FIG. 15, antagonist administration surprisingly elevated growth hormone levels in sheep. Accordingly, the antagonists of the invention may be used to promote and/or induce growth hormone production in an individual. For example, the antagonists of the invention could be used alongside existing treatments in which growth hormone therapy is used, such as in the treatment of renal failure.

Peptide 234 Inhibits LH Pulse Frequency and Amplitude in Ovariectomized Ewes

Human Umbilical Vein Endothelial Cells (HUVECs) isolated from neonatal umbilical cord were used as they endogenously express gpr-54, which is though to be involved in cell migration in the placenta. Chinese hamster ovary (CHO) cells which stably express the human gpr-54 receptor were used as a model cell line for wound healing assays.

Cell monolayers of WT HUVECs or CHO cells stably expressing human gpr-54 had a scratch made down the middle of each well in a 12-well plate with a pipette tip, and then plates were washed with PBS to remove any loose cells. Complete media was added along with 1 nM Kisspeptin-10 for HUVECs and 100 nM Kisspeptin-10 for CHO cells, the optimal concentrations to inhibit cell migration (wound healing) in each cell type, in the presence and absence of antagonist 233, 234, 273 and 276 for HUVECs and 234 for CHOs. Cells were then incubated at 37° C. with 5% $CO_2$ in air for 22 hrs. Cells were photographed on the axiovert 2000 at 20× magnification in phase contrast (Hori et al., 2001. Metastin suppresses the motility and growth of CHO cells transfected with its receptor. Biochem Biophys Res Commun 286, 958-963; Stafford et al., 2002, Identification and characterization of mouse metastasis-suppressor KiSS1 and its G-protein-coupled receptor. Cancer Res 62, 5399-5404).

In FIG. 17(A), the results show that in the CHO cells, 100 nM Kisspeptin inhibits cell migration by 50% but that peptide 234 completely abolishes this inhibition. In FIG. 17(B), the results show that in the HUVECs, 1 nM Kisspeptin inhibits migration in to the wound by 50%. However, when this is done in the presence of peptides 233, 234 or 273 this inhibition is reduced to only 10%.

From this we can conclude that peptides 233, 234 and 273 act as antagonists in these cells at the human gpr-54 as they almost completely inhibit the effect of kisspeptin on migration. Accordingly, the antagonists of the invention can be used to induce and/or promote wound healing.

Addition of the Antennapedia Heptapeptide to the N-Terminus of Peptide 234

As discussed above, the R-R-M-K-W-K-K-Y (SEQ ID NO:20) sequence is a heptapeptide sequence from Antennapedia. The peptide sequence R-R-M-K-W-K-K-Y (SEQ ID NO:20) was added to the N-terminus of Peptide 234, and the resulting peptide designated Peptide 271.

Accordingly, Peptide 271 has the sequence:

(SEQ ID NO: 77)
ac.R-R-M-K-W-K-K-Y-(D)A-N-W-N-G-F-G-(D)W-R-F.z

As shown in Table 1, Peptide 271, which comprises the N-terminal Antennapedia heptapeptide, retains kisspeptin antagonist function.

Discussion

The pleiotropic effects of kisspeptin as an antimetastatic agent, and in regulating the HPG axis, and possibly implantation, vasoconstriction and CNS neurons makes the gpr-54 receptor an attractive therapeutic target. Until now the major emphasis has been on developing kisspeptin agonists as antimetastatic agents (26-28). However, the majority of therapeutic interventions in kisspeptin roles in the HPG axis, in implantation and in vasoconstriction would require development of antagonists. To realise this objective we have systematically substituted amino acids in the minimal kisspeptin structure required for biological activity (kisspeptin-10) and developed antagonists with high binding affinity and efficacy in vitro and in viva Studies in pursuit of kisspeptin agonists have established that $Phe^6$, $Arg^9$ and $Phe^{10}.NH_2$ constitute a binding pharmacophore (26). The evolutionary conservation of the $RF.NH_2$ moiety amongst a large and ancient family of peptides predicts that these C-terminal residues are essential for receptor engagement in agreement with their identification in the pharmacophore. Our pilot studies on kisspeptin amino acid substitutions confirmed that changes in the $RF.NH_2$ moiety may reduce binding. We therefore focused on other residues in seeking antagonist structures. We first truncated the N-terminal five amino acids in the rodent and human kisspeptin-10 sequences and found that this reduced agonist activity and antagonist properties. Substitution of $Phe^6$ or $Leu^8$ in these truncated peptides revealed that D-Trp substitution of $Leu^8$ produced the most promising antagonist. Incorporation of this substitution in the full decapeptide sequences produced better antagonists especially when accompanied by the substitution of $Ser^5$ with the achiral amino acid, Gly, which permits greater flexibility peptides and can obviate some of the steric hindrances of the other amino acid substitutions which have bulky side chains (e.g. D-Trp).

Further exploration revealed that substitution of the N-terminal $Tyr^1$ with D-amino acids was also tolerable for antagonistic activity but not if $D-Tyr^1$ or $D-Trp^1$ accompanied $D-Trp^8$ substitution. As expected substitution of the pharmacophore residue $Phe^6$ resulted in a decrease in agonist activity and generation of some antagonist activity (e.g. 211 and 212). However, substitution of $Phe^6$ with $D-Trp^6$ combined with $Leu^8$ substitution by $D-Trp^8$ reduced antagonism compared with $D-Trp^8$ alone (compare 213, 245, and 246 with 210). Certain substitutions of $Asn^2$ (e.g. in 232 and 236) and $Trp^3$ (e.g. in 231 and 235) were also acceptable for antagonism when combined with $D-Trp^8$ substitution of $Leu^8$. Overall a consensus sequence for antagonism was $X^1-X^2-X^3$-N-G-F-G-$X^8$-R-F.NH2 (SEQ ID NO:79) where $X^1$ is D-Tyr or D-Ala, $X^2$ is Asn or D-Ala or D-Trp, $X^3$ is Trp or D-Trp or D-Ala, and $X^8$ is D-Leu, D-Phe or D-Trp.

Our studies have also identified amino acids that appear to be involved in receptor activation as substitution of $Ser^6$, $Leu^8$ and to some extent $Tyr^1$, $Asn^2$ and $Trp^3$ contributed to antagonism. This is interesting because research to date suggests that the N-terminus contains the activation domain and the C-terminus the binding domain. Our findings suggest, however, that the two sites overlap, as it has been shown that $Phe^6$, $Arg^9$ and $Phe^{10}$ form a pharmacophore for binding (26), thus placing the $Leu^8$ activating residue within the binding site.

Of the analogues exhibiting good antagonist activity in vitro we selected peptide 234 for ex vivo and in vivo studies. Since kisspeptin action in the HPG axis is thought to be predominantly through stimulating GnRH secretion (10, 29) we first investigated the ability of peptide 234 to inhibit kisspeptin-10 stimulation of firing in GnRH neurons recorded in acutely prepared mouse brain slices. Peptide 234 was found to block kisspeptin-10 stimulation of GnRH neuron firing at 100 nM, 10 nM and even at 1 nM which is the same concentration as that of kisspeptin-10 used for stimulation of the GnRH neuron.

The inhibition of kisspeptin action on GnRH neuronal firing by peptide 234 suggests that the antagonist would reduce hypothalamic GnRH release in vivo. We therefore determined whether kisspeptin modified pulsatile GnRH release by administering peptide 234 directly to the stalk-median eminence region in pubertal female rhesus monkeys. The suppression of GnRH release during peptide 234 infusion provides the first direct evidence that input from kisspeptin neurons in the hypothalamus is a significantly important signal for GnRH release. The importance of kisspeptin in GnRH pulsatility is further supported by previous observations indicating that kisspeptin-54 release is pulsatile and kisspeptin-54 pulses coincide with GnRH pulses 75% of the time (24). However, because clinical studies suggest that patients with gpr-54 mutations exhibited attenuated LH pulses with an approximately normal pulse frequency (4, 5)' (30), the issue of whether kisspeptin neurons are critical for GnRH pulse-generation or if it is just a modulator of GnRH pulse amplitude, remains to be investigated. The complete ablation of GnRH pulses in the monkey model and LH pulses in the ovariectomised sheep may therefore simply reflect a total inhibition of amplitude rather than frequency.

Peptide 234 also blocked kisspeptin-10 stimulation of LH and testosterone in adult male rats over 2 hours (FIG. 12a), presumably by blocking kisspeptin-10 effects on GnRH secretion. The inhibition of GnRH secretion in intact female rhesus monkeys by peptide 234 suggests that the former explanation is most likely. In castrated male rats peptide 234 blocked the increase in LH that ensues following castration and the removal of negative feedback. The findings suggest that removal of gonadal steroids leads to a rise in kisspeptin activity that is translated into increased GnRH and LH secretion. Previous demonstrations of increased KiSS-1 gene expression in the arcuate nucleus in gonadectomised male and female rats (10, 29) and the ability to ablate the resulting LH rise with GnRH antagonist (10) is consistent with the presumption that kisspeptin-producing neurons are targets for the feedback actions of sex steroids (11). Levels of mRNA may not, however, reflect the biosynthesis and secretion of kisspeptin to engage gpr-54 in GnRH neurons. Our studies with a novel kisspeptin antagonist now provide direct evidence for kisspeptin modulation of the GnRH neuron in negative feedback by the gonads and emphasize the value of a kisspeptin antagonist for elucidating physiological mechanisms.

Frequent blood sampling (every 10 min) and antagonist treatment in ovariectomised ewes allowed us to interrogate the role of endogenous kisspeptin on LH pulse frequency and amplitude. LH pulse frequency and amplitude was markedly reduced by icy administration of peptide 234 suggesting a decrease in the amplitude and possibly frequency of GnRH secretion. This accords with our demonstration of peptide 234 inhibition of GnRH neuron firing rate in mice and its inhibition of GnRH pulses in rhesus monkeys. These findings imply that the endogenous secretion of kisspeptin is pulsatile in nature and drives the ultradian secretion of GnRH. The ability to increase GnRH neuron firing with kisspeptin-10 and to reduce it with kisspeptin antagonist suggests therapeutic potential of kisspeptin analogues in pathological conditions associated with dysfunctional LH pulse frequency such as the increased LH pulse frequency characteristic of polycystic ovary syndrome (31) and decreased frequency found in psychological disorders, stress (32) and in under nutrition (e.g., anorexia nervosa) (33).

Peptide 234 appears to be specific in its actions as it had no effect on prolactin and cortisol secretion in ovariectomised ewes (FIGS. 15 & 16) and did not bind to GnRH or LH receptors (data not shown). Growth hormone appeared to increase during infusion of peptide 234 in all 4 ewes suggesting that endogenous kisspeptin inhibits growth hormone (FIG. 14). We have not as yet examined this phenomenon in depth but have observed that the kisspeptin receptor (gpr-54) is exclusively expressed in growth hormone cells in the pituitary. Positive feedback by estrogen in inducing the LH surge of ovulation has been shown in rodents and sheep to be accompanied by an increase in Kiss-1 gene expression in specific hypothalamic areas (34-36).

Studies in female rats (37) and women (38) also show a greater LH sensitivity to exogenous kisspeptin at the time of the ovulatory LH surge suggesting that positive feedback by estrogen is mediated by increased kisspeptin input (37). This concurs with the demonstration of increased KiSS-1 gene expression after estrogen treatment (34, 35) and the LH surge, which is ablated by administration of kisspeptin antiserum (35) in female rats. We are currently utilizing peptide 234 to determine the role of kisspeptin in positive feedback on GnRH and LH secretion.

The majority of our studies administered antagonist icy in order to have a more direct intervention of kisspeptin input on GnRH neurons and more clearly delineate the role of kisspeptin in the physiological regulation of the HPG axis. Systemic administration is, however, a prerequisite for therapeutic application of kisspeptin analogues. Since intravenous and subcutaneous kisspeptin administration stimulate LH release in men (39) and women (38) the peptide evidently enters the brain or acts at sites that are outside the blood-brain barrier such as the arcuate nucleus or median eminence and acts on GnRH neurons. It therefore seems plausible that systemically delivered kisspeptin antagonist would also reach GnRH neurons or their axons in the median eminence, thus providing an effective and feasible therapeutic target.

A wide spectrum of pathologies is associated with dysfunction of the HPG axis and many conditions are exacerbated by sex steroid stimulation. These include infertility, polycystic ovary syndrome, endometriosis, uterine fibroids, excessive menstrual bleeding, delayed and precocious puberty, and breast, prostatic and ovarian cancers. The availability of potent, specific and efficacious kisspeptin antagonists will provide the potential for novel treatments of these conditions and for interrogating the physiological regulation of the HPG axis. In addition to these primary indications, kisspeptin antagonists may have potential in modulating vasoconstriction (22), CNS function (40) and trophoblast invasion and the developments of adequate maternal blood supply (19, 21, 41).

Methods
Peptides
Materials

Human kisspeptin-10 and peptide analogues 186-191, 200-203, 206-213 and 228-248 (10 μg) were custom synthesized by EZBiolabs. The source of all other reagents is indicated in the text.

In Vitro Assays for Antagonistic Activity
Cell Culture

Chinese hamster ovary (CHO) cells stably-expressing the human gpr-54 receptor (CHO/gpr-54) were obtained from Prof. G. Vassart, Univ. Brussels. The cells were maintained in Dulbecco's modified Eagle's medium (DMEM; Sigma) supplemented with 10% fetal calf serum, 2% glutamine and 1% penicillin (10,000 units/ml)/streptomycin (10,000 mg/ml) at 37° C. in a humidified 5% $CO_2$ atmosphere.

Inositol Phosphate (IP) Stimulation Assay

Prior to stimulation CHO/gpr-54 cells were washed twice with Dulbecco's phosphate-buffered saline (DPBS; without calcium or magnesium) then incubated overnight with $^3$H-myoinositol, labeled HEPES-modified DMEM with 1% penicillin/streptomycin at 37° C. HEPES-modified DMEM supplemented with 1% penicillin/streptomycin and 1% lithium chloride (0.5 ml) was added to cells for 30 min at 37° C. to block IP hydrolysis. Cells were then stimulated with 0.5 ml kisspeptin-10 and analogues (10 pM-1 μM) diluted at 1:100 in the above media for 1 h at 37° C., then with 10 mM formic acid at 4° C. for 1 h to lyse cells. Lysates were transferred to plastic tubes containing 0.5 ml Dowex resin to bind the radioactive IP and the resin was then washed with 1 ml water. The resin was next washed with 60 mM ammonium formate/5 mM sodium tetraborate. followed by 1M ammonium formate/0.1M formic acid to release the bound radiation. Then 800 μl of the radioactive solution were transferred to scintillation vials containing 2.5 ml scintillation fluid and radioactivity counted on a Beta counter for 60 sec. Experiments were repeated 3-5 times. IP production was plotted as mean values±SEM and analyzed by using a Student's t-Test ($p \geq 0.05$).

Inositol Phosphate (IP) Antagonism Assay

CHO/gpr-54 cell monolayers were stimulated with 0.25 ml kisspeptin (10 nM) alone or in combination with 0.25 ml peptide analogues (100 pM-1 μM), to investigate the inhibition of kisspeptin stimulation of IP production. Experiments were repeated 3-5 times. IP production was plotted as mean values±SEM and analyzed using a Student's t-Test ($p \geq 0.05$).

GnRH Neuron Firing
Animals

Firing of GnRH neurons were recorded in brain slices from transgenic female mice in which GFP is genetically targeted to GnRH neurons (42). Mice were housed on a 14 h light, 10 h dark cycle, with lights off at 1630 h, and were maintained on Harlan 2916 rodent chow (Harlan) and water ad libitum. All procedures were approved by the Animal Care and Use Committee of University of Virginia and were conducted within the guidelines of the National Research Council's Guide for the Care and Use of Laboratory Animals. Adult female GnRH-GFP mice were ovariectomized under isoflurane (Abbott Laboratories) anesthesia. Postoperative analgesia was provided by a long-acting local anesthetic (0.25% bupivicaine; 7.5 μl/site; Abbott Laboratories). At the time of surgery, mice received Silastic (Dow Corning) capsules containing 0.625 μg estradiol in sesame oil. Recordings were done 2-4 days after surgery in the AM, when estradiol has been demonstrated to have a negative feedback effect (43). No more than four cells from a single animal were recorded, all in different slices.

brain slice preparation

Brain slices were prepared using previously described method (44). Briefly, all solutions were bubbled with a 95% $O_2$/5% $CO_2$ mixture throughout the experiments and for at least 15 min before exposure to the tissue. The brain was rapidly removed and placed in ice-cold, high-sucrose saline solution containing 250 mM sucrose, 3.5 mM KCl, 26 mM $NaHCO_3$, 10 mM glucose, 1.25 mM $Na_2HPO_4$, 1.2 mM $MgSO_4$, and 2.5 mM $MgCl_2$. Coronal 300-μm brain slices were cut with a Vibratome 3000 (Technical Products, International, Inc., St. Louis, Mo.). Slices were incubated for 30 min at 30-32 C in a solution of 50% high-sucrose saline and 50% normal saline (NS) containing 135 mM NaCl, 3.5 mM KCl, 10 mM glucose, 1.3 mM $Na_2HPO_4$, 1.2 mM $MgSO_4$, and 2.5 mM $CaCl_2$ and then were transferred to a solution of 100% NS at room temperature and kept at least 30 min and no more than 6 h before recording.

Electrophysiological Recordings

Targeted extracellular recordings (also known as loose-patch) were used to study effects of kisspeptin-10 and peptide 234 on GnRH neuron firing activity (45). Because low resistance seals (<50 MΩ) do not influence the cell membrane this approach is a minimally invasive method for monitoring the endogenous electrical activity of a single cell. Although these events are not action potentials per se, they accurately reflect changes in the action potential firing rate. For simplicity, we have used the phrases firing rate, firing pattern, and/or firing activity to refer to these events.

Individual brain slices were placed in a recording chamber continuously superfused with oxygenated NS solution and kept at 29-31 C. Cells were visualized with an Olympus BX50WI upright fluorescent microscope with infrared differential interference contrast (Opelco). GnRH neurons were identified by brief illumination at 470 nm to visualize the GFP signal. Patch borosilicate pipettes (World Precision Instruments), which ranged from 1.5-3 ΩM were filled with normal HEPES-buffered solution containing 150 mM NaCl, 10 mM HEPES, 10 mM glucose, 2.5 mM $CaCl_2$, 1.3 mM $MgCl_2$, and 3.5 mM KCl. Pipettes were placed in contact with the GnRH neurons using an MP-285 micromanipulator (Sutter Instruments). Seal resistances ranged from 8 MΩ and either remained stable or increased during recording up to as high as 50 MΩ. Current traces were obtained using an EPC-8 amplifier (HEKA) with the PulseControl XOP (Instrutech) running in Igor Pro (Wavemetrics) on the G4 Macintosh computer (Apple Computer) to acquire data. A voltage-clamp mode with a pipette holding potential of 0 mV, filtering at 10 kHz, digitized with an ITC-18 acquisition interface (Instrutech) was used for the recordings.

Experimental Design

Human kisspeptin-10, 1 nM, (Phoenix Pharmaceuticals) was applied via the incubation bath. Different doses (1 nM, 10 nM, 100 nM) of peptide 234 were used to examine its antagonistic action on kisspeptin-10 activation of gpr-54. Positive control cells were recorded for a 10-min stable baseline, and then treated with kisspeptin-10 for 5 min, followed by a 15-min washout. Experimental cells were recorded for a 5-min stable baseline in NS, followed by 10 min in peptide 234 (1, 10 or 100 nM), then 5 min in kisspeptin-10 plus the same dose of antagonist, followed by a wash in NS. Washing with a solution containing antagonist yielded similar results (1 nM peptide 234, n=5 cells, not shown). One cell in the 10 nM peptide 234 group showed no activity; addition 15 mM KCl confirmed cell viability and recording integrity.

Data Analysis

Using programs written for Igor Pro, extracellularly-recorded events were counted and binned at 1-min intervals to identify changes in firing rate of GnRH neurons. Binned event data were analyzed using Microsoft Excel (Microsoft Corp) for the mean firing rate before kisspeptin-10 treatment (baseline, note this is during peptide 234 treatment in cells in the antagonist treatment groups) during kisspeptin-10 application (treatment), and during washout. For cells in the antagonist treatment group firing rates in NS vs. antagonist before kisspeptin-10 application were also compared. Mean firing rate was determined by dividing the total number of events detected by the duration of recording in each condition; two minutes were skipped after drug changes to eliminate transition periods. Since GnRH neuron firing activity changes with time (44, 45) the fold change for each treatment group was calculated. Groups were compared using ANOVA followed by Bonferroni post hoc test.

Effects of Peptide 234 on GnRH Release in Female Rhesus Monkeys

Animals

Four female rhesus monkeys, born and raised in the Wisconsin National Primate Research Center, were used in this study. They were housed in pairs (cages 172×86×86 cm) in rooms with 12 h of light 12 h of darkness and controlled temperature (22° C.). The animals were fed a standard diet of Harlan 20% Protein Primate Diet twice each day, supplemented with fresh fruit several times per week. Water was available ad libitum. The protocol for this study was reviewed and approved by the Animal Care and Use Committee, University of Wisconsin, and all experiments were conducted under the guidelines established by the NIH and USDA.

Experimental Design

The effects of peptide 234 on GnRH release were examined using the microdialysis method. This method allows collection of dialysate samples for GnRH measurement while peptide 234 was infused through the semi-permeable membrane, as described previously (25)'(24). Peptide 234 dissolved in CNS perfusion fluid was infused in the stalk median eminence region through the microdialysis probe for 30 min while dialysates were continuously collected. For a control, vehicle was similarly infused. Each animal was examined with peptide 234 (10 nM concentration) or vehicle at a random order in the same experiment with a 2 hour-minimum interval between two challenges. Two of the 4 animals were examined twice in separate experiments totaling 6 experiments. During the entire experiment monkeys were placed in proximity to a companion monkey, given constant access to food and water, and were provided frequently with fruit, cereal, raisins and other snacks. The mean age of sampling was 33.1±0.4 months.

Cranial Pedestal Implantation

For collection of perfusates in the stalk-median eminence region, we used the microdialysis method, as previously described (24). Prior to experiments, monkeys at 29.1±1.2 months of age (body weight: 3.6±0.1 kg) were well-adapted to the primate chair, experimental environment, and investigator. They were implanted with a cranial pedestal under isoflurane anesthesia, similar to those described previously for push-pull perfusion method (46). Animals were allowed to recover for at least 1 month prior to experimentation.

Microdialysis Methods

On the day of experiment the monkey was placed in the stereotaxic apparatus under ketamine (15 mg/kg b.w.) and medetomidine (0.03-0.05 mg/kg b.w.) anesthesia. The custom-made guide cannula (CMA 12) consisted of a stainless steel shaft (76.0 mm in length, 0.91 mm o.d.) and a removable stainless steel stylet (96.0 mm in length, 0.6 mm o.d.), which extruded 20 mm from the guide cannula tip. It was inserted into the skull 5 mm above the S-ME with a hydraulic microdrive unit (MO95-B). The microdrive unit allowed for accurate three-dimensional adjustment of the tip location. The x, y, and z coordinates for the S-ME were calculated using ventriculographs and the final radiographs taken during cranial pedestal implantation surgery. Cannula placement was confirmed with radiographic visualization. Following placement of the guide cannula, the monkey was removed from the stereotaxic apparatus and placed into a primate chair. Upon proper placement in the chair, the inner stylet was removed from the guide cannula and a custom-made microdialysis probe (a stainless steel shaft 96.0 mm in length, 0.6 mm o.d.), fitted with a membrane (5 mm in length, 0.5 mm o.d.), was inserted into the S-ME through the guide cannula as described previously (25)' (24). To reverse the effects of medetomidine, atipamazole (0.15-0.25 mg/kg) was injected (i.v.) into the animal. The animal was fully awake within 1 h after probe insertion.

A CNS perfusion fluid consisting of NaCl 147 mM, KCl 2.7 mM, CaCl2 1.2 mM, MgCl2 0.85 mM, purchased from CMA/Microdialysis with bacitracin (4 U/ml) added, was infused through the inflow tubing at 2 µl/min with the CMA/ 102 microdialysis pump outfitted with a 1 or 2.5 ml Hamilton gas tight syringe (Reno). Perfusates were continuously collected at 10 min intervals for up to 12 h through the outflow tubing into 12×75 mm borosilicate tube, on ice with a fraction collector (Model FC203B). The perfusate samples were immediately frozen on dry ice and stored at −80° C.

GnRH RIA

RIA was conducted with the antiserum R42 kindly provided by Dr. Terry Nett (Colorado State University), as described previously (46). Assay sensitivity was 0.02 pg/tube and intra and interassay coefficients of variation were 8.1% and 11.3%, respectively.

Data Analysis

Peaks of GnRH release were identified using the PULSAR algorithm as described previously (47). The mean value of a 30 min period of GnRH collection before and after peptide 234 (or vehicle) challenge was calculated in each experiment. Subsequently, the means (±sem) of all experiments during each time period were calculated for statistical comparison. The difference between before, during and after the treatment (within treatment) as well as between treatments (peptide 234 vs. vehicle) was examined using 2-way analysis of variance followed by Tukey's multiple comparison test. Differences were considered significant at P<0.05.

Dynamic Studies on Peptide 234 Inhibition of LH in Male Rats

Experimental Design

Adult male rats (BW: 280-310 g) bred in the vivarium of the University of Córdoba were used. The animals were maintained under constant conditions of light (14 h of light, from 0700 h) and temperature (22 C), and, before cannula implantation, were kept in groups of four rats per cage with free access to pelleted food and tap water. Experimental procedures were approved by the Córdoba University Ethical Committee for animal experimentation and were conducted in accordance with the European Union normative for care and use of experimental animals.

The animals were implanted with icy cannulae under light ether anaesthesia and caged individually thereafter. To allow delivery of compounds into the lateral cerebral ventricle, the cannulae were lowered to a depth of 4 mm beneath the surface of the skull; the insert point was 1 mm posterior and 1.2 mm lateral to bregma. Functional tests were conducted at least 24-48 h after cannula implantation.

Pharmacological tests in intact males involved 5 µl injections at 60 min intervals (icy) of 1 nmol doses of the peptide 234. The last injection was accompanied by the injection of an effective (but sub-maximal) dose of 100 pmol kisspeptin-10 (Phoenix Pharmaceuticals Ltd). Animals injected with vehicle (physiological saline) served as controls. Blood samples (250 µL) were taken by jugular venipuncture at 15- and 60-min following each icy injection. In addition, blood samples were taken immediately before initiation of the experiment (time: 0-min) and at 120-min after last injection (time: 240-min). Experimental procedures and kisspeptin doses were selected on the basis of previous studies (16, 34, 48). For each time-point, 10-12 samples were taken per group.

In addition, repeated icy injection of the peptide 234 was also conducted in orchidectomized (ORX) rats. The animals were subjected to bilateral ORX via the scrotal route, and after 1-wk after surgery were subjected to cannula implantation as described above. The test involved three intracerebral injections of the antagonist (1 nmol; at 0-, 60- and 120-min of the procedure) and blood sampling by jugular venipuncture in basal conditions (0-min) and 15-min after each icy injection. Additional blood samples were obtained at 180- and 240-min after central administration of peptide 234. For each time-point, 10-12 samples were taken per group.

Hormone Measurements

Serum LH levels were measured in a volume of 50 µl using a double-antibody method and radioimmunoassay kits supplied by the NIH (Dr. AF Parlow, NIDDK). Rat LH-I-10 was labeled with $^{125}$I using Iodo-Gen precoated tubes, following the instructions of the manufacturer (Pierce), and hormone concentrations were expressed using reference preparation LH-RP-3 as standard. Intra- and inter-assay coefficients of variation were below 8 and 10%, respectively. The sensitivity of the assay was 5 pg/tube. In addition, serum testosterone (T) measurements were selectively conducted in blood samples taken 60-min after co-administration of kp-10 and peptide 234 (Time: 180-min). To this end, a commercial kit from MP Biomedicals was used, following the instructions of the manufacturer. The sensitivity of the assay was 0.1 ng/tube and the intra-assay coefficient of variation was 4.5%. For each hormone, all samples were measured in the same assay. Accuracy of hormone determinations was confirmed by assessment of rat serum samples of known hormone concentrations used as external controls.

Data Analysis

Hormonal determinations were conducted in duplicate, with a minimal total number of 10 samples per group. When appropriate, in addition to individual time-point measurements, integrated LH secretory responses were calculated as the area under the curve (AUC), following the trapezoidal rule. Hormonal data are presented as mean±SEM. Results were analyzed for statistically significant differences using Student t-test or ANOVA followed by Student-Newman-Keuls multiple range test (SigmaStat 2.0). P≤0.05 was considered significant.

Effect of Peptide 234 on LH in Ovariectomised Ewes

Experimental Procedure

All experimental procedures were conducted under a protocol approved by the Monash School of Biomedical Sciences Animal Ethics Committee. Adult Corriedale ewes were housed under natural lighting and were bilaterally ovariectomized (OVX) at least 1 month before any experimental manipulations. Permanent indwelling third cerebral ventricular (3V) cannulae were implanted in a subsequent surgical procedure as previously described (49). Approximately 2 weeks after 3V surgery, one external jugular vein was cannulated for blood sampling and animals housed in single pens; cannulae were kept patent with heparinized saline. Ewes were assigned to two treatment groups (4/group); peptide 234 (diluted in artificial cerebrospinal fluid, aCSF; 150 mM NaCl, 1.2 mM $CaCl_2$, 1 mM $MgCl_2$, 2.8 mM KCl) or control (aCSF only). The following day, infusion lines were connected to 3V cannulae and blood sampling commenced at 07.00 h. Samples were collected every 10 min. After 3 h of sampling, peptide 234 (or control) was infused into the 3V at a dose of 40 µg/h for 1 h, with an initial loading dose of 10 µg. Both peptide 234 and vehicle were infused at 200 µl/h using Graseby® MS16A infusion pumps (Smith Medical Australasia Pty. Ltd.). After infusion, 3V lines remained in place and blood sampling continued for a further 2 h (total of 6 h). Plasma was harvested immediately from samples, and frozen at −20 C until assayed.

Plasma LH concentrations were measured in duplicate, with NIH-oLH-S18 as standard (49). Assay sensitivity was 0.1 ng/ml and the intra-assay coefficient of variation was less than 10% over the range of 0.3-12.8 ng/ml. Pulse analysis of the plasma LH data was as previously described (36). Plasma samples were assayed for GH in duplicate using the standard NIDDK-oGH-I-4 and NIDDK-anti-oGH-2 antiserum (50). The assay sensitivity was 1 ng/ml, the intra-assay CV was less than 10% between 4 and 51 ng/ml and the inter-assay CV was 20%.

Plasma prolactin concentrations were measured in duplicate using Sigma, Lot 114F-0558, NOL-7135 as standard (50). The sensitivity of the assay was 1 ng/ml. Intra-assay CV was less than 10% between 1 and 22 ng/ml.

Plasma cortisol concentrations were assayed in duplicate using antiserum no. 3368 (Bioquest Ltd) and $^{125}$I-labeled cortisol (Amersham Pharmacia Biotech Ltd). The sensitivity of the assay was 3 ng/ml. Intra-assay CV was less than 10% between 3 and 18 ng/ml, and the inter-assay CV was 15%.

Data Analysis

For data analysis of LH, GH, prolactin and cortisol, the mean plasma value in each ewe was calculated for the period before (0-180 min), during (180-240 min), and after (240-360 min) the infusion. In addition, the mean LH pulse amplitude for each ewe was also calculated before, during, and after the infusion. Repeated Measures ANOVAs were used to determine the effect of peptide 234 treatment on hormone levels over each period, and where appropriate one-way ANOVAs were employed to assess specific difference within each period.

EXAMPLE 3

Exemplary Pharmaceutical Formulations

Whilst it is possible for a molecule of the invention to be administered alone, it is preferable to present it as a pharmaceutical formulation, together with one or more acceptable carriers. The carrier(s) must be "acceptable" in the sense of being compatible with the agent of the invention and not deleterious to the recipients thereof. Typically, the carriers will be water or saline which will be sterile and pyrogen-free.

The following examples illustrate medicaments and pharmaceutical compositions according to the invention in which the active ingredient is a molecule of the invention.

Preferably, the molecule of the invention is provided in an amount from 10 µg to 500 mg. It will be appreciated that the following exemplary medicaments and pharmaceutical compositions may be prepared containing an amount of the molecule of the invention from 10 µg to 500 mg. For example, the agent of the invention may be present in a $10^{th}$ or $100^{th}$ or $200^{th}$ or $500^{th}$ of the amount shown in the following exemplary medicaments and pharmaceutical compositions with the amounts of the remaining ingredients changed accordingly.

EXAMPLE A

Tablet

| | |
|---|---|
| Active ingredient | 1 mg |
| Lactose | 200 mg |
| Starch | 50 mg |
| Polyvinylpyrrolidone | 5 mg |
| Magnesium stearate | 4 mg |

Tablets are prepared from the foregoing ingredients by wet granulation followed by compression.

EXAMPLE B

Ophthalmic Solution

| | |
|---|---|
| Active ingredient | 1 mg |
| Sodium chloride, analytical grade | 0.9 g |
| Thiomersal | 0.001 g |
| Purified water to | 100 ml |
| pH adjusted to | 7.5 |

EXAMPLE C

Tablet Formulations

The following formulations A and B are prepared by wet granulation of the ingredients with a solution of povidone, followed by addition of magnesium stearate and compression.

Formulation A

| | mg/tablet | mg/tablet |
|---|---|---|
| (a) Active ingredient | 1 | 1 |
| (b) Lactose B.P. | 210 | 26 |
| (c) Povidone B.P. | 15 | 9 |
| (d) Sodium Starch Glycolate | 20 | 12 |
| (e) Magnesium Stearate | 5 | 3 |
| | 251 | 51 |

Formulation B

| | mg/tablet | mg/tablet |
|---|---|---|
| (a) Active ingredient | 1 | 1 |
| (b) Lactose | 150 | — |
| (c) Avicel PH 101 ® | 60 | 26 |
| (d) Povidone B.P. | 15 | 9 |
| (e) Sodium Starch Glycolate | 20 | 12 |
| (f) Magnesium Stearate | 5 | 3 |
| | 251 | 51 |

Formulation C

|  | mg/tablet |
|---|---|
| Active ingredient | 1 |
| Lactose | 200 |
| Starch | 50 |
| Povidone | 5 |
| Magnesium stearate | 4 |
|  | 260 |

The following formulations, D and E, are prepared by direct compression of the admixed ingredients. The lactose used in formulation E is of the direction compression type.

Formulation D

|  | mg/capsule |
|---|---|
| Active Ingredient | 1 |
| Pregelatinised Starch NF15 | 150 |
|  | 151 |

Formulation E

|  | mg/capsule |
|---|---|
| Active Ingredient | 1 |
| Lactose | 150 |
| Avicel ® | 100 |
|  | 251 |

Formulation F (Controlled Release Formulation)

The formulation is prepared by wet granulation of the ingredients (below) with a solution of povidone followed by the addition of magnesium stearate and compression.

|  | mg/tablet |
|---|---|
| (a) Active Ingredient | 1 |
| (b) Hydroxypropylmethylcellulose (Methocel K4M Premium) ® | 112 |
| (c) Lactose B.P. | 53 |
| (d) Povidone B.P.C. | 28 |
| (e) Magnesium Stearate | 7 |
|  | 201 |

Drug release takes place over a period of about 6-8 hours and was complete after 12 hours.

EXAMPLE D

Capsule Formulations

Formulation A

A capsule formulation is prepared by admixing the ingredients of Formulation D in Example C above and filling into a two-part hard gelatin capsule. Formulation B (infra) is prepared in a similar manner.

Formulation B

|  | mg/capsule |
|---|---|
| (a) Active ingredient | 1 |
| (b) Lactose B.P. | 143 |
| (c) Sodium Starch Glycolate | 25 |
| (d) Magnesium Stearate | 2 |
|  | 171 |

Formulation C

|  | mg/capsule |
|---|---|
| (a) Active ingredient | 1 |
| (b) Macrogol 4000 BP | 350 |
|  | 351 |

Capsules are prepared by melting the Macrogol 4000 BP, dispersing the active ingredient in the melt and filling the melt into a two-part hard gelatin capsule.

Formulation D

|  | mg/capsule |
|---|---|
| Active ingredient | 1 |
| Lecithin | 100 |
| Arachis Oil | 100 |
|  | 201 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  | mg/capsule |
|---|---|
| (a) Active ingredient | 1 |
| (b) Microcrystalline Cellulose | 125 |
| (c) Lactose BP | 125 |
| (d) Ethyl Cellulose | 13 |
|  | 264 |

EXAMPLE E

Injectable Formulation

| Active ingredient | 1 mg |
|---|---|
| Sterile, pyrogen free phosphate buffer (pH 7.0) | to 10 ml |

The active ingredient is dissolved in most of the phosphate buffer (35-40° C.), then made up to volume and filtered through a sterile micropore filter into a sterile 10 ml amber glass vial (type 1) and sealed with sterile closures and overseals.

EXAMPLE F

Intramuscular Injection

| | |
|---|---|
| Active ingredient | 1 mg |
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

EXAMPLE G

Syrup Suspension

| | |
|---|---|
| Active ingredient | 1 mg |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

EXAMPLE H

Suppository

| | mg/suppository |
|---|---|
| Active ingredient (63 μm)* | 1 |
| Hard Fat, BP (Witepsol H15 - Dynamit Nobel) | 1770 |
| | 1771 |

*The active ingredient is used as a powder wherein at least 90% of the particles are of 63 μm diameter or less.

*The active ingredient is used as a powder wherein at least 90% of the particles are of 63 μm diameter or less.

One fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

EXAMPLE I

Pessaries

| | mg/pessary |
|---|---|
| Active ingredient | 1 |
| Anhydrate Dextrose | 380 |
| Potato Starch | 363 |
| Magnesium Stearate | 7 |
| | 751 |

The above ingredients are mixed directly and pessaries prepared by direct compression of the resulting mixture.

The agents of the invention may also be formulated as for Zoladex, Leuprolide, Teverelix, Abarelix, Ganarelix, Goserelin etc.

EXAMPLE 4

Treatment of a Proliferative Disorder Using an Agent of the Invention

A patient with prostatic cancer who has not responded to anti-androgen therapy is administered 1 mg of an agent of the invention per day intramuscularly or a depot preparation delivering this dose according to the methods of the invention. The antagonist will decrease androgen.

EXAMPLE 5

Treatment of a Proliferative Disorder Using an Agent of the Invention

A patient with endometriosis or uterine fibroids or breast cancer is administered 1 mg of an agent of the invention per day intramuscularly or a depot preparation delivering this dose according to the methods of the invention.

EXAMPLE 6

Treatment of a Pre-Eclampsia Using an Agent of the Invention

A patient with pre-eclampsia is administered 1 mg of an agent of the invention per day intramuscularly or a depot preparation delivering this dose according to the methods of the invention.

References

Numbered References Cited in Description

1. West, A., et al., *Chromosome localization and genomic structure of the KiSS-1 metastasis suppressor gene (KISS1)*. Genomics, 1998. 54(1): p. 145-8.
2. Lee, D. K., et al., *Discovery of a receptor related to the galanin receptors*. FEBS Lett, 1999. 446(1): p. 103-7.
3. Kotani, M., et al., *The metastasis suppressor gene KiSS-1 encodes kisspeptins, the natural ligands of the orphan G protein-coupled receptor GPR54*. J Biol Chem, 2001. 276 (37): p. 34631-6.
4. Muir, A. I., et al., *AXOR12, a novel human G protein-coupled receptor, activated by the peptide KiSS-1*. J Biol Chem, 2001. 276(31): p. 28969-75.

5. Stafford, L. J., et al., *Identification and characterization of mouse metastasis-suppressor KiSS1 and its G-protein-coupled receptor*. Cancer Res, 2002. 62(19): p. 5399-404.
6. Castellano, J. M., et al., *Expression of KiSS-1 in rat ovary: putative local regulator of ovulation?* Endocrinology, 2006. 147(10): p. 4852-62.
7. Yamada, S., et al., *Inhibition of Metastin (Kisspeptin-54)-GPR 54 Signaling in the Arcuate Nucleus-Median Eminence Region during Lactation in Rats*. Endocrinology, 2007.
8. Seminara, S. B., et al., *The GPR54 gene as a regulator of puberty*. N Engl J Med, 2003. 349(17): p. 1614-27.
9. de Roux, N., et al., *Hypogonadotropic hypogonadism due to loss of function of the KiSS1-derived peptide receptor GPR54*. Proc Natl Acad Sci USA, 2003. 100(19): p. 10972-6.
10. Semple, R. K., et al., *Two novel missense mutations in g protein-coupled receptor 54 in a patient with hypogonadotropic hypogonadism*. J Clin Endocrinol Metab, 2005. 90(3): p. 1849-55.
11. Lanfranco, F., et al., *Role of sequence variations of the GnRH receptor and G protein-coupled receptor 54 gene in male idiopathic hypogonadotropic hypogonadism*. Eur J Endocrinol, 2005. 153(6): p. 845-52.
12. Cerrato, F., et al., *Coding sequence analysis of GNRHR and GPR54 in patients with congenital and adult-onset forms of hypogonadotropic hypogonadism*. Eur J Endocrinol, 2006. 155 Suppl 1: p. S3-S10.
13. Pallais, J. C., et al., *Neuroendocrine, gonadal, placental, and obstetric phenotypes in patients with IHH and mutations in the G-protein coupled receptor, GPR54*. Mol Cell Endocrinol, 2006. 254-255: p. 70-7.
14. Funes, S., et al., *The KiSS-1 receptor GPR54 is essential for the development of the murine reproductive system*. Biochem Biophys Res Commun, 2003. 312(4): p. 1357-63.
15. Shahab, M., et al., *Increased hypothalamic GPR54 signaling: a potential mechanism for initiation of puberty in primates*. Proc Natl Acad Sci USA, 2005. 102(6): p. 2129-34.
16. Clarkson, J. and A. E. Herbison, *Postnatal development of kisspeptin neurons in mouse hypothalamus; sexual dimorphism and projections to gonadotropin-releasing hormone neurons*. Endocrinology, 2006. 147(12): p. 5817-25.
17. Han, S. K., et al., *Activation of gonadotropin-releasing hormone neurons by kisspeptin as a neuroendocrine switch for the onset of puberty*. J Neurosci, 2005. 25(49): p. 11349-56.
18. Thompson, E. L., et al., *Central and peripheral administration of kisspeptin-10 stimulates the hypothalamic-pituitary-gonadal axis*. J Neuroendocrinol, 2004. 16(10): p. 850-8.
19. Navarro, V. M., et al., *Effects of KiSS-1 peptide, the natural ligand of GPR54, on follicle-stimulating hormone secretion in the rat*. Endocrinology, 2005. 146(4): p. 1689-97.
20. Dhillo, W. S., et al., *Kisspeptin-54 stimulates the hypothalamic-pituitary gonadal axis in human males*. J Clin Endocrinol Metab, 2005. 90(12): p. 6609-15.
21. Messager, S., et al., *Kisspeptin directly stimulates gonadotropin-releasing hormone release via G protein-coupled receptor 54*. Proc Natl Acad Sci USA, 2005. 102(5): p. 1761-6.
22. Pompolo, S., et al., *Colocalization of kisspeptin and gonadotropin-releasing hormone in the ovine brain*. Endocrinology, 2006. 147(2): p. 804-10.
23. Jacobi, J. S., et al., *17-Beta-Estradiol Directly Regulates the Expression of Adrenergic Receptors and Kisspeptin/GPR54 System in GT1-7 GnRH Neurons*. Neuroendocrinology, 2007.
24. Gutierrez-Pascual, E., et al., *Direct pituitary effects of kisspeptin: activation of gonadotrophs and somatotrophs and stimulation of luteinising hormone and growth hormone secretion*. J Neuroendocrinol, 2007. 19(7): p. 521-30.
25. Suzuki, S., H. Kadokawa, and T. Hashizume, *Direct kisspeptin-10 stimulation on luteinizing hormone secretion from bovine and porcine anterior pituitary cells*. Anim Reprod Sci, 2007.
26. Smith, J. T., et al., *Differential regulation of KiSS-1 mRNA expression by sex steroids in the brain of the male mouse*. Endocrinology, 2005. 146(7): p. 2976-84.
27. Estrada, K. M., et al., *Elevated KiSS-1 expression in the arcuate nucleus prior to the cyclic preovulatory gonadotrophin-releasing hormone/lutenising hormone surge in the ewe suggests a stimulatory role for kisspeptin in oestrogen-positive feedback*. J Neuroendocrinol, 2006. 18(10): p. 806-9.
28. Franceschini, I., et al., *Kisspeptin immunoreactive cells of the ovine preoptic area and arcuate nucleus co-express estrogen receptor alpha*. Neurosci Lett, 2006. 401(3): p. 225-30.
29. Adachi, S., et al., *Involvement of Anteroventral Periventricular Metastin/Kisspeptin Neurons in Estrogen Positive Feedback Action on Luteinizing Hormone Release in Female Rats*. J Reprod Dev, 2007.
30. Mason, A. O., et al., *Suppression of kisspeptin expression and gonadotropic axis sensitivity following exposure to inhibitory day lengths in female Siberian hamsters*. Horm Behav, 2007.
31. Revel, F. G., et al., *Kisspeptin mediates the photoperiodic control of reproduction in hamsters*. Curr Biol, 2006. 16(17): p. 1730-5.
32. Revel, F. G., et al., *KiSS-1: a likely candidate for the photoperiodic control of reproduction in seasonal breeders*. Chronobiol Int, 2006. 23(1-2): p. 277-87.
33. Greives, T. J., et al., *Environmental Control of Kisspeptin: Implications for Seasonal Reproduction*. Endocrinology, 2006.
34. Luque, R. M., R. D. Kineman, and M. Tena-Sempere, *Regulation of hypothalamic expression of KiSS-1 and GPR54 genes by metabolic factors: Analyses using mouse models and a cell line*. Endocrinology, 2007.
35. Castellano, J. M., et al., *Changes in hypothalamic KiSS-1 system and restoration of pubertal activation of the reproductive axis by kisspeptin in undernutrition*. Endocrinology, 2005. 146(9): p. 3917-25.
36. Mead, E. J., et al., *Kisspeptins are novel potent vasoconstrictors in humans, with a discrete localization of their receptor GPR54, to atherosclerosis prone vessels*. Endocrinology, 2006.
37. Arai, A. C., et al., *Cancer metastasis-suppressing peptide metastin upregulates excitatory synaptic transmission in hippocampal dentate granule cells*. J Neurophysiol, 2005. 94(5): p. 3648-52.
38. Gaytan, M., et al., *Expression of KiSS-1 in rat oviduct: possible involvement in prevention of ectopic implantation?* Cell Tissue Res, 2007.
39. Janneau, J. L., et al., *Transcriptional expression of genes involved in cell invasion and migration by normal and tumoral trophoblast cells*. J Clin Endocrinol Metab, 2002. 87(11): p. 5336-9.

40. Horikoshi, Y., et al., *Dramatic elevation of plasma metastin concentrations in human pregnancy: metastin as a novel placenta-derived hormone in humans.* J Clin Endocrinol Metab, 2003. 88(2): p. 914-9.

41. Terao, Y., et al., *Expression of KiSS-1, a metastasis suppressor gene, in trophoblast giant cells of the rat placenta.* Biochim Biophys Acta, 2004. 1678(2-3): p. 102-10.

42. Bilban, M., et al., *Kisspeptin-10, a KiSS-1/metastin-derived decapeptide, is a physiological invasion inhibitor of primary human trophoblasts.* J Cell Sci, 2004. 117(Pt 8): p. 1319-28.

43. Masui, T., et al., *Metastin and its variant forms suppress migration of pancreatic cancer cells.* Biochem Biophys Res Commun, 2004. 315(1): p. 85-92.

44. Ringel, M. D., et al., *Metastin receptor is overexpressed in papillary thyroid cancer and activates MAP kinase in thyroid cancer cells.* J Clin Endocrinol Metab, 2002. 87(5): p. 2399.

45. Schmid, K., et al., *KiSS-1 overexpression as an independent prognostic marker in hepatocellular carcinoma: an immunohistochemical study.* Virchows Arch, 2007.

46. Navenot, J. M., et al., *Kisspeptin-10-induced signaling of GPR54 negatively regulates chemotactic responses mediated by CXCR4: a potential mechanism for the metastasis suppressor activity of kisspeptins.* Cancer Res, 2005. 65(22): p. 10450-6.

47. Stathatos, N., et al., *KiSS-1/G protein-coupled receptor 54 metastasis suppressor pathway increases myocyte-enriched calcineurin interacting protein 1 expression and chronically inhibits calcineurin activity.* J Clin Endocrinol Metab, 2005. 90(9): p. 5432-40.

48. Shirasaki, F., et al., *Loss of expression of the metastasis suppressor gene KiSS1 during melanoma progression and its association with LOH of chromosome 6q16.3-q23.* Cancer Res, 2001. 61(20): p. 7422-5.

49. Mitchell, D. C., et al., *Transcriptional regulation of KiSS-1 gene expression in metastatic melanoma by specificity protein-1 and its coactivator DRIP-130.* Oncogene, 2007. 26(12): p. 1739-47.

50. Ohtaki, T., et al., *Metastasis suppressor gene KiSS-1 encodes peptide ligand of a G-protein-coupled receptor.* Nature, 2001. 411(6837): p. 613-7.

51. Hori, A., et al., *Metastin suppresses the motility and growth of CHO cells transfected with its receptor.* Biochem Biophys Res Commun, 2001. 286(5): p. 958-63.

52. Niida, A., et al., *Design and synthesis of downsized metastin (45-54) analogs with maintenance of high GPR54 agonistic activity.* Bioorg Med Chem Lett, 2006. 16(1): p. 134-7.

53. Orsini, M. J., et al., *Metastin (KiSS-1) mimetics identified from peptide structure-activity relationship-derived pharmacophores and directed small molecule database screening.* J Med Chem, 2007. 50(3): p. 462-71.

54. Qiao, C., et al., *[Clinical significance of KiSS-1 and matrix metalloproteinase-9 expression in trophoblasts of women with preeclampsia and their relation to perinatal outcome of neonates].* Zhonghua Fu Chan Ke Za Zhi, 2005. 40(9): p. 585-90.

Numbered References Cited in Example 2

1. Porkka-Heiskanen, T., Khoshaba, N., Scarbrough, K., Urban, J. H., Vitaterna, M. H., Levine, J. E., Turek, F. W., and Horton, T. H. 1997. Rapid photoperiod-induced increase in detectable GnRH mRNA-containing cells in Siberian hamster. *Am J Physiol* 273:R2032-2039.

2. Richardson, H. N., Nelson, A. L., Ahmed, E. I., Parfitt, D. B., Romeo, R. D., and Sisk, C. L. 2004. Female pheromones stimulate release of luteinizing hormone and testosterone without altering GnRH mRNA in adult male Syrian hamsters (*Mesocricetus auratus*). *Gen Comp Endocrinol* 138:211-217.

3. Centeno, M. L., Sanchez, R. L., Cameron, J. L., and Bethea, C. L. 2007. Hypothalamic gonadotrophin-releasing hormone expression in female monkeys with different sensitivity to stress. *J Neuroendocrinol* 19:594-604.

4. Seminara, S. B., Messager, S., Chatzidaki, E. E., Thresher, R. R., Acierno, J. S., Jr., Shagoury, J. K., Bo-Abbas, Y., Kuohung, W., Schwinof, K. M., Hendrick, A. G., et al. 2003. The GPR54 gene as a regulator of puberty. *N Engl J Med* 349:1614-1627.

5. de Roux, N., Genin, E., Carel, J. C., Matsuda, F., Chaussain, J. L., and Milgrom, E. 2003. Hypogonadotropic hypogonadism due to loss of function of the KiSS1-derived peptide receptor GPR54. *Proc Natl Acad Sci USA* 100:10972-10976.

6. Kotani, M., Detheux, M., Vandenbogaerde, A., Communi, D., Vanderwinden, J. M., Le Poul, E., Brezillon, S., Tyldesley, R., Suarez-Huerta, N., Vandeput, F., et al. 2001. The metastasis suppressor gene KiSS-1 encodes kisspeptins, the natural ligands of the orphan G protein-coupled receptor GPR54. *J Biol Chem* 276:34631-34636.

7. Muir, A. I., Chamberlain, L., Elshourbagy, N. A., Michalovich, D., Moore, D. J., Calamari, A., Szekeres, P. G., Sarau, H. M., Chambers, J. K., Murdock, P., et al. 2001. AXOR12, a novel human G protein-coupled receptor, activated by the peptide KiSS-1. *J Biol Chem* 276:28969-28975.

8. Seminara, S. B., and Kaiser, U. B. 2005. New gatekeepers of reproduction: GPR54 and its cognate ligand, KiSS-1. *Endocrinology* 146:1686-1688.

9. Gottsch, M. L., Cunningham, M. J., Smith, J. T., Popa, S. M., Acohido, B. V., Crowley, W. F., Seminara, S., Clifton, D. K., and Steiner, R. A. 2004. A role for kisspeptins in the regulation of gonadotropin secretion in the mouse. *Endocrinology* 145:4073-4077.

10. Irwig, M. S., Fraley, G. S., Smith, J. T., Acohido, B. V., Popa, S. M., Cunningham, M. J., Gottsch, M. L., Clifton, D. K., and Steiner, R. A. 2004. Kisspeptin activation of gonadotropin releasing hormone neurons and regulation of KiSS-1 mRNA in the male rat. *Neuroendocrinology* 80:264-272.

11. Smith, J. T., Dungan, H. M., Stoll, E. A., Gottsch, M. L., Braun, R. E., Eacker, S. M., Clifton, D. K., and Steiner, R. A. 2005. Differential regulation of KiSS-1 mRNA expression by sex steroids in the brain of the male mouse. *Endocrinology* 146:2976-2984.

12. Estrada, K. M., Clay, C. M., Pompolo, S., Smith, J. T., and Clarke, I. J. 2006. Elevated KiSS-1 expression in the arcuate nucleus prior to the cyclic preovulatory gonadotrophin-releasing hormone/lutenising hormone surge in the ewe suggests a stimulatory role for kisspeptin in oestrogen-positive feedback. *J Neuroendocrinol* 18:806-809.

13. Revel, F. G., Saboureau, M., Masson-Pevet, M., Pevet, P., Mikkelsen, J. D., and Simonneaux, V. 2006. Kisspeptin mediates the photoperiodic control of reproduction in hamsters. *Curr Biol* 16:1730-1735.

14. Revel, F. G., Saboureau, M., Masson-Pevet, M., Pevet, P., Mikkelsen, J. D., and Simonneaux, V. 2006. KiSS-1: a likely candidate for the photoperiodic control of reproduction in seasonal breeders. *Chronobiol Int* 23:277-287.

15. Greives, T. J., Mason, A. O., Scotti, M. A., Levine, J., Ketterson, E. D., Kriegsfeld, L. J., and Demas, G. E. 2006. Environmental Control of Kisspeptin: Implications for Seasonal Reproduction. *Endocrinology.*

16. Castellano, J. M., Navarro, V. M., Fernandez-Fernandez, R., Nogueiras, R., Tovar, S., Roa, J., Vazquez, M. J., Vigo, E., Casanueva, F. F., Aguilar, E., et al. 2005. Changes in hypothalamic KiSS-1 system and restoration of pubertal activation of the reproductive axis by kisspeptin in undernutrition. *Endocrinology* 146:3917-3925.

17. Millar, R. P., Lu, Z. L., Pawson, A. J., Flanagan, C. A., Morgan, K., and Maudsley, S. R. 2004. Gonadotropin-releasing hormone receptors. *Endocr Rev* 25:235-275.

18. Conn, P. M., and Crowley, W. F., Jr. 1994. Gonadotropin-releasing hormone and its analogs. *Annu Rev Med* 45:391-405.

19. Horikoshi, Y., Matsumoto, H., Takatsu, Y., Ohtaki, T., Kitada, C., Usuki, S., and Fujino, M. 2003. Dramatic elevation of plasma metastin concentrations in human pregnancy: metastin as a novel placenta-derived hormone in humans. *J Clin Endocrinol Metab* 88:914-919.

20. Janneau, J. L., Maldonado-Estrada, J., Tachdjian, G., Miran, I., Motte, N., Saulnier, P., Sabourin, J. C., Cote, J. F., Simon, B., Frydman, R., et al. 2002. Transcriptional expression of genes involved in cell invasion and migration by normal and tumoral trophoblast cells. *J Clin Endocrinol Metab* 87:5336-5339.

21. Bilban, M., Ghaffari-Tabrizi, N., Hintermann, E., Bauer, S., Molzer, S., Zoratti, C., Malli, R., Sharabi, A., Hiden, U., Graier, W., et al. 2004. Kisspeptin-10, a KiSS-1/metastin-derived decapeptide, is a physiological invasion inhibitor of primary human trophoblasts. *J Cell Sci* 117:1319-1328.

22. Mead, E. J., Maguire, J. J., Kuc, R. E., and Davenport, A. P. 2006. Kisspeptins are novel potent vasoconstrictors in humans, with a discrete localization of their receptor GPR54, to atherosclerosis prone vessels. *Endocrinology*.

23. Han, S. K., Gottsch, M. L., Lee, K. J., Popa, S. M., Smith, J. T., Jakawich, S. K., Clifton, D. K., Steiner, R. A., and Herbison, A. E. 2005. Activation of gonadotropin-releasing hormone neurons by kisspeptin as a neuroendocrine switch for the onset of puberty. *J Neurosci* 25:11349-11356.

24. Keen, K. L., Wegner, F. H., Bloom, S. R., Ghatei, M. A., and Terasawa, E. 2008. An Increase in Kisspeptin-54 Release Occurs with the Pubertal Increase in LHRH-1 Release in the Stalk-Median Eminence of Female Rhesus Monkeys In Vivo. *Endocrinology*.

25. Frost, S. I., Keen, K. L., Levine, J. E., and Terasawa, E. 2008. Microdialysis methods for in vivo neuropeptide measurement in the stalk-median eminence in the Rhesus monkey. *J Neurosci Methods* 168:26-34.

26. Orsini, M. J., Klein, M. A., Beavers, M. P., Connolly, P. J., Middleton, S. A., and Mayo, K. H. 2007. Metastin (KiSS-1) mimetics identified from peptide structure-activity relationship-derived pharmacophores and directed small molecule database screening. *J Med Chem* 50:462-471.

27. Tomita, K., Niida, A., Oishi, S., Ohno, H., Cluzeau, J., Navenot, J. M., Wang, Z. X., Peiper, S. C., and Fujii, N. 2006. Structure-activity relationship study on small peptidic GPR54 agonists. *Bioorg Med Chem* 14:7595-7603.

28. Clements, M. K., McDonald, T. P., Wang, R., Xie, G., O'Dowd, B. F., George, S. R., Austin, C. P., and Liu, Q. 2001. FMRFamide-related neuropeptides are agonists of the orphan G-protein-coupled receptor GPR54. *Biochem Biophys Res Commun* 284:1189-1193.

29. Gottsch, M. L., Clifton, D. K., and Steiner, R. A. 2006. Kisspeptin-GPR54 signaling in the neuroendocrine reproductive axis. *Mol Cell Endocrinol* 254-255:91-96.

30. Tenenbaum-Rakover, Y., Commenges-Ducos, M., Iovane, A., Aumas, C., Admoni, O., and de Roux, N. 2006. Neuroendocrine Phenotype Analysis in Five Patients with Isolated Hypogonadotropic Hypogonadism Due to a L102P Inactivating Mutation of GPR54. *J Clin Endocrinol Metab*.

31. Blank, S. K., McCartney, C. R., and Marshall, J. C. 2006. The origins and sequelae of abnormal neuroendocrine function in polycystic ovary syndrome. *Hum Reprod Update* 12:351-361.

32. Li, X. F., Kinsey-Jones, J. S., Knox, A. M., Wu, X. Q., Tahsinsoy, D., Brain, S. D., Lightman, S. L., and O'Byrne K, T. 2007. Neonatal lipopolysaccharide exposure exacerbates stress-induced suppression of LH pulse frequency in adulthood. *Endocrinology*.

33. Dong, Q., Li, B., Rintala, H., Blair, S., Spaliviero, J., and Handelsman, D. J. 1993. LH pulsatility, biopotency, and clearance during undernutrition in orchidectomized mature rats. *Am J Physiol* 265:E304-313.

34. Adachi, S., Yamada, S., Takatsu, Y., Matsui, H., Kinoshita, M., Takase, K., Sugiura, H., Ohtaki, T., Matsumoto, H., Uenoyama, Y., et al. 2007. Involvement of anteroventral periventricular metastin/kisspeptin neurons in estrogen positive feedback action on luteinizing hormone release in female rats. *J Reprod Dev* 53:367-378.

35. Kinoshita, M., Tsukamura, H., Adachi, S., Matsui, H., Uenoyama, Y., Iwata, K., Yamada, S., Inoue, K., Ohtaki, T., Matsumoto, H., et al. 2005. Involvement of central metastin in the regulation of preovulatory luteinizing hormone surge and estrous cyclicity in female rats. *Endocrinology* 146:4431-4436.

36. Clarke, I. J. 1993. Variable patterns of gonadotropin-releasing hormone secretion during the estrogen-induced luteinizing hormone surge in ovariectomized ewes. *Endocrinology* 133:1624-1632.

37. Roa, J., Vigo, E., Castellano, J. M., Navarro, V. M., Fernandez-Fernandez, R., Casanueva, F. F., Dieguez, C., Aguilar, E., Pinilla, L., and Tena-Sempere, M. 2006. Hypothalamic expression of KiSS-1 system and gonadotropin-releasing effects of kisspeptin in different reproductive states of the female Rat. *Endocrinology* 147:2864-2878.

38. Dhillo, W. S., Chaudhri, O. B., Thompson, E. L., Murphy, K. G., Patterson, M., Ramachandran, R., Nijher, G. K., Amber, V., Kokkinos, A., Donaldson, M., et al. 2007. Kisspeptin-54 stimulates gonadotropin release most potently during the preovulatory phase of the menstrual cycle in women. *J Clin Endocrinol Metab* 92:3958-3966.

39. Dhillo, W. S., Chaudhri, O. B., Patterson, M., Thompson, E. L., Murphy, K. G., Badman, M. K., McGowan, B. M., Amber, V., Patel, S., Ghatei, M. A., et al. 2005. Kisspeptin-54 stimulates the hypothalamic-pituitary gonadal axis in human males. *J Clin Endocrinol Metab* 90:6609-6615.

40. Arai, A. C., Xia, Y. F., Suzuki, E., Kessler, M., Civelli, O., and Nothacker, H. P. 2005. Cancer metastasis-suppressing peptide metastin upregulates excitatory synaptic transmission in hippocampal dentate granule cells. *J Neurophysiol* 94:3648-3652.

41. Hiden, U., Bilban, M., Knofler, M., and Desoye, G. 2007. Kisspeptins and the placenta: Regulation of trophoblast invasion. *Rev Endocr Metab Disord*.

42. Suter, K. J., Song, W. J., Sampson, T. L., Wuarin, J. P., Saunders, J. T., Dudek, F. E., and Moenter, S. M. 2000. Genetic targeting of green fluorescent protein to gonadotropin-releasing hormone neurons: characterization of whole-cell electrophysiological properties and morphology. *Endocrinology* 141:412-419.

43. Christian, C. A., Mobley, J. L., and Moenter, S. M. 2005. Diurnal and estradiol-dependent changes in gonadotropin-releasing hormone neurone firing activity. *Proc Natl Acad Sci USA* 102:15682-15687.

44. Nunemaker, C. S., DeFazio, R. A., and Moenter, S. M. 2002. Estradiol-sensitive afferents modulate long-term episodic firing patterns of GnRH neurons. *Endocrinology* 143:2284-2292.
45. Pielecka, J., and Moenter, S. M. 2006. Effect of steroid milieu on gonadotropin-releasing hormone-1 neuron firing pattern and luteinizing hormone levels in male mice. *Biol Reprod* 74:931-937.
46. Gearing, M., and Terasawa, E. 1988. Luteinizing hormone releasing hormone (LHRH) neuroterminals mapped using the push-pull perfusion method in the rhesus monkey. *Brain Res Bull* 21:117-121.
47. Merriam, G. R., and Wachter, K. W. 1982. Algorithms for the study of episodic hormone secretion. *Am J Physiol* 243:E310-318.
48. Navarro, V. M., Castellano, J. M., Fernandez-Fernandez, R., Tovar, S., Roa, J., Mayen, A., Nogueiras, R., Vazquez, M. J., Barreiro, M. L., Magni, P., et al. 2005. Characterization of the potent luteinizing hormone-releasing activity of KiSS-1 peptide, the natural ligand of GPR54. *Endocrinology* 146:156-163.
49. Barker-Gibb, M. L., Scott, C. J., Boublik, J. H., and Clarke, I. J. 1995. The role of neuropeptide Y (NPY) in the control of LH secretion in the ewe with respect to season, NPY receptor subtype and the site of action in the hypothalamus. *J Endocrinol* 147:565-579.
50. Thomas, G. B., Mercer, J. E., Karalis, T., Rao, A., Cummins, J. T., and Clarke, I. J. 1990. Effect of restricted feeding on the concentrations of growth hormone (GH), gonadotropins, and prolactin (PRL) in plasma, and on the amounts of messenger ribonucleic acid for GH, gonadotropin subunits, and PRL in the pituitary glands of adult ovariectomized ewes. *Endocrinology* 126:1361-1367.

The invention claimed is:

1. A peptide molecule comprising the sequence:

$X^1$-G/W-$X^2$-R/(D)R-$X^3$      (SEQ ID NO: 3)

wherein:
$X^1$ is F or A or any D-amino-acid residue;
$X^2$ is L or A or any D-amino-acid residue;
$X^3$ is F or W;
wherein the C-terminal amino acid residue of the peptide molecule contains group z which removes the charge on that residue; and,
wherein the peptide molecule further comprises the sequence: R-R-M-K-W-K-K-Y (SEQ ID NO: 20) at the N-terminus;
and further wherein the peptide sequence is not:

```
F-G-L-R-F;          (SEQ ID NO: 4)
F-G-L-R-W;          (SEQ ID NO: 5)
F-G-(D)F-R-F;       (SEQ ID NO: 6)
F-G-A-R-W;          (SEQ ID NO: 7)
F-G-L-(D)R-W;       (SEQ ID NO: 8)
F-G-(D)L-R-W;       (SEQ ID NO: 9)
A-G-L-R-W;          (SEQ ID NO: 17)
or
(D)F-G-L-R-W        (SEQ ID NO: 10).
```

2. The peptide molecule according to claim 1, wherein $X^1$ is (D)F.

3. The peptide molecule according to claim 1, wherein $X^2$ is a D-amino-acid residue selected from the group consisting of: (D)F, (D)L and (D)W.

4. The peptide molecule according to claim 1, wherein the peptide sequence is selected from the group consisting of:

```
(D)F-W-L-R-W;       (SEQ ID NO: 11)
and
F-G-(D)W-R-F        (SEQ ID NO: 12).
```

5. The peptide molecule according to claim 1, wherein the N-terminal residue contains group y which removes the charge on that residue.

6. The peptide molecule of claim 1, wherein z is $NH_2$ or N-propylamide or N-ethylamide (NHEt) or N-methylamide or N-butylamide.

7. A pharmaceutical composition comprising an effective amount of a peptide molecule according to claim 1, and a pharmaceutically-acceptable excipient or diluent.

8. A peptide molecule comprising the sequence:

$X^A$-$X^B$-$X^C$-N-$X^D$-$X^E$-G-$X^F$-R-F      (SEQ ID NO: 29)

wherein:
$X^A$ is Y or any D-amino-acid residue;
$X^B$ is N or any D-amino acid residue;
$X^C$ is W or any D-amino acid residue;
$X^D$ is G or S or any D-amino acid residue;
$X^E$ is F or (D)W or (D)L;
$X^F$ is W or L or any D-amino acid residue;
wherein the C-terminal amino acid residue of the peptide molecule contains group z which removes the charge on that residue; and
wherein the peptide molecule further comprises the sequence: R-R-M-K-W-K-K-Y (SEQ ID NO: 20) at the N-terminus;
and further wherein the peptide sequence is not:

```
Y-N-W-N-S-F-G-L-R-F;            (SEQ ID NO: 30)
(D)Y-(D)N-W-N-S-F-G-W-R-F;      (SEQ ID NO: 31)
(D)Y-(D)N-W-N-G-F-G-W-R-F;      (SEQ ID NO: 32)
(D)Y-(D)N-W-N-S-F-G-(D)W-R-F;   (SEQ ID NO: 33)
or
(D)Y-(D)N-W-N-G-F-G-(D)W-R-F    (SEQ ID NO: 34).
```

9. The peptide molecule according to claim 8, wherein $X^A$ is a D-amino-acid residue selected from the group consisting of: (D)F and (D)Y and (D)A.

10. The peptide molecule according to claim 8, wherein $X^B$ is a D-amino-acid residue selected from the group consisting of: (D)A and (D)N.

11. The peptide molecule according to claim 8, wherein when one of $X^A$ or $X^B$ is (D)Y, the other is not (D)N.

12. The peptide molecule according to claim 8, wherein $X^A$ and $X^B$ are not both a D-amino acid residue.

13. The peptide molecule according to claim 8, wherein when $X^F$ is (D)W, $X^A$ is (D)F.

14. The peptide molecule according to claim 8, wherein $X^C$ is a D-amino-acid residue selected from the group consisting of: (D)A and (D)W.

15. The peptide molecule according to claim 8, wherein $X^D$ is a D-amino-acid residue selected from the group consisting of: (D)A and (D)W.

16. The peptide molecule according to claim 8, wherein when $X^D$ is S, $X^F$ is (D)W and/or $X^A$ is not (D)Y.

17. The peptide molecule according to claim 8, wherein when $X^D$ is S, $X^F$ is (D)W and/or $X^A$ is (D)A.

18. The peptide molecule according to claim 8, wherein $X^F$ is a D-amino-acid residue selected from the group consisting of: (D)L and (D)W.

19. The peptide molecule according to claim 8, wherein when $X^E$ and $X^F$ are both (D)W, $X^A$ is not (D)Y.

20. The peptide molecule according to claim 8, wherein when $X^E$ and $X^F$ are both (D)W, $X^A$ is (D)A.

21. The peptide molecule according to claim 8, wherein the N-terminal residue contains group y which removes the charge on that residue.

22. The peptide molecule according to claim 8, wherein the peptide sequence is selected from the group consisting of:

a) Y-N-W-N-G-F-G-L-R-F.z;       (SEQ ID NO: 35)

b) Y-N-W-N-G-F-G-(D)L-R-F.z;    (SEQ ID NO: 36)

c) Y-N-W-N-G-F-G-(D)W-R-F.z;    (SEQ ID NO: 37) and, d) Y-N-W-N-G-(D)W-G-L-R-F.z     (SEQ ID NO: 38).

23. The peptide molecule of claim 8, wherein z is $NH_2$ or N-propylamide or N-ethylamide (NHEt) or N-methylamide or N-butylamide.

24. A pharmaceutical composition comprising an effective amount of a peptide molecule according claim 8, and a pharmaceutically-acceptable excipient or diluent.

25. The peptide molecule wherein the peptide sequence is selected from the group consisting of:

a) Y-N-W-N-G-F-G-L-R-F.z;       (SEQ ID NO: 35)

b) Y-N-W-N-G-F-G-(D)L-R-F.z;    (SEQ ID NO: 36)

c) Y-N-W-N-G-F-G-(D)W-R-F.z;    (SEQ ID NO: 37)

d) Y-N-W-N-G-(D)W-G-L-R-F.z;    (SEQ ID NO: 38)

e) ac.Y-N-W-N-G-F-G-(D)W-R-F.z;     (SEQ ID NO: 39)

f) ac.Y-N-W-N-(D)W-F-G-(D)W-R-F.z;  (SEQ ID NO: 40)

g) ac.(D)Y-N-W-N-G-F-G-(D)W-R-F.z;  (SEQ ID NO: 41)

h) ac.Y-N-(D)W-N-G-F-G-(D)W-R-F.z;  (SEQ ID NO: 42)

i) ac.Y-(D)N-W-N-G-F-G-(D)W-R-F.z;  (SEQ ID NO: 43)

j) ac.Y-N-W-N-(D)A-F-G-(D)W-R-F.z;  (SEQ ID NO: 44)

k) ac.(D)A-N-W-N-G-F-G-(D)W-R-F.z;  (SEQ ID NO: 45)

l) ac.Y-N-(D)A-N-G-F-G-(D)W-R-F.z;  (SEQ ID NO: 46)

m) ac.Y-(D)A-W-N-G-F-G-(D)W-R-F.z;  (SEQ ID NO: 47)

n) ac.(D)W-N-W-N-G-F-G-(D)W-R-F.z;  (SEQ ID NO: 48)

o) ac.(D)F-N-W-N-G-F-G-(D)W-R-F.z;  (SEQ ID NO: 49)

p) ac.(D)Y-N-W-N-G-(D)W-G-(D)W-R-F.z;  (SEQ ID NO: 50)

q) ac.(D)A-N-W-N-G-(D)W-G-(D)W-R-F.z;  (SEQ ID NO: 51)

r) ac.(D)A-N-W-N-S-F-G-(D)W-R-F.z;  (SEQ ID NO: 52)

s) ac.(D)A-N-W-N-G-F-G-W-R-F.z;     (SEQ ID NO: 53)

t) ac.(D)A-N-W-N-(D)S-F-G-(D)W-R-F.z;  (SEQ ID NO: 54) and u) ac.(D)A-N-W-N-G-F-G-(D)L-R-F.z.  (SEQ ID NO: 55)

* * * * *